US008691838B2

(12) United States Patent
Albrecht et al.

(10) Patent No.: US 8,691,838 B2
(45) Date of Patent: Apr. 8, 2014

(54) HETEROCYCLES AS PROTEIN KINASE INHIBITORS

(75) Inventors: Brian K. Albrecht, Cambridge, MA (US); Steven Bellon, Wellesley, MA (US); Christiane M. Bode, Somerville, MA (US); Alessandro Boezio, Somerville, MA (US); Deborah Choquette, Medford, MA (US); Jean-Christophe Harmange, Andover, MA (US)

(73) Assignee: Amgen Inc., Thousand Oaks, CA (US)

( * ) Notice: Subject to any disclaimer, the term of this patent is extended or adjusted under 35 U.S.C. 154(b) by 388 days.

(21) Appl. No.: 12/994,068

(22) PCT Filed: May 22, 2009

(86) PCT No.: PCT/US2009/045058
§ 371 (c)(1),
(2), (4) Date: Dec. 22, 2010

(87) PCT Pub. No.: WO2009/143477
PCT Pub. Date: Nov. 26, 2009

(65) Prior Publication Data
US 2011/0118285 A1   May 19, 2011

Related U.S. Application Data

(60) Provisional application No. 61/128,555, filed on May 22, 2008.

(51) Int. Cl.
*C07D 519/00* (2006.01)
*A61K 31/437* (2006.01)
*A61K 31/4709* (2006.01)
*A61P 35/00* (2006.01)

(52) U.S. Cl.
USPC .......................................... 514/300; 546/117

(58) Field of Classification Search
USPC ........................... 544/117; 514/300; 546/117
See application file for complete search history.

(56) References Cited

U.S. PATENT DOCUMENTS

| 4,772,606 | A | 9/1988 | Sircar et al. |
| 6,037,349 | A | 3/2000 | Mederski et al. |
| 2005/0020574 | A1 | 1/2005 | Hauel et al. |
| 2005/0261297 | A1 | 11/2005 | Igarashi et al. |

FOREIGN PATENT DOCUMENTS

| DE | 10 2007 026341 | 12/2008 |
| EP | 1 481 955 | 12/2004 |
| JP | 61-137886 A | 6/1986 |
| JP | 05-125077 A | 5/1993 |
| JP | 2006-502144 A | 1/2006 |
| JP | 2006-514980 A | 5/2006 |
| WO | WO 83/00864 | 3/1983 |
| WO | WO 2004/018469 | 3/2004 |
| WO | WO2004/029054 | 1/2005 |
| WO | WO 2005/004607 | 1/2005 |
| WO | WO 2005/010005 | 2/2005 |
| WO | WO 2008/008539 | 1/2008 |

OTHER PUBLICATIONS

Temple et al (J. of Org. Chem., 1973, 38(6), pp. 1095-1098).*
Koppel et al., "Potential purine antagonists. XIX. Synthesis of some 9-alkyl(aryl)-2-amino-6-substituted purines and related v-triazolo[d]pyrimidines", Journal of the American Chemical Society, vol. 81, pp. 3046-3051, 1959.
Birchmeier et al., "Met, Metastais, Motility and More", Nature Reviews/Molecular Biology, vol. 4, pp. 915-925, 2003.
Shinomiya et al., "RNA Interference reveals that Ligand-Independent Met Activity is Required for Tumor Cell Signaling and Survival", vol. 64, pp. 7962-7970, 2004.

* cited by examiner

*Primary Examiner* — Susanna Moore
(74) *Attorney, Agent, or Firm* — Olga Mekhovich

(57) ABSTRACT

Selected compounds are effective for prophylaxis and treatment of diseases, such as HGF mediated diseases. The invention encompasses novel compounds of Formula I, analogs, prodrugs and pharmaceutically acceptable salts thereof, pharmaceutical compositions and methods for prophylaxis and treatment of diseases and other maladies or conditions involving, cancer and the like. The subject invention also relates to processes for making such compounds as well as to intermediates useful in such processes.

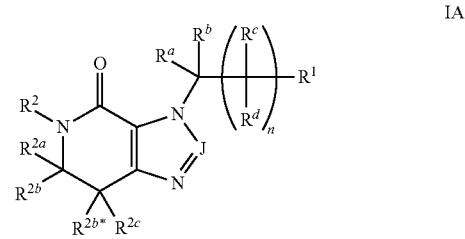

IA

5 Claims, No Drawings

HETEROCYCLES AS PROTEIN KINASE INHIBITORS

CROSS-REFERENCE TO RELATED APPLICATIONS

This application is a U.S. National Stage under 35 U.S.C. 371 of PCT Patent Application No. PCT/US09/45058, filed 22 May 2009, expired, which claims benefit of priority to U.S. Patent Application No. 61/128,555, filed 22 May 2008, each of which is incorporated by reference in its entirety.

FIELD OF THE INVENTION

This invention is in the field of pharmaceutical agents and specifically relates to compounds, compositions, uses and methods for treating cancer.

BACKGROUND OF THE INVENTION

Protein kinases represent a large family of proteins, which play a central role in the regulation of a wide variety of cellular processes, maintaining control over cellular function. A partial list of such kinases includes abl, Akt, bcr-abl, Blk, Brk, Btk, c-kit, c-Met, c-src, c-fms, CDK1, CDK2, CDK3, CDK4, CDK5, CDK6, CDK7, CDK8, CDK9, CDK10, cRaf1, CSF1R, CSK, EGFR, ErbB2, ErbB3, ErbB4, Erk, Fak, fes, FGFR1, FGFR2, FGFR3, FGFR4, FGFR5, Fgr, flt-1, Fps, Frk, Fyn, Hck, IGF-1R, INS-R, Jak, KDR, Lck, Lyn, MEK, p38, PDGFR, PIK, PKC, PYK2, ros, tie, tie2, TRK, Yes, and Zap70. Inhibition of such kinases has become an important therapeutic target.

The hepatocyte growth factor receptor ("c-Met") is a unique receptor tyrosine kinase shown to be overexpressed in a variety of malignancies. c-Met typically comprises, in its native form, a 190-kDa heterodimeric (a disulfide-linked 50-kDa α-chain and a 145-kDa β-chain) membrane-spanning tyrosine kinase protein (Proc. Natl. Acad. Sci. USA, 84:6379-6383 (1987)). c-Met is mainly expressed in epithelial cells and stimulation of c-Met leads to scattering, angiogenesis, proliferation and metastasis. (See Cytokine and Growth Factor Reviews, 13:41-59 (2002)).

The ligand for c-Met is hepatocyte growth factor (also known as scatter factor, HGF and SF). HGF is a heterodimeric protein secreted by cells of mesodermal origin (Nature, 327: 239-242 (1987); J. Cell Biol., 111:2097-2108 (1990)).

Various biological activities have been described for HGF through interaction with c-met (Hepatocyte Growth Factor-Scatter Factor (HGF-SF) and the c-Met Receptor, Goldberg and Rosen, eds., Birkhauser Verlag-Basel, 67-79 (1993). The biological effect of HGF/SF may depend in part on the target cell. HGF induces a spectrum of biological activities in epithelial cells, including mitogenesis, stimulation of cell motility and promotion of matrix invasion (Biochem. Biophys. Res. Comm., 122:1450-1459 (1984); Proc. Natl. Acad. Sci. U.S.A., 88:415-419 (1991)). It stimulates the motility and invasiveness of carcinoma cells, the former having been implicated in the migration of cells required for metastasis. HGF can also act as a "scatter factor", an activity that promotes the dissociation of epithelial and vascular endothelial cells (Nature, 327:239-242 (1987); J. Cell Biol., 111:2097-2108 (1990); EMBO J., 10:2867-2878 (1991); Proc. Natl. Acad. Sci. USA, 90:649-653 (1993)). Therefore, HGF is thought to be important in tumor invasion (Hepatocyte Growth Factor-Scatter Factor (HGF-SF) and the C-Met Receptor, Goldberg and Rosen, eds., Birkhauser Verlag-Basel, 131-165 (1993)).

HGF and c-Met are expressed at abnormally high levels in a large variety of solid tumors. High levels of HGF and/or c-Met have been observed in liver, breast, pancreas, lung, kidney, bladder, ovary, brain, prostate, gallbladder and myeloma tumors in addition to many others. The role of HGF/c-Met in metastasis has been investigated in mice using cell lines transformed with HGF/c-Met (J. Mol. Med., 74:505-513 (1996)). Overexpression of the c-Met oncogene has also been suggested to play a role in the pathogenesis and progression of thyroid tumors derived from follicular epithelium (Oncogene, 7:2549-2553 (1992)). HGF is a morphogen (Development, 110:1271-1284 (1990); Cell, 66:697-711 (1991)) and a potent angiogenic factor (J. Cell Biol., 119:629-641 (1992)).

Recent work on the relationship between inhibition of angiogenesis and the suppression or reversion of tumor progression shows great promise in the treatment of cancer (Nature, 390:404-407 (1997)), especially the use of multiple angiogenesis inhibitors compared to the effect of a single inhibitor. Angiogenesis can be stimulated by HGF, as well as vascular endothelial growth factor (VEGF) and basic fibroblast growth factor (bFGF).

Angiogenesis, the process of sprouting new blood vessels from existing vasculature and arteriogenesis, the remodeling of small vessels into larger conduit vessels are both physiologically important aspects of vascular growth in adult tissues. These processes of vascular growth are required for beneficial processes such as tissue repair, wound healing, recovery from tissue ischemia and menstrual cycling. They are also required for the development of pathological conditions such as the growth of neoplasias, diabetic retinopathy, rheumatoid arthritis, psoriasis, certain forms of macular degeneration, and certain inflammatory pathologies. The inhibition of vascular growth in these contexts has also shown beneficial effects in preclinical animal models. For example, inhibition of angiogenesis by blocking vascular endothelial growth factor or its receptor has resulted in inhibition of tumor growth and in retinopathy. Also, the development of pathological pannus tissue in rheumatoid arthritis involves angiogenesis and might be blocked by inhibitors of angiogenesis.

The ability to stimulate vascular growth has potential utility for treatment of ischemia-induced pathologies such as myocardial infarction, coronary artery disease, peripheral vascular disease, and stroke. The sprouting of new vessels and/or the expansion of small vessels in ischemic tissues prevents ischemic tissue death and induces tissue repair. Certain diseases are known to be associated with deregulated angiogenesis, for example ocular neovascularization, such as retinopathies (including diabetic retinopathy), age-related macular degeneration, psoriasis, hemangioblastoma, hemangioma, arteriosclerosis, inflammatory disease, such as a rheumatoid or rheumatic inflammatory disease, especially arthritis (including rheumatoid arthritis), or other chronic inflammatory disorders, such as chronic asthma, arterial or post-transplantational atherosclerosis, endometriosis, and neoplastic diseases, for example so-called solid tumors and liquid tumors (such as leukemias). Treatment of malaria and related viral diseases may also be mediated by HGF and cMet.

Elevated levels of HGF and c-Met have also been observed in non-oncological settings, such as hypertension, myocardial infarction and rheumatoid arthritis. It has been observed that levels of HGF increase in the plasma of patients with hepatic failure (Gohda et al., supra) and in the plasma (Hepatol., 13:734-750 (1991)) or serum (J. Biochem., 109:8-13 (1991)) of animals with experimentally induced liver damage. HGF has also been shown to be a mitogen for certain cell types, including melanocytes, renal tubular cells, keratinocytes, certain endothelial cells and cells of epithelial origin (Biochem. Biophys. Res. Commun., 176:45-51 (1991); Biochem. Biophys. Res. Commun, 174:831-838 (1991); Biochem., 30:9768-9780 (1991); Proc. Natl. Acad. Sci. USA, 88:415-419 (1991)). Both HGF and the c-Met proto-oncogene have been postulated to play a role in microglial reactions to CNS injuries (Oncogene, 8:219-222 (1993)).

Metastatic SCC cells overexpress c-Met and have enhanced tumoregenesis and metastasis in vivo (G. Gong et al., Oncogene, 23:6199-6208 (2004)). C-Met is required for tumor cell survival (N. Shinomiya et al., Cancer Research, 64:7962-7970 (2004)). For a general review see C. Birchmeier et al., Nature Reviews/Molecular Biology 4:915-925 (2003).

In view of the role of HGF and/or c-Met in potentiating or promoting such diseases or pathological conditions, it would be useful to have a means of substantially reducing or inhibiting one or more of the biological effects of HGF and its receptor. Thus a compound that reduces the effect of HGF would be a useful compound. Compounds of the current invention have not been previously described as inhibitors of angiogenesis such as for the treatment of cancer.

Sugen application WO 05/010005 describes certain Triazolotriazine compounds that are c-met inhibitors. Diamon Shamrock Corp. application WO 83/00864 discloses certain Triazolotriazine compounds that are useful as anti-inflammatory agents. Yamanouchi applications EP 1481955 and US 2005/0261297 disclose certain nitrogen-containing heterocyclic compounds that are therapeutic agents having a bone formation-stimulating effect.

Compounds of the current invention are inhibitors of c-Met.

SUMMARY OF THE INVENTION

The invention provides compounds of formula I or II

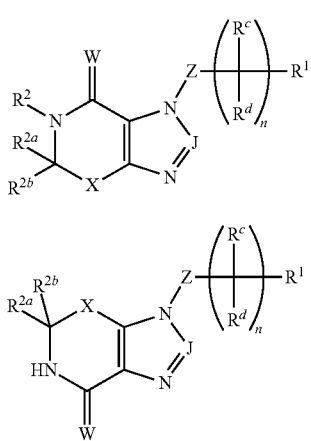

enantiomers, diastereomers, and salts thereof, wherein all substituents are listed in detail in Detailed Description.

In one aspect, the invention also provides pharmaceutical compositions comprising a compound of Formula I and II together with a pharmaceutically acceptable vehicle, adjuvant or diluent.

In another aspect, the invention relates to methods of treating cancer or a proliferative disorder in a subject, the method comprising administering an effective amount of a compound of Formula I or II to a patient in need of such treatment. In a following aspect, the invention encompasses methods of reducing tumor size in a subject, the method comprising administering an effective amount of a compound as in claim 1 to a patient of need of such treatment. The invention provides methods of reducing metastasis in a tumor in a subject, the method comprising administering an effective amount of a compound of Formula I or II to a patient in need of such treatment.

DESCRIPTION OF THE INVENTION

The invention provides a class of compounds as defined by formula I or II

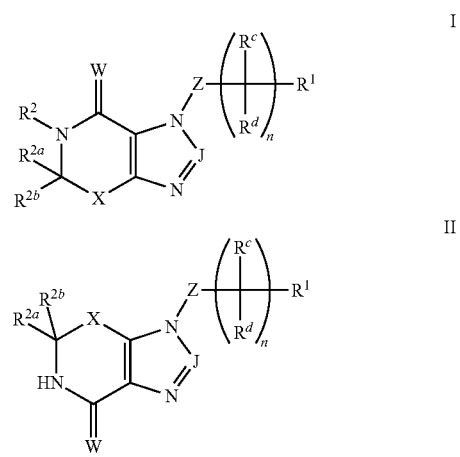

enantiomers, diastereomers, and salts thereof wherein

J is N or $CR^3$;

W is O, S or NH;

X is $CR^{2b*}R^{2c}$, or $NR^{2b+}$;

Z is $CR^aR^b$ or $S(O)_{v*}$;

$R^a$ and $R^b$ are independently H, alkyl, alkenyl, alkynyl, haloalkyl, cycloalkyl, cycloalkenyl, heterocyclo, aryl, heteroaryl, —C(=O)$R^4$, —C(=O)O$R^4$; —C(=O)N$R^5R^{5a}$ any of which may be optionally independently substituted with one or more $R^{10}$ groups as allowed by valance;

$R^c$ and $R^d$ at each occurrence are independently H, halo, alkyl, alkenyl, alkynyl, haloalkyl, cycloalkyl, cycloalkenyl, heterocyclo, aryl, heteroaryl, —$NO_2$, —CN, —N$R^5R^{5a}$, —O$R^4$, —C(=O)$R^4$, —C(=O)O$R^4$; —C(=O)N$R^5R^{5a}$, —N($R^5$)C(=O)N$R^5R^{5a}$, —N($R^5$)C(=O)$R^5$, —N($R^5$)C(=O)O$R^5$, —OC(=O)N$R^5R^{5a}$, —S(O)$_v R^4$, —S(O)$_2$N$R^5R^{5a}$, —N($R^5$)SO$_2R^4$ any of which may be optionally independently substituted with one or more $R^{10}$ groups as allowed by valance;

provided that when Z is $S(O)_{v*}R^c$ and $R^b$ on the alpha carbon to Z cannot be —$NO_2$, —CN, —N$R^5R^{5a}$, —O$R^4$, —N($R^5$)C(=O)N$R^5R^{5a}$, —N($R^5$)C(=O)$R^5$, —N($R^5$)C(=O)O$R^5$, —OC(=O)N$R^5R^{5a}$, —S(O)$_v R^4$, —S(O)$_2$N$R^5R^{5a}$, —N($R^5$)SO$_2R^4$;

or $R^a$ and $R^b$ together with the carbon atom to which they are bonded may combine to form a 3-10 membered cycloalkyl, a 3-10 membered cycloalkenyl ring, or a heterocyclo ring, any of which may be optionally substituted with one or more $R^{10}$ groups as allowed by valance;

or $R^c$ and $R^d$ together with the carbon atom to which they are bonded may combine to form a 3-10 membered cycloalkyl, a 3-10 membered cycloalkenyl ring, or a heterocyclo ring, any of which may be optionally substituted with one or more $R^{10}$ groups as allowed by valance;

or $R^a$ and/or $R^b$ may combine with any $R^c$ or $R^d$ to form a partially or fully saturated 3-8 membered cycloalkyl ring or heterocyclo ring, either of which may be optionally substituted with one or more $R^{10}$ groups as allowed by valance;

or $R^a$ and $R^b$ may combine to form a carbonyl group;

or $R^c$ and $R^d$ attached to the same carbon atom may combine to form a carbonyl group;

$R^1$ is aryl, heteroaryl or heterocyclo any of which may be optionally independently substituted with one or more $R^{10}$ groups as allowed by valance;

$R^2$ is
(i) H, or
(ii) alkyl, haloalkyl, alkenyl, alkynyl, cycloalkyl, cycloalkenyl, heterocyclo, aryl, heteroaryl, arylalkyl, heteroarylalkyl, cycloalkylalkyl, heterocycloalkyl, —S(O)$_{v*}$R$^4$, —NR$^5$R$^{5a}$, —C(=O)R$^4$, —C(=S)R$^4$, —C(=O)OR$^4$, —C(=S)OR$^4$, —C(=O)NR$^5$R$^{5a}$, —C(=S)NR$^5$R$^{5a}$, —N(R$^5$)C(=O)NR$^5$R$^{5a}$, —N(R$^5$)C(=S)NR$^5$R$^{5a}$, —N(R$^5$)C(=O)R$^4$, —N(R$^5$)C(=S)R$^4$, —SO$_2$NR$^5$R$^{5a}$, —N(R$^5$)SO$_2$R$^4$, —N(R$^5$)SO$_2$NR$^5$R$^{5a}$, —N(R$^5$)C(=O)OR$^4$, —N(R$^5$)C(=S)OR$^4$, —N(R$^5$)SO$_2$R$^4$ any of which may be optionally independently substituted with one or more $R^{10}$ as allowed by valance, $R^{2a}$, $R^{2c}$, $R^{2b*}$ and $R^3$ are independently selected at each occurrence from H, halo, cyano, nitro, alkyl, haloalkyl, alkenyl, alkynyl, cycloalkyl, cycloalkenyl, heterocyclo, aryl, heteroaryl, arylalkyl, heteroarylalkyl, cycloalkylalkyl, heterocycloalkyl, —OR$^4$, —S(O)$_v$R$^4$, —NR$^5$R$^{5a}$, —C(=O)R$^4$, —C(=S)R$^4$, —C(=O)OR$^4$, —C(=S)OR$^4$, —C(=O)NR$^5$R$^{5a}$, —C(=S)NR$^5$R$^{5a}$, —N(R$^5$)C(=O)NR$^5$R$^{5a}$, —N(R$^5$)C(=S)NR$^5$R$^{5a}$, —N(R$^5$)C(=O)R$^4$, —N(R$^5$)C(=S)R$^4$, —OC(=O)NR$^5$R$^{5a}$, —OC(=S)NR$^5$R$^{5a}$, —SO$_2$NR$^5$R$^{5a}$, —N(R$^5$)SO$_2$R$^4$, —N(R$^5$)SO$_2$NR$^5$R$^{5a}$, —N(R$^5$)C(=O)OR$^4$, —N(R$^5$)C(=S)OR$^4$, —N(R$^5$)SO$_2$R$^4$, any of which may be optionally independently substituted with one or more $R^{10}$ groups as allowed by valance;

$R^{2b}$ and $R^{2b+}$ are independently H, alkyl, haloalkyl, alkenyl, alkynyl, cycloalkyl, cycloalkenyl, heterocyclo, aryl, heteroaryl, arylalkyl, heteroarylalkyl, cycloalkylalkyl, heterocycloalkyl, —C(=O)R$^4$, —C(=S)R$^4$, —C(=O)OR$^4$, —C(=S)OR$^4$, —C(=O)NR$^5$R$^{5a}$, or —C(=S)NR$^5$R$^{5a}$;

or $R^{2b}$ and $R^{2b*}$ may optionally combine to form a bond, provided when no such bond is formed $R^{2a}$ is limited to H, alkyl, haloalkyl, alkenyl, alkynyl, cycloalkyl, cycloalkenyl, heterocyclo, aryl, heteroaryl, arylalkyl, heteroarylalkyl, cycloalkylalkyl, heterocycloalkyl, —C(=O)R$^4$, —C(=S)R$^4$, —C(=O)OR$^4$, —C(=S)OR$^4$, —C(=O)NR$^5$R$^{5a}$, and —C(=S)NR$^5$R$^{5a}$;

or $R^{2b}$ and $R^{2b+}$ may optionally combine to form a bond, provided when no such bond is formed $R^{2a}$ is limited to H, alkyl, haloalkyl, alkenyl, alkynyl, cycloalkyl, cycloalkenyl, heterocyclo, aryl, heteroaryl, arylalkyl, heteroarylalkyl, cycloalkylalkyl, heterocycloalkyl, —C(=O)R$^4$, —C(=S)R$^4$, —C(=O)OR$^4$, —C(=S)OR$^4$, —C(=O)NR$^5$R$^{5a}$, and —C(=S)NR$^5$R$^{5a}$;

$R^4$ is independently selected at each occurrence from H, alkyl, haloalkyl, cycloalkyl, alkenyl, alkynyl, aryl, heteroaryl, heterocyclo, arylalkyl, heteroarylalkyl, heterocycloalkyl, and cycloalkylalkyl, any of which may be optionally independently substituted as allowed by valance with one or more $R^{10}$ groups;

$R^5$, and $R^{5a}$ are independently selected at each occurrence from H, alkyl, haloalkyl, cycloalkyl, alkenyl, alkynyl, aryl, heteroaryl, heterocyclo, arylalkyl, heteroarylalkyl, heterocycloalkyl, and cycloalkylalkyl, any of which may be optionally substituted as allowed by valance with one or more $R^{10}$;

or $R^5$ and $R^{5a}$ may combine to form a heterocyclo ring optionally substituted with one or more $R^{10}$;

$R^{10}$ at each occurrence is independently, halo, cyano, nitro, oxo, alkyl, haloalkyl, alkenyl, alkynyl, cycloalkyl, cycloalkenyl, heterocyclo, aryl, heteroaryl, arylalkyl, heteroarylalkyl, cycloalkylalkyl, heterocycloalkyl, -(alkylene)$_m$-OR$^4$, -(alkylene)$_m$-S(O)$_v$R$^4$, -(alkylene)$_m$-NR$^5$R$^{5a}$, -(alkylene)$_m$-C(=O)R$^4$, -(alkylene)$_m$-C(=S)R$^4$, -(alkylene)$_m$-C(=O)OR$^4$, -(alkylene)$_m$-OC(=O)R$^4$, -(alkylene)$_m$-C(=S)OR$^4$, -(alkylene)$_m$-C(=O)NR$^5$R$^{5a}$, -(alkylene)$_m$-C(=S)NR$^5$R$^{5a}$, -(alkylene)$_m$-N(R$^5$)C(=O)NR$^5$R$^{5a}$, -(alkylene)$_m$-N(R$^5$)C(=S)NR$^5$R$^{5a}$, -(alkylene)$_m$-N(R$^5$)C(=O)R$^4$, -(alkylene)$_m$-N(R$^5$)C(=S)R$^4$, -(alkylene)$_m$-OC(=O)NR$^5$R$^{5a}$, -(alkylene)$_m$-OC(=S)NR$^5$R$^{5a}$, -(alkylene)$_m$-SO$_2$NR$^5$R$^{5a}$, -(alkylene)$_m$-N(R$^5$)SO$_2$R$^4$, -(alkylene)$_m$-N(R$^5$)SO$_2$NR$^5$R$^{5a}$, -(alkylene)$_m$-N(R$^5$)C(=O)OR$^4$, -(alkylene)$_m$-N(R$^5$)C(=S)OR$^4$, or -(alkylene)$_m$-N(R$^5$)SO$_2$R$^4$;

wherein said alkyl, haloalkyl, alkenyl, alkynyl, cycloalkyl, cycloalkenyl, heterocyclo, aryl, heteroaryl, arylalkyl, heteroarylalkyl, cycloalkylalkyl, and heterocycloalkyl groups may be further independently substituted with one or more -(alkylene)$_m$-OR$^4$, -(alkylene)$_m$-S(O)$_v$R$^4$, -(alkylene)$_m$-NR$^5$R$^{5a}$, -(alkylene)$_m$-C(=O)R$^4$, -(alkylene)$_m$-C(=S)R$^4$, -(alkylene)$_m$-C(=O)OR$^4$, -(alkylene)$_m$-OC(=O)R$^4$, -(alkylene)$_m$-C(=S)OR$^4$, -(alkylene)$_m$-C(=O)NR$^5$R$^{5a}$, -(alkylene)$_m$-C(=S)NR$^5$R$^{5a}$, -(alkylene)$_m$-N(R$^5$)C(=O)NR$^5$R$^{5a}$, -(alkylene)$_m$-N(R$^5$)C(=S)NR$^5$R$^{5a}$, -(alkylene)$_m$-N(R$^5$)C(=O)R$^4$, -(alkylene)$_m$-N(R$^5$)C(=S)R$^4$, -(alkylene)$_m$-OC(=O)NR$^5$R$^{5a}$, -(alkylene)$_m$-OC(=S)NR$^5$R$^{5a}$, -(alkylene)$_m$-SO$_2$NR$^5$R$^{5a}$, -(alkylene)$_m$-N(R$^5$)SO$_2$R$^4$, -(alkylene)$_m$-N(R$^5$)SO$_2$NR$^5$R$^{5a}$, -(alkylene)$_m$-N(R$^5$)C(=O)OR$^4$, -(alkylene)$_m$-N(R$^5$)C(=S)OR$^4$, or -(alkylene)$_m$-N(R$^5$)SO$_2$R$^4$;

and further wherein any two $R^{10}$ groups attached to the same atom or attached to adjacent atoms may combine to form an optionally substituted 3- to 8 membered ring system;

m is 0 or 1;

n is 0, 1 or 2;

v is 0, 1 or 2;

v* is 1 or 2.

The invention includes compounds wherein $R^1$ is phenyl, naphthyl, benzodioxolyl, benzooxazolyl, benzoisoxazolyl, pyridinyl, pyrimidinyl, pyrazinyl, pyrimidinyl, pyrazidinyl, isoquinolinyl, quinolinyl, quinazolinyl, quinazolinonyl, quinoxalinyl, naphthyridinyl, benzotriazinyl, triazolopyridinyl, triazolopyrimidinyl, triazolopyridazinyl, imidazopyridinyl, imidazopyrimidinyl, imidazopyridazinyl, pyrrolopyridinyl, pyrrolopyrimidinyl, pyrrolopyridazinyl, pyrazolopyridinyl, pyrazolopyrimidinyl, pyrazolopyridazinyl, cinnolinyl, thienopyridinyl, thienopyrimidinyl, thienopyridazinyl, furopyridinyl, furopyrimidinyl, furopyrazinyl, benzofuranyl, benzoimidazolyl, indolyl, benzoisoxazolyl, benzothiazolyl, or benzoisothiazolyl any of which may be optionally independently substituted with one or more $R^{10}$ groups as allowed by valance.

In one aspect, $R^1$ groups include
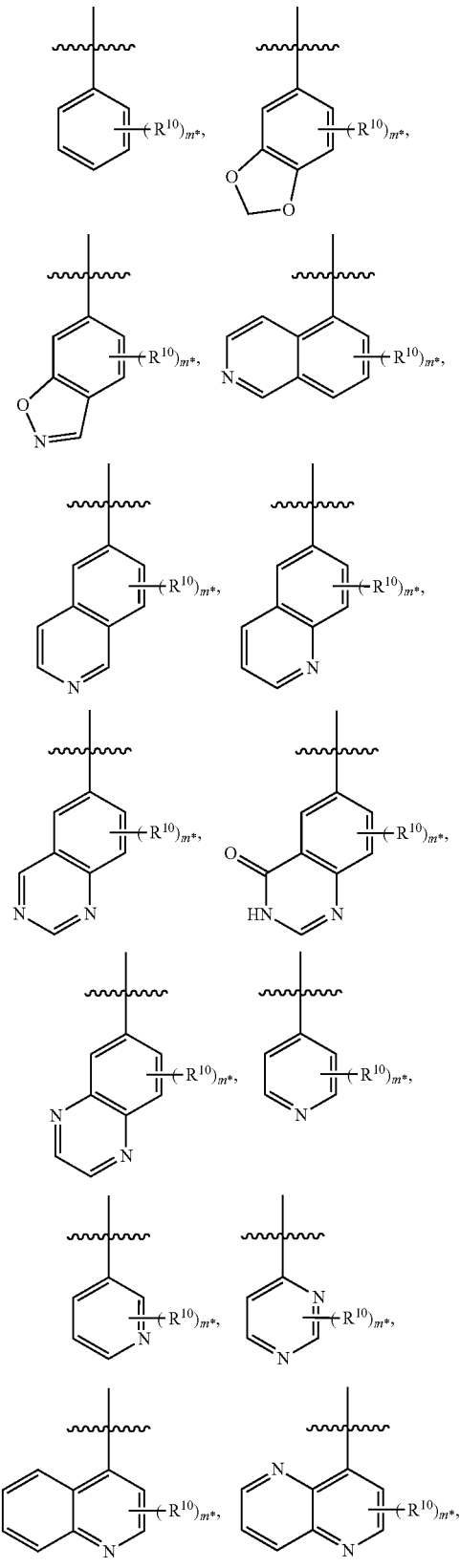
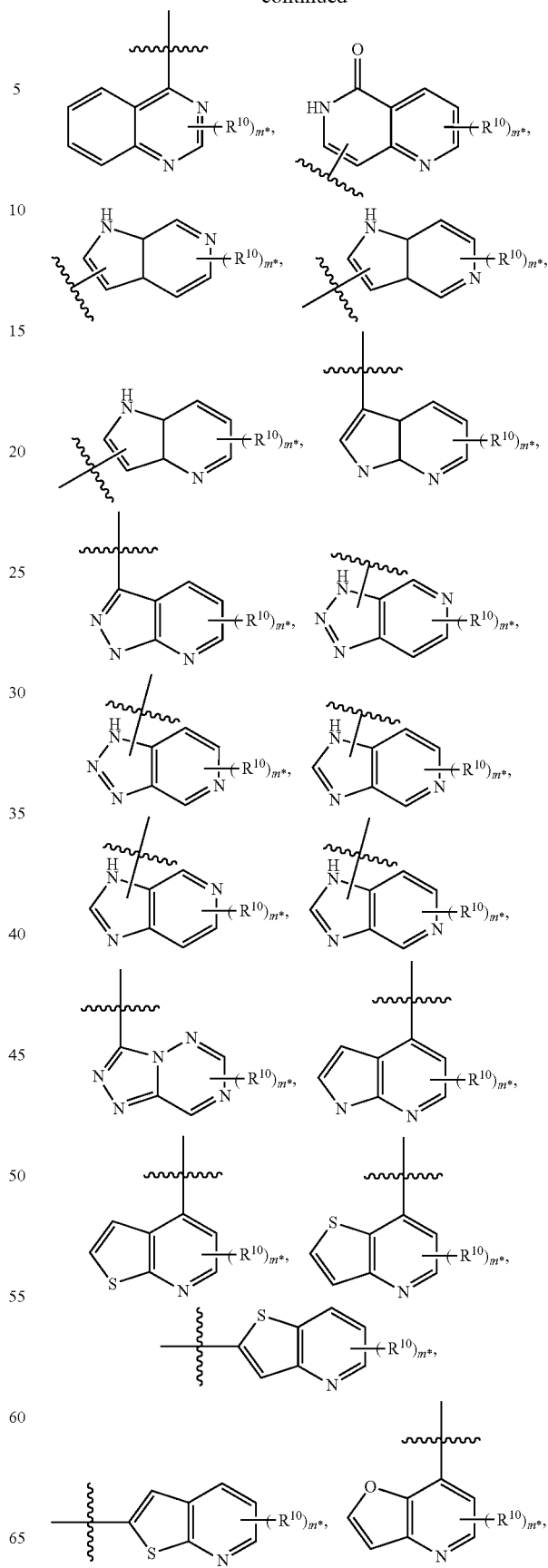

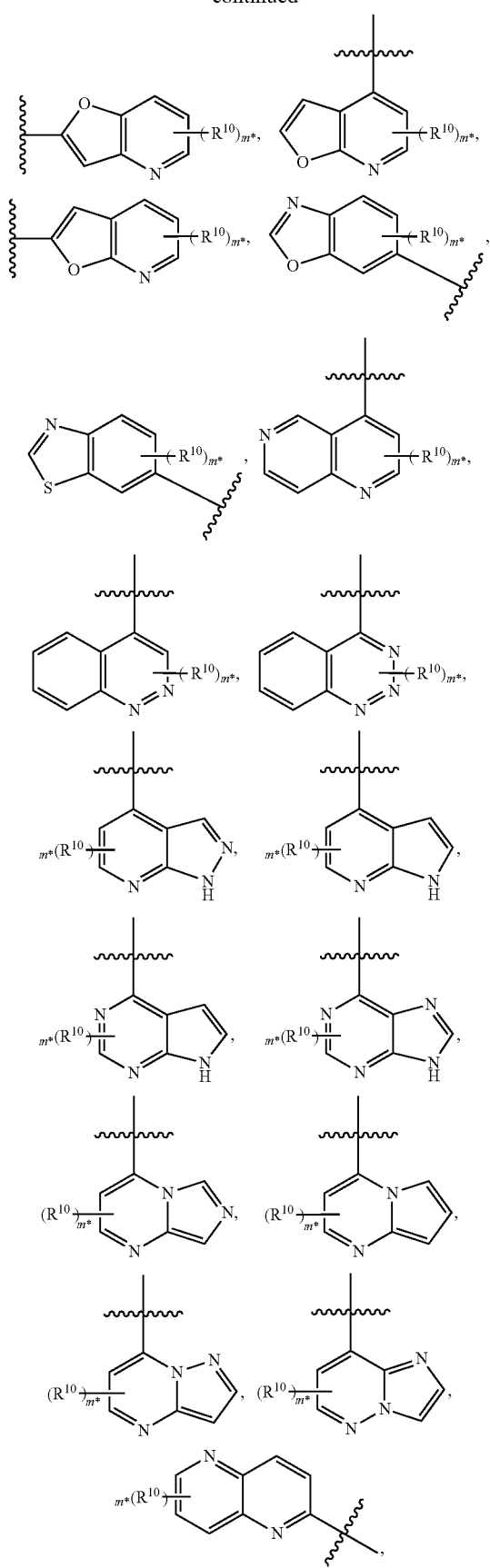
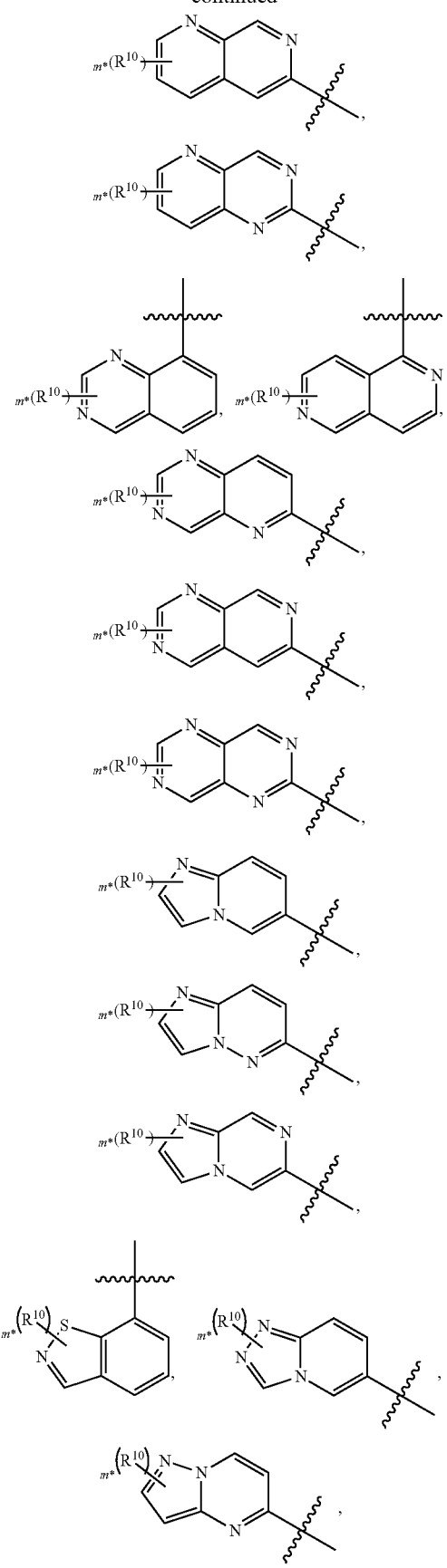

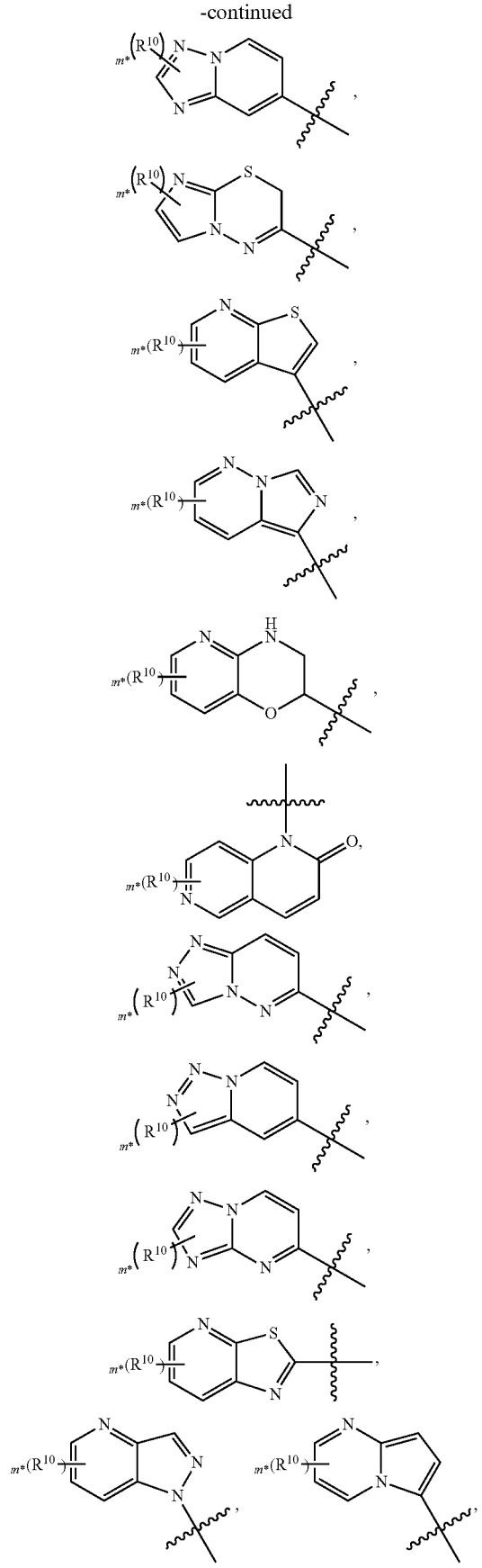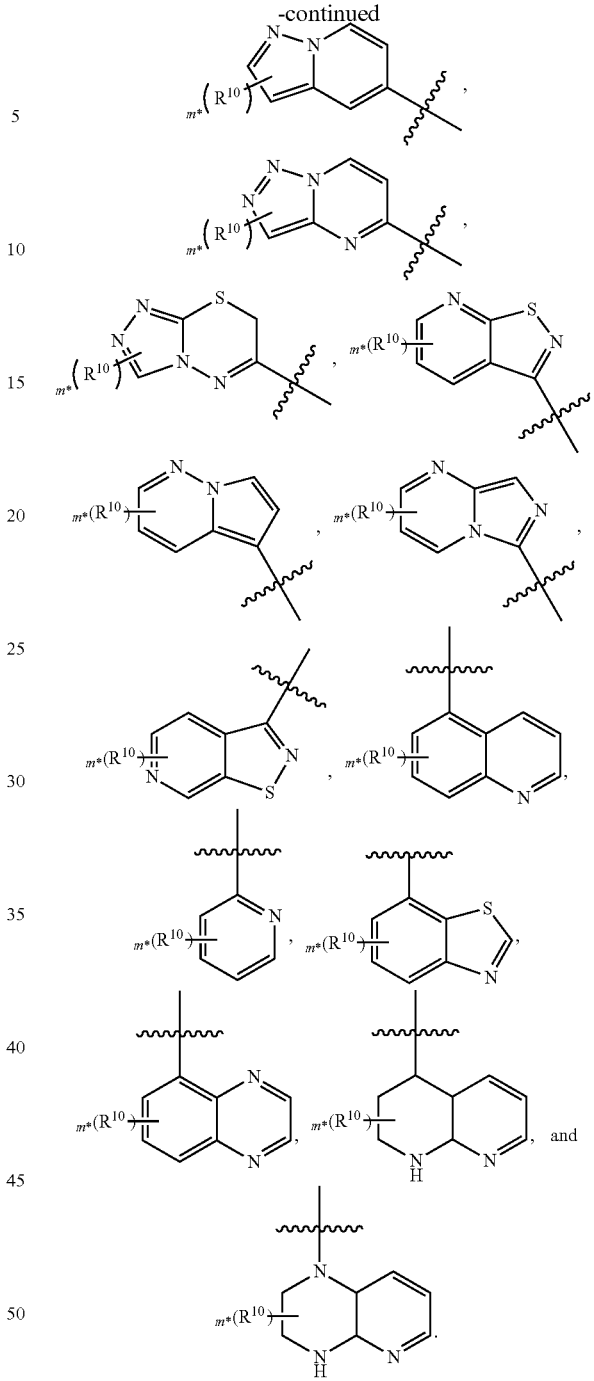

where m* is 0, 1, 2, 3, 4, 5 or 6, as allowed by valence.

In one aspect, $R^1$ groups include moieties that are either unsubstituted or independently substituted as allowed by valance with one or more halo, cyano, nitro, alkyl, alkenyl, alkynyl, haloalkyl, -(alkylene)$_m$-OR$^4$, -(alkylene)$_m$-NR$^5$R$^{5a}$, -(alkylene)$_m$-C(=O)R$^4$, -(alkylene)$_m$-C(=O)OR$^4$, -(alkylene)$_m$-OC(=O)R$^4$, -(alkylene)$_m$-C(=O)NR$^5$R$^{5a}$, -(alkylene)$_m$-N(R$^5$)C(=O)NR$^5$R$^{5a}$, -(alkylene)$_m$-N(R$^5$)C(=O)R$^4$, -(alkylene)$_m$-OC(=O)NR$^5$R$^{5a}$, or -(alkylene)$_m$-N(R$^5$)C(=O)OR$^4$.

The present invention further encompasses compounds wherein $R^2$ is selected from H, alkynyl, —C(=O)NR$^5$R$^{5a}$, phenyl, naphthyl, pyrrolyl, imidazolyl, pyrazolyl, triazolyl, tetrazolyl, furanyl, thienyl, oxazolyl, isoxazolyl, thiazolyl, isothiazolyl, pyridinyl, tetrahydropyridinyl, pyridinonyl, pyrazinyl, pyrimidinyl, pyridazinyl, indolyl, isoindolyl, indolinyl, indolinonyl, isoidolinyl, isoindolinonyl, dihydrobenzofuranyl, dihydroisobenzofuranyl, benzofuranyl, isobenzofuranyl, quinolinyl, isoquinolinyl, quinazolinyl, quinazolinonyl, tetrahydroquinolinyl, tetrahydroisoquinolinyl, dihydroquinolinonyl, dihydroisoquinolinonyl, quinoxalinyl, tetrahydroquinoxalinyl, benzomorpholinyl, dihydrobenzodioxinyl, imidazopyridinyl, naphthyridinyl, benzotriazinyl, triazolopyridinyl, triazolopyrimidinyl, triazolopyridazinyl, imidazopyridinyl, imidazopyrimidinyl, imidazopyridazinyl, pyrrolopyridinyl, pyrrolopyrimidinyl, pyrrolopyridazinyl, pyrazolopyridinyl, pyrazolopyrimidinyl, pyrazolopyridazinyl, cinnolinyl, thienopyrrolyl, tetrahydrothienopyrrolyl, dihydrothienopyrrolonyl, thienopyridinyl, thienopyrimidinyl, thienopyridazinyl, furopyridinyl, furopyrimidinyl, furopyrazidinyl, benzofuranyl, benzoimidazolyl, benzoisoxazolyl, benzothiazolyl, and benzoisothiazolyl any of which may be optionally independently substituted with one or more $R^{10}$ groups as allowed by valance.

In one aspect, $R^2$ groups include (a) alkynyl, or —C(=O)NR$^5$R$^{5a}$, either of which may be optionally independently substituted with one or more $R^{10}$ groups as allowed by valance; or (b) an aryl, heteroaryl or heterocyclo ring system selected from

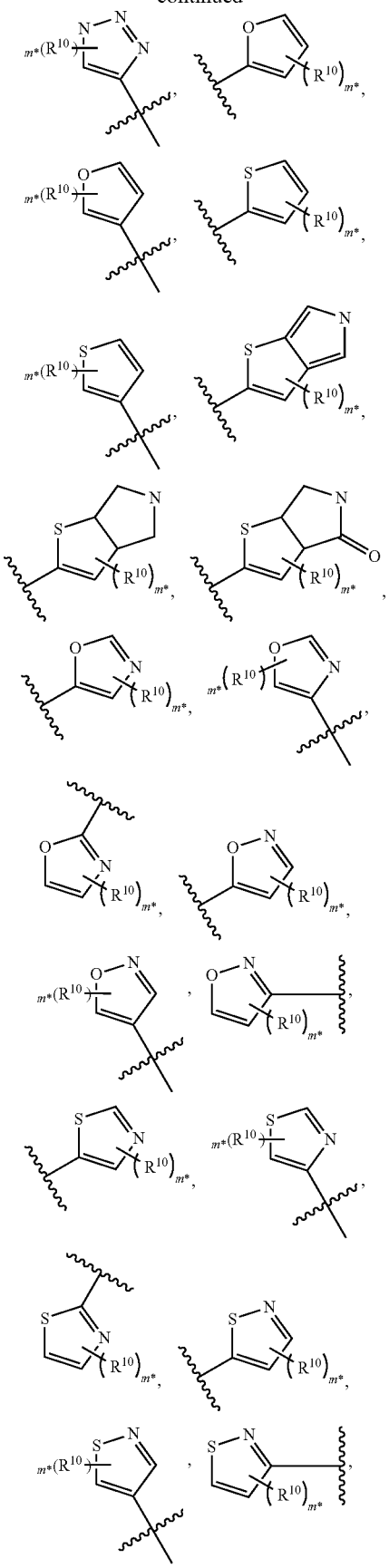

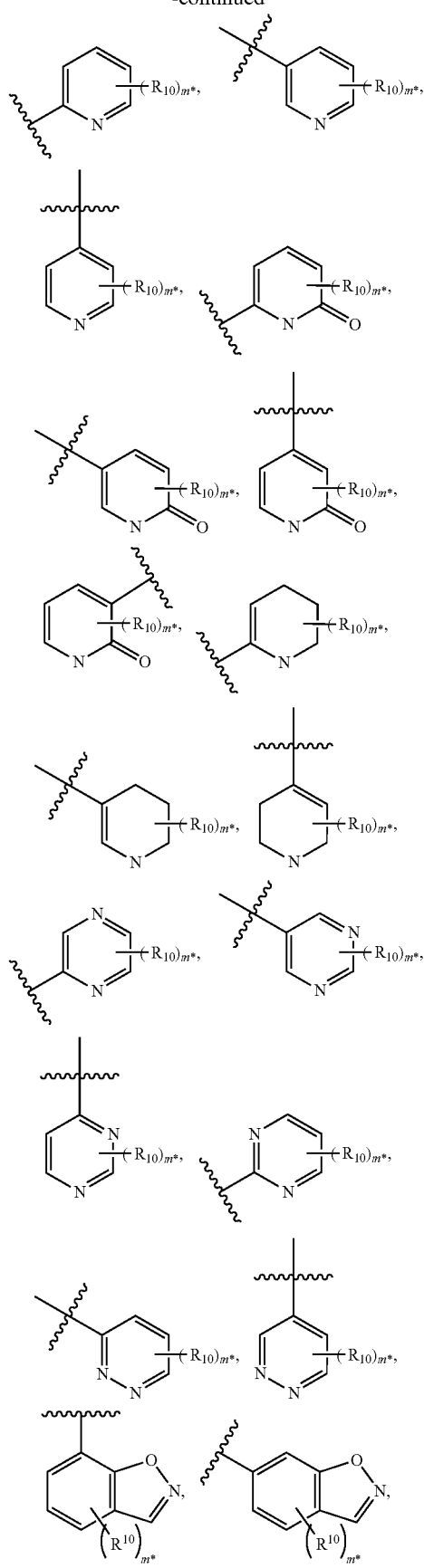
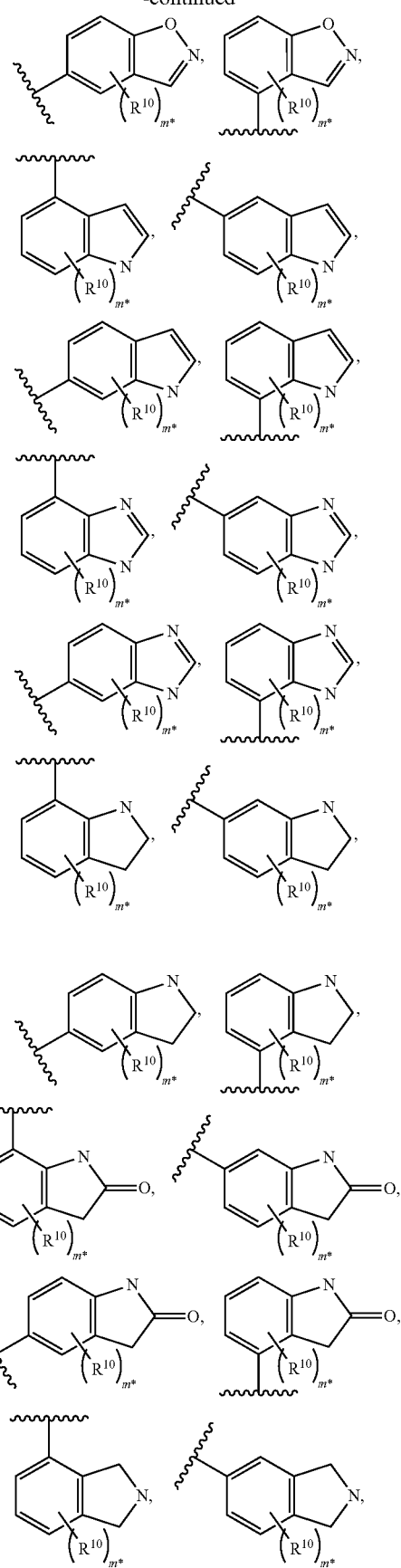

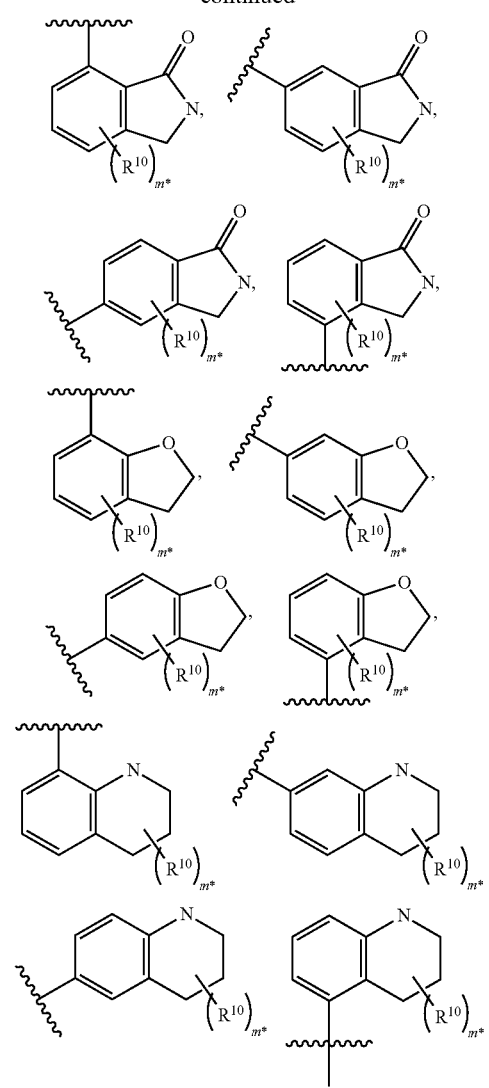
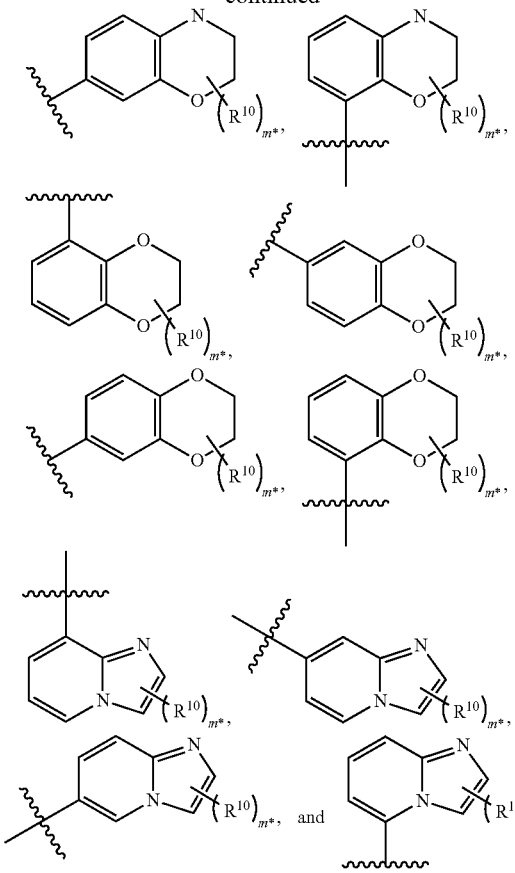
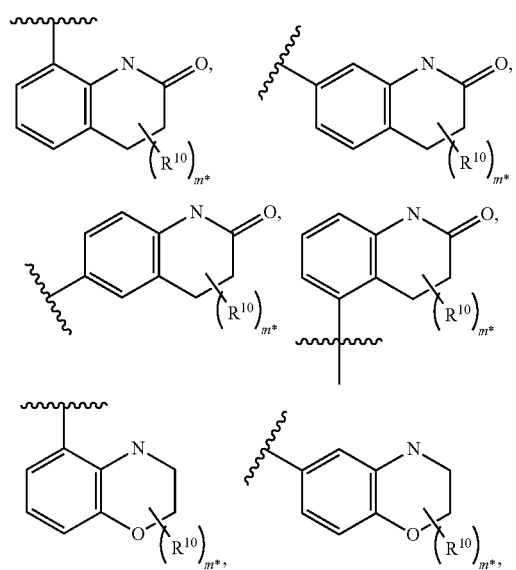

where m* is 0, 1, 2, 3, 4, 5 or 6, as allowed by valence.

Compounds of the present invention include compounds having either or both of $R^1$ groups and $R^2$ groups either alone or in any combination thereof.

The present invention further includes compounds wherein $R^a$, $R^b$, $R^c$ and $R^d$ groups are independently hydrogen, alkyl (especially methyl), and halogen (especially fluorine).

Exemplary compounds within the scope of formula I and II include compounds of the following formulae IA, and IB.

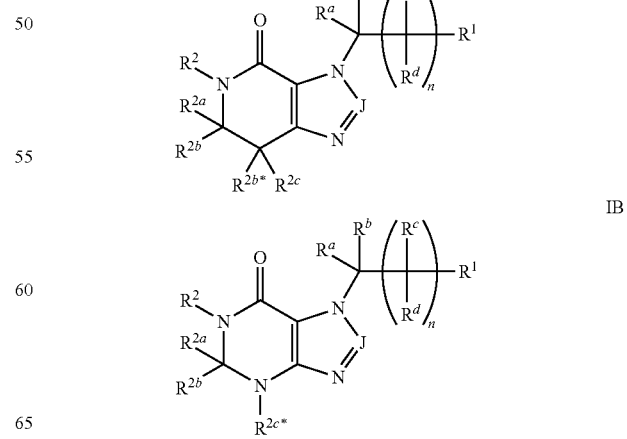

or enantiomers, diastereomers and salts thereof. In one aspect, the invention provides the compounds of formula IA, or enantiomers, diastereomers, and salts thereof, wherein J is N and $R^{2a}$, $R^{2c}$, $R^{2b*}$ are H.

Exemplary compounds within the scope of formula I include compounds of the following formula IC.

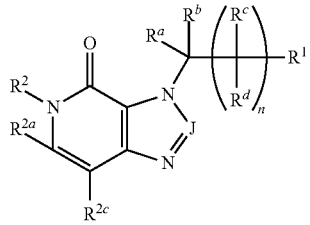

or enantiomers, diastereomers and salts thereof. In one aspect, the invention provides compounds of this formula or enantiomers, diastereomers, and salts thereof, wherein $R^{2a}$ and $R^{2c}$ are H.

The invention also provides compound or enantiomers, diastereomers, and salts thereof, selected from the group consisting of:

5-phenyl-3-(quinolin-6-ylmethyl)-6,7-dihydro-3H-[1,2,3] triazolo[4,5-c]pyridin-4(5H)-one,
5-(3-methylisothiazol-5-yl)-3-(quinolin-6-ylmethyl)-6,7-dihydro-3H-[1,2,3]triazolo[4,5-c]pyridin-4(5H)-one,
5-(3-methylisothiazol-5-yl)-3-(quinolin-6-ylmethyl)-3H-[1,2,3]triazolo[4,5-c]pyridin-4(5H)-one,
(S)-5-(3-methylisothiazol-5-yl)-3-(1-(quinolin-6-yl)ethyl)-6,7-dihydro-3H-[1,2,3]triazolo[4,5-c]pyridin-4(5H)-one,
(R)-5-(3-methylisothiazol-5-yl)-3-(1-(quinolin-6-yl)ethyl)-6,7-dihydro-3H-[1,2,3]triazolo[4,5-c]pyridin-4(5H)-one,
(S)-5-(3-methylisothiazol-5-yl)-3-(1-(quinolin-6-yl)ethyl)-3H-[1,2,3]triazolo[4,5-c]pyridin-4(5H)-one,
(R)-5-(3-methylisothiazol-5-yl)-3-(1-(quinolin-6-yl)ethyl)-3H-[1,2,3]triazolo[4,5-c]pyridin-4(5H)-one,
(S)-5-(1-methyl-1H-pyrazol-4-yl)-3-(1-(quinolin-6-yl)ethyl)-3H-[1,2,3]triazolo[4,5-c]pyridin-4(5H)-one,
(R)-5-(1-methyl-1H-pyrazol-4-yl)-3-(1-(quinolin-6-yl)ethyl)-3H-[1,2,3]triazolo[4,5-c]pyridin-4(5H)-one,
1-(1-(quinolin-6-yl)ethyl)-1H-[1,2,3]triazolo[4,5-c]pyridin-4(5H)-one,
(S)-6-(3-methylisothiazol-5-yl)-1-(1-(quinolin-6-yl)ethyl)-1H-[1,2,3]triazolo[4,5-d]pyrimidin-7(6H)-one,
6-(1-methyl-1H-pyrazol-4-yl)-1-(1-(quinolin-6-yl)ethyl)-1H-[1,2,3]triazolo[4,5-c]pyridin-4(5H)-one,
(S)-5-(1-methyl-1H-pyrazol-4-yl)-3-(1-(quinolin-6-yl)ethyl)-3H-[1,2,3]triazolo[4,5-d]pyrimidin-7(6H)-one,
(S)-3-(1-(3-(2-methoxyethoxy)quinolin-6-yl)ethyl)-5-(3-methylisothiazol-5-yl)-3H-[1,2,3]triazolo[4,5-c]pyridin-4(5H)-one,
(R)-3-(1-(3-(2-methoxyethoxy)quinolin-6-yl)ethyl)-5-(3-methylisothiazol-5-yl)-3H-[1,2,3]triazolo[4,5-c]pyridin-4(5H)-one,
(S)-3-(1-(3-methoxyquinolin-6-yl)ethyl)-5-(3-methylisothiazol-5-yl)-3H-[1,2,3]triazolo[4,5-c]pyridin-4(5H)-one,
(R)-3-(1-(3-methoxyquinolin-6-yl)ethyl)-5-(3-methylisothiazol-5-yl)-3H-[1,2,3]triazolo[4,5-c]pyridin-4(5H)-one,
(S)-5-(3,4-difluorophenyl)-3-(1-(3-(2-methoxyethoxy)quinolin-6-yl)ethyl)-3H-[1,2,3]triazolo[4,5-c]pyridin-4(5H)-one,
(R)-5-(3,4-difluorophenyl)-3-(1-(3-(2-methoxyethoxy)quinolin-6-yl)ethyl)-3H-[1,2,3]triazolo[4,5-c]pyridin-4(5H)-one,
(S)-5-(3,5-difluorophenyl)-3-(1-(3-(2-methoxyethoxy)quinolin-6-yl)ethyl)-3H-[1,2,3]triazolo[4,5-c]pyridin-4(5H)-one,
(R)-5-(3,5-difluorophenyl)-3-(1-(3-(2-methoxyethoxy)quinolin-6-yl)ethyl)-3H-[1,2,3]triazolo[4,5-c]pyridin-4(5H)-one,
3-((3-(2-methoxyethoxy)quinolin-6-yl)methyl)-5-(thiophen-2-yl)-3H-[1,2,3]triazolo[4,5-c]pyridin-4(5H)-one,
5-(3,5-difluorophenyl)-3-((3-(2-methoxyethoxy)quinolin-6-yl)methyl)-3H-[1,2,3]triazolo[4,5-c]pyridin-4(5H)-one,
5-(3,5-difluorophenyl)-3-((3-methoxyquinolin-6-yl)methyl)-3H-[1,2,3]triazolo[4,5-c]pyridin-4(5H)-one,
(S)-3-(1-(3-(2-methoxyethoxy)quinolin-6-yl)ethyl)-5-(thiophen-2-yl)-3H-[1,2,3]triazolo[4,5-c]pyridin-4(5H)-one,
(R)-3-(1-(3-(2-methoxyethoxy)quinolin-6-yl)ethyl)-5-(thiophen-2-yl)-3H-[1,2,3]triazolo[4,5-c]pyridin-4(5H)-one,
3-((3-(2-methoxyethoxy)quinolin-6-yl)methyl)-5-(3-methylisothiazol-5-yl)-3H-[1,2,3]triazolo[4,5-c]pyridin-4(5H)-one,
3-((3-methoxyquinolin-6-yl)methyl)-5-(3-methylisothiazol-5-yl)-3H-[1,2,3]triazolo[4,5-c]pyridin-4(5H)-one,
(S)-5-(4-chloro-3-(trifluoromethyl)phenyl)-3-(1-(quinolin-6-yl)ethyl)-3H-[1,2,3]triazolo[4,5-c]pyridin-4(5H)-one,
(R)-5-(4-chloro-3-(trifluoromethyl)phenyl)-3-(1-(quinolin-6-yl)ethyl)-3H-[1,2,3]triazolo[4,5-c]pyridin-4(5H)-one,
(S)-5-benzyl-3-(1-(quinolin-6-yl)ethyl)-3H-[1,2,3]triazolo[4,5-c]pyridin-4(5H)-one,
(R)-5-benzyl-3-(1-(quinolin-6-yl)ethyl)-3H-[1,2,3]triazolo[4,5-c]pyridin-4(5H)-one,
(S)-5-(5-methylthiophen-2-yl)-3-(1-(quinolin-6-yl)ethyl)-3H-[1,2,3]triazolo[4,5-c]pyridin-4(5H)-one,
(R)-5-(5-methylthiophen-2-yl)-3-(1-(quinolin-6-yl)ethyl)-3H-[1,2,3]triazolo[4,5-c]pyridin-4(5H)-one,
(S)-5-(4-methylthiophen-2-yl)-3-(1-(quinolin-6-yl)ethyl)-3H-[1,2,3]triazolo[4,5-c]pyridin-4(5H)-one, and
(R)-5-(4-methylthiophen-2-yl)-3-(1-(quinolin-6-yl)ethyl)-3H-[1,2,3]triazolo[4,5-c]pyridin-4(5H)-one.

The invention also relates to pharmaceutical compositions containing the above compounds, together with a pharmaceutically acceptable vehicle or carrier.

Indications

The invention also relates to a method of treating cancer in a subject using the above compounds. In one aspect, the invention also relates to a method of reducing tumor size in a subject using the above compounds. In a further aspect, the invention also relates to a method of reducing metastasis in a tumor in a subject, using the above compounds.

The invention also relates to a method of treating HGF-mediated disorders in a subject using the above compounds.

Compounds of the present invention would be useful for, but not limited to, the prevention or treatment of angiogenesis related diseases. The compounds of the invention have c-Met inhibitory activity. The compounds of the invention are useful in therapy as antineoplasia agents or to minimize deleterious effects of HGF.

Compounds of the invention would be useful for the treatment of neoplasia including cancer and metastasis, including, but not limited to: carcinoma such as cancer of the bladder, breast, colon, kidney, liver, lung (including small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g. soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma).

In one aspect, the compounds are useful for the treatment of neoplasia selected from lung cancer, colon cancer and breast cancer.

The compounds also would be useful for treatment of ophthalmological conditions such as corneal graft rejection, ocular neovascularization, retinal neovascularization including neovascularization following injury or infection, diabetic retinopathy, retrolental fibroplasia and neovascular glaucoma; retinal ischemia; vitreous hemorrhage; ulcerative diseases such as gastric ulcer; pathological, but non-malignant, conditions such as hemangiomas, including infantile hemaginomas, angiofibroma of the nasopharynx and avascular necrosis of bone; and disorders of the female reproductive system such as endometriosis. The compounds are also useful for the treatment of edema, and conditions of vascular hyperpermeability.

The compounds of the invention are useful in therapy of proliferative diseases. These compounds can be used for the treatment of an inflammatory rheumatoid or rheumatic disease, especially of manifestations at the locomotor apparatus, such as various inflammatory rheumatoid diseases, especially chronic polyarthritis including rheumatoid arthritis, juvenile arthritis or psoriasis arthropathy; paraneoplastic syndrome or tumor-induced inflammatory diseases, turbid effusions, collagenosis, such as systemic Lupus erythematosus, poly-myositis, dermato-myositis, systemic sclerodermia or mixed collagenosis; postinfectious arthritis (where no living pathogenic organism can be found at or in the affected part of the body), seronegative spondylarthritis, such as spondylitis ankylosans; vasculitis, sarcoidosis, or arthrosis; or further any combinations thereof. An example of an inflammation related disorder is (a) synovial inflammation, for example, synovitis, including any of the particular forms of synovitis, in particular bursal synovitis and purulent synovitis, as far as it is not crystal-induced. Such synovial inflammation may for example, be consequential to or associated with disease, e.g. arthritis, e.g. osteoarthritis, rheumatoid arthritis or arthritis deformans. The present invention is further applicable to the systemic treatment of inflammation, e.g. inflammatory diseases or conditions, of the joints or locomotor apparatus in the region of the tendon insertions and tendon sheaths. Such inflammation may be, for example, consequential to or associated with disease or further (in a broader sense of the invention) with surgical intervention, including, in particular conditions such as insertion endopathy, myofasciale syndrome and tendomyosis. The present invention is further especially applicable to the treatment of inflammation, e.g. inflammatory disease or condition, of connective tissues including dermatomyositis and myositis.

These compounds can be used as active agents against such disease states as arthritis, atherosclerosis, psoriasis, hemangiomas, myocardial angiogenesis, coronary and cerebral collaterals, ischemic limb angiogenesis, wound healing, peptic ulcer Helicobacter related diseases, fractures, cat scratch fever, rubeosis, neovascular glaucoma and retinopathies such as those associated with diabetic retinopathy or macular degeneration. In addition, some of these compounds can be used as active agents against solid tumors, malignant ascites, hematopoietic cancers and hyperproliferative disorders such as thyroid hyperplasia (especially Grave's disease), and cysts (such as hypervascularity of ovarian stroma, characteristic of polycystic ovarian syndrome (Stein-Leventhal syndrome)) since such diseases require a proliferation of blood vessel cells for growth and/or metastasis.

Further, some of these compounds can be used as active agents against burns, chronic lung disease, stroke, polyps, anaphylaxis, chronic and allergic inflammation, ovarian hyperstimulation syndrome, brain tumor-associated cerebral edema, high-altitude, trauma or hypoxia induced cerebral or pulmonary edema, ocular and macular edema, ascites, and other diseases where vascular hyperpermeability, effusions, exudates, protein extravasation, or edema is a manifestation of the disease. The compounds will also be useful in treating disorders in which protein extravasation leads to the deposition of fibrin and extracellular matrix, promoting stromal proliferation (e.g. fibrosis, cirrhosis and carpal tunnel syndrome).

The compounds of the present invention are also useful in the treatment of ulcers including bacterial, fungal, Mooren ulcers and ulcerative colitis.

The compounds of the present invention are also useful in the treatment of conditions wherein undesired angiogenesis, edema, or stromal deposition occurs in viral infections such as Herpes simplex, Herpes Zoster, AIDS, Kaposi's sarcoma, protozoan infections and toxoplasmosis, following trauma, radiation, stroke, endometriosis, ovarian hyperstimulation syndrome, systemic lupus, sarcoidosis, synovitis, Crohn's disease, sickle cell anemia, Lyme disease, pemphigoid, Paget's disease, hyperviscosity syndrome, Osler-Weber-Rendu disease, chronic inflammation, chronic occlusive pulmonary disease, asthma, and inflammatory rheumatoid or rheumatic disease. The compounds are also useful in the reduction of subcutaneous fat and for the treatment of obesity.

The compounds of the present invention are also useful in the treatment of ocular conditions such as ocular and macular edema, ocular neovascular disease, scleritis, radial keratotomy, uveitis, vitritis, myopia, optic pits, chronic retinal detachment, post-laser complications, glaucoma, conjunctivitis, Stargardt's disease and Eales disease in addition to retinopathy and macular degeneration.

The compounds of the present invention are also useful in the treatment of cardiovascular conditions such as atherosclerosis, restenosis, arteriosclerosis, vascular occlusion and carotid obstructive disease.

The compounds of the present invention are also useful in the treatment of cancer related indications such as solid tumors, sarcomas (especially Ewing's sarcoma and osteosarcoma), retinoblastoma, rhabdomyosarcomas, neuroblastoma, hematopoietic malignancies, including leukemia and lymphoma, tumor-induced pleural or pericardial effusions, and malignant ascites.

The compounds of the present invention are also useful in the treatment of diabetic conditions such as diabetic retinopathy and microangiopathy.

The compounds of the present invention are also useful in the reduction of blood flow in a tumor in a subject.

The compounds of the present invention are also useful in the reduction of metastasis of a tumor in a subject.

The compounds of this invention may also act as inhibitors of other protein kinases, e.g. tie-2, lck, src, fgf, c-Met, ron, ckit and ret, and thus be effective in the treatment of diseases associated with other protein kinases.

Besides being useful for human treatment, these compounds are also useful for veterinary treatment of companion animals, exotic animals and farm animals, including mammals, rodents, and the like. Exemplary animals include horses, dogs, and cats.

As used herein, the compounds of the present invention include the pharmaceutically acceptable derivatives thereof.

Where the plural form is used for compounds, salts, and the like, this is taken to mean also a single compound, salt and the like.

Definitions

"Angiogenesis" is defined as any alteration of an existing vascular bed or the formation of new vasculature, which benefits tissue perfusion. This includes the formation of new vessels by sprouting of endothelial cells from existing blood vessels or the remodeling of existing vessels to alter size, maturity, direction or flow properties to improve blood perfusion of tissue.

As used herein, "HGF" refers to hepatocyte growth factor/scatter factor. This includes purified hepatocyte growth factor/scatter factor, fragments of hepatocyte growth factor/scatter factor, chemically synthesized fragments of hepatocyte growth factor/scatter factor, derivatives or mutated versions of hepatocyte growth factor/scatter factor, and fusion proteins comprising hepatocyte growth factor/scatter factor and another protein. "HGF" as used herein also includes hepatocyte growth factor/scatter factor isolated from species other than humans.

As used herein "c-Met" refers to the receptor for HGF. This includes purified receptor, fragments of receptor, chemically synthesized fragments of receptor, derivatives or mutated versions of receptor, and fusion proteins comprising the receptor and another protein. "c-Met" as used herein also includes the HGF receptor isolated from a species other than humans.

As used herein, "HGF" refers to hepatocyte growth factor/scatter factor. This includes purified hepatocyte growth factor/scatter factor, fragments of hepatocyte growth factor/scatter factor, chemically synthesized fragments of hepatocyte growth factor/scatter factor, derivatives or mutated versions of hepatocyte growth factor/scatter factor, and fusion proteins comprising hepatocyte growth factor/scatter factor and another protein. "HGF" as used herein also includes hepatocyte growth factor/scatter factor isolated from species other than humans.

As used herein "c-Met" refers to the receptor for HGF. This includes purified receptor, fragments of receptor, chemically synthesized fragments of receptor, derivatives or mutated versions of receptor, and fusion proteins comprising the receptor and another protein. "c-Met" as used herein also includes the HGF receptor isolated from a species other than humans.

As used herein, the terms "hepatocyte growth factor" and "HGF" refer to a growth factor typically having a structure with six domains (finger, Kringle 1, Kringle 2, Kringle 3, Kringle 4 and serine protease domains). Fragments of HGF constitute HGF with fewer domains and variants of HGF may have some of the domains of HGF repeated; both are included if they still retain their respective ability to bind a HGF receptor. The terms "hepatocyte growth factor" and "HGF" include hepatocyte growth factor from humans ("huHGF") and any non-human mammalian species, and in particular rat HGF. The terms as used herein include mature, pre, pre-pro, and pro forms, purified from a natural source, chemically synthesized or recombinantly produced. Human HGF is encoded by the cDNA sequence published by Miyazawa et al. (1989), supra, or Nakamura et al. (1989), supra. The sequences reported by Miyazawa et al. and Nakamura et al. differ in 14 amino acids. The reason for the differences is not entirely clear; polymorphism or cloning artifacts are among the possibilities. Both sequences are specifically encompassed by the foregoing terms. It will be understood that natural allelic variations exist and can occur among individuals, as demonstrated by one or more amino acid differences in the amino acid sequence of each individual. The terms "hepatocyte growth factor" and "HGF" specifically include the delta 5 huHGF as disclosed by Seki et al., supra.

The terms "HGF receptor" and "c-Met" when used herein refer to a cellular receptor for HGF, which typically includes an extracellular domain, a transmembrane domain and an intracellular domain, as well as variants and fragments thereof which retain the ability to bind HGF. The terms "HGF receptor" and "c-Met" include the polypeptide molecule that comprises the full-length, native amino acid sequence encoded by the gene variously known as p190.sup.MET. The present definition specifically encompasses soluble forms of HGF receptor, and HGF receptor from natural sources, synthetically produced in vitro or obtained by genetic manipulation including methods of recombinant DNA technology. The HGF receptor variants or fragments preferably share at least about 65% sequence homology, and more preferably at least about 75% sequence homology with any domain of the human c-Met amino acid sequence published in Rodrigues et al., Mol. Cell. Biol., 11:2962-2970 (1991); Park et al., Proc. Natl. Acad. Sci., 84:6379-6383 (1987); or Ponzetto et al., Oncogene, 6:553-559 (1991).

The terms "agonist" and "agonistic" when used herein refer to or describe a molecule which is capable of, directly or indirectly, substantially inducing, promoting or enhancing HGF biological activity or HGF receptor activation.

The terms "cancer" and "cancerous" when used herein refer to or describe the physiological condition in mammals that is typically characterized by unregulated cell growth. Examples of cancer include but are not limited to, carcinoma, lymphoma, sarcoma, blastoma and leukemia. More particular examples of such cancers include squamous cell carcinoma, lung cancer, pancreatic cancer, cervical cancer, bladder cancer, hepatoma, breast cancer, colon carcinoma, and head and neck cancer. While the term "cancer" as used herein is not limited to any one specific form of the disease, it is believed that the methods of the invention will be particularly effective for cancers which are found to be accompanied by increased levels of HGF or expression of c-Met in the mammal.

The terms "treating," "treatment," and "therapy" as used herein refer to curative therapy, prophylactic therapy, and preventative therapy.

The term "mammal" as used herein refers to any mammal classified as a mammal, including humans, cows, horses, dogs and cats. In one aspect of the invention, the mammal is a human.

Given that elevated levels of c-Met and HGF are observed in hypertension, arteriosclerosis, myocardial infarction, and rheumatoid arthritis, nucleic acid ligands will serve as useful therapeutic agents for these diseases.

The term "treatment" includes therapeutic treatment as well as prophylactic treatment (either preventing the onset of disorders altogether or delaying the onset of a pre-clinically evident stage of disorders in individuals).

A "pharmaceutically-acceptable derivative" denotes any salt, ester of a compound of this invention, or any other compound which upon administration to a patient is capable of providing (directly or indirectly) a compound of this invention, or a metabolite or residue thereof, characterized by the ability to inhibit angiogenesis.

The phrase "therapeutically-effective" is intended to qualify the amount of each agent, which will achieve the goal of improvement in disorder severity and the frequency of incidence over treatment of each agent by itself, while avoiding adverse side effects typically associated with alternative therapies. For example, effective neoplastic therapeutic agents prolong the survivability of the patient, inhibit the rapidly proliferating cell growth associated with the neoplasm, or effect a regression of the neoplasm.

The term "H" denotes a single hydrogen atom. This radical may be attached, for example, to an oxygen atom to form a hydroxyl radical.

Where the term "alkyl" is used, either alone or within other terms such as "haloalkyl" and "alkylamino", it embraces linear or branched radicals having one to about twelve carbon atoms. Some alkyl radicals are "lower alkyl" radicals having one to about six carbon atoms. Examples of such radicals include methyl, ethyl, n-propyl, isopropyl, n-butyl, isobutyl, sec-butyl, tert-butyl, pentyl, isoamyl, hexyl and the like. The term "alkylenyl" embraces bridging divalent alkyl radicals such as methylenyl and ethylenyl. The term "lower alkyl substituted with $R^2$" does not include an acetal moiety.

The term "alkenyl" embraces linear or branched radicals having at least one carbon-carbon double bond of two to about twelve carbon atoms. In one aspect, alkenyl radicals are "lower alkenyl" radicals having two to about six carbon atoms. In a further aspect, lower alkenyl radicals are radicals having two to about four carbon atoms. Examples of alkenyl radicals include ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations.

The term "alkynyl" denotes linear or branched radicals having at least one carbon-carbon triple bond and having two to about twelve carbon atoms. In one aspect, alkynyl radicals are "lower alkynyl" radicals having two to about six carbon atoms. In a further aspect, they are lower alkynyl radicals having two to about four carbon atoms. Examples of such radicals include propargyl, butynyl, and the like.

Alkyl, alkylenyl, alkenyl, and alkynyl radicals may be optionally substituted with one or more functional groups such as halo, hydroxy, nitro, amino, cyano, haloalkyl, aryl, heteroaryl, heterocyclo and the like.

The term "halo" means halogens such as fluorine, chlorine, bromine or iodine atoms.

The term "haloalkyl" embraces radicals wherein any one or more of the alkyl carbon atoms is substituted with halo as defined above. Specifically embraced are monohaloalkyl, dihaloalkyl and polyhaloalkyl radicals including perhaloalkyl. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1-6 carbon atoms. In one aspect, they are lower haloalkyl radicals having one to three carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means alkyl radicals having all hydrogen atoms replaced with fluoro atoms. Examples include trifluoromethyl and pentafluoroethyl.

The term "hydroxyalkyl" embraces linear or branched alkyl radicals having one to about ten carbon atoms any one of which may be substituted with one or more hydroxyl radicals. In one aspect, hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. Other examples include lower hydroxyalkyl radicals having one to three carbon atoms.

The term "alkoxy" embraces linear or branched oxy-containing radicals each having alkyl portions of one to about ten carbon atoms. In one aspect, alkoxy radicals are "lower alkoxy" radicals having one to six carbon atoms. Examples of such radicals include methoxy, ethoxy, propoxy, butoxy and tert-butoxy. In a further aspect, these radicals are lower alkoxy radicals having one to three carbon atoms. Alkoxy radicals may be further substituted with one or more halo atoms, such as fluoro, chloro or bromo, to provide "haloalkoxy" radicals. Other examples are lower haloalkoxy radicals having one to three carbon atoms. Examples of such radicals include fluoromethoxy, chloromethoxy, trifluoromethoxy, trifluoroethoxy, fluoroethoxy and fluoropropoxy.

The term "aryl", alone or in combination, means a carbocyclic aromatic system containing one or two rings wherein such rings may be attached together in a fused manner. The term "aryl" embraces aromatic radicals such as phenyl, naphthyl, indenyl, tetrahydronaphthyl, and indanyl. I none aspect, aryl is phenyl. The "aryl" group may have 1 or more substituents such as lower alkyl, hydroxyl, halo, haloalkyl, nitro, cyano, alkoxy, lower alkylamino, and the like. Phenyl substituted with —O—$CH_2$—O— forms the aryl benzodioxolyl substituent.

The term "heterocyclyl" (or "heterocyclo") embraces saturated, and partially saturated and heteroatom-containing ring radicals, where the heteroatoms may be selected from nitrogen, sulfur and oxygen. It does not include rings containing —O—O—, —O—S— or —S—S— portions. Said "heterocyclyl" group may have 1 to 3 substituents such as hydroxyl, Boc, halo, haloalkyl, cyano, lower alkyl, lower aralkyl, oxo, lower alkoxy, amino, lower alkylamino, and the like.

Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl, dihydrothiazolyl, and the like.

Particular examples of partially saturated and saturated heterocyclyl include pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydrobenzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1$\lambda$' benzo[d]isothiazol-6-yl, dihydropyranyl, dihydrofuryl and dihydrothiazolyl, and the like.

The term heterocyclyl, (or heterocyclo) also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydrobenzo[1,4]dioxinyl and dihydrobenzofuryl].

The term "heteroaryl" denotes aryl ring systems that contain one or more heteroatoms selected from the group O, N and S, wherein the ring nitrogen and sulfur atom(s) are optionally oxidized, and nitrogen atom(s) are optionally quarternized. Examples include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The term "sulfonyl", whether used alone or linked to other terms such as alkylsulfonyl, denotes respectively divalent radicals —SO$_2$—.

The terms "sulfamyl," "aminosulfonyl" and "sulfonamidyl," denotes a sulfonyl radical substituted with an amine radical, forming a sulfonamide (—SO$_2$NH$_2$).

The term "alkylaminosulfonyl" includes "N-alkylaminosulfonyl" where sulfamyl radicals are independently substituted with one or two alkyl radical(s). In one aspect, alkylaminosulfonyl radicals are "lower alkylaminosulfonyl" radicals having one to six carbon atoms. They also include lower alkylaminosulfonyl radicals having one to three carbon atoms. Examples of such lower alkylaminosulfonyl radicals include N-methylaminosulfonyl, and N-ethylaminosulfonyl.

The terms "carboxy" or "carboxyl", whether used alone or with other terms, such as "carboxyalkyl", denotes —CO$_2$H.

The term "carbonyl", whether used alone or with other terms, such as "aminocarbonyl", denotes —(C=O)—.

The term "aminocarbonyl" denotes an amide group of the formula —C(=O)NH$_2$.

The terms "N-alkylaminocarbonyl" and "N,N-dialkylaminocarbonyl" denote aminocarbonyl radicals independently substituted with one or two alkyl radicals, respectively. In one example, these radicals are "lower alkylaminocarbonyl" having lower alkyl radicals as described above attached to an aminocarbonyl radical.

The terms "N-arylaminocarbonyl" and "N-alkyl-N-arylaminocarbonyl" denote aminocarbonyl radicals substituted, respectively, with one aryl radical, or one alkyl and one aryl radical.

The terms "heterocyclylalkylenyl" and "heterocyclylalkyl" embrace heterocyclic-substituted alkyl radicals. Examples include heterocyclylalkyl radicals are "5- or 6-membered heteroarylalkyl" radicals having alkyl portions of one to six carbon atoms and a 5- or 6-membered heteroaryl radical. Other examples include lower heteroarylalkylenyl radicals having alkyl portions of one to three carbon atoms. Examples include such radicals as pyridylmethyl and thienylmethyl.

The term "aralkyl" embraces aryl-substituted alkyl radicals. Some aralkyl radicals are "lower aralkyl" radicals having aryl radicals attached to alkyl radicals having one to six carbon atoms. Others are "phenylalkylenyl" attached to alkyl portions having one to three carbon atoms. Examples of such radicals include benzyl, diphenylmethyl and phenylethyl. The aryl in said aralkyl may be additionally substituted with halo, alkyl, alkoxy, halkoalkyl and haloalkoxy.

The term "alkylthio" embraces radicals containing a linear or branched alkyl radical, of one to ten carbon atoms, attached to a divalent sulfur atom. In one example, they are lower alkylthio radicals having one to three carbon atoms. An example of "alkylthio" is methylthio, (CH$_3$S—).

The term "haloalkylthio" embraces radicals containing a haloalkyl radical, of one to ten carbon atoms, attached to a divalent sulfur atom. In one aspect, they are lower haloalkylthio radicals having one to three carbon atoms. An example of "haloalkylthio" is trifluoromethylthio.

The term "alkylamino" embraces "N-alkylamino" and "N,N-dialkylamino" where amino groups are independently substituted with one alkyl radical and with two alkyl radicals, respectively. In one aspect, alkylamino radicals are "lower alkylamino" radicals having one or two alkyl radicals of one to six carbon atoms, attached to a nitrogen atom. In one aspect, they are lower alkylamino radicals having one to three carbon atoms. Suitable alkylamino radicals may be mono or dialkylamino such as N-methylamino, N-ethylamino, N,N-dimethylamino, N,N-diethylamino and the like.

The term "arylamino" denotes amino groups, which have been substituted with one or two aryl radicals, such as N-phenylamino. The arylamino radicals may be further substituted on the aryl ring portion of the radical.

The term "heteroarylamino" denotes amino groups, which have been substituted with one or two heteroaryl radicals, such as N-thienylamino. The "heteroarylamino" radicals may be further substituted on the heteroaryl ring portion of the radical.

The term "aralkylamino" denotes amino groups, which have been substituted with one or two aralkyl radicals. For example, they include phenyl-C$_1$-C$_3$-alkylamino radicals, such as N-benzylamino. The aralkylamino radicals may be further substituted on the aryl ring portion.

The terms "N-alkyl-N-arylamino" and "N-aralkyl-N-alkylamino" denote amino groups, which have been independently substituted with one aralkyl and one alkyl radical, or one aryl and one alkyl radical, respectively, to an amino group.

The term "aminoalkyl" embraces linear or branched alkyl radicals having one to about ten carbon atoms any one of which may be substituted with one or more amino radicals. In one aspect, aminoalkyl radicals are "lower aminoalkyl" radicals having one to six carbon atoms and one or more amino radicals. Examples of such radicals include aminomethyl, aminoethyl, aminopropyl, aminobutyl and aminohexyl. Examples also include lower aminoalkyl radicals having one to three carbon atoms.

The term "alkylaminoalkyl" embraces alkyl radicals substituted with alkylamino radicals. IN one aspect, alkylaminoalkyl radicals are "lower alkylaminoalkyl" radicals having alkyl radicals of one to six carbon atoms. In another aspect, they are lower alkylaminoalkyl radicals having alkyl radicals of one to three carbon atoms. Suitable alkylaminoalkyl radicals may be mono or dialkyl substituted, such as N-methylaminomethyl, N,N-dimethyl-aminoethyl, N,N-diethylaminomethyl and the like.

The term "alkylaminoalkoxy" embraces alkoxy radicals substituted with alkylamino radicals. In one aspect, alkylaminoalkoxy radicals are "lower alkylaminoalkoxy" radicals having alkoxy radicals of one to six carbon atoms. Examples include lower alkylaminoalkoxy radicals having alkyl radicals of one to three carbon atoms. Suitable alkylaminoalkoxy radicals may be mono or dialkyl substituted, such as N-methylaminoethoxy, N,N-dimethylaminoethoxy, N,N-diethylaminoethoxy and the like.

The term "alkylaminoalkoxyalkoxy" embraces alkoxy radicals substituted with alkylaminoalkoxy radicals. In one aspect, alkylaminoalkoxyalkoxy radicals are "lower alkylaminoalkoxyalkoxy" radicals having alkoxy radicals of one to six carbon atoms. Examples include lower alkylaminoalkoxyalkoxy radicals having alkyl radicals of one to three carbon atoms. Suitable alkylaminoalkoxyalkoxy radicals may be mono or dialkyl substituted, such as N-methylaminomethoxyethoxy, N-methylaminoethoxyethoxy, N,N-dimethylaminoethoxyethoxy, N,N-diethylaminomethoxymethoxy and the like.

The term "carboxyalkyl" embraces linear or branched alkyl radicals having one to about ten carbon atoms any one of which may be substituted with one or more carboxy radicals. In one aspect, carboxyalkyl radicals are "lower carboxyalkyl" radicals having one to six carbon atoms and one carboxy radical. Examples of such radicals include carboxymethyl, carboxypropyl, and the like. Examples also include lower carboxyalkyl radicals having one to three $CH_2$ groups.

The term "halosulfonyl" embraces sulfonyl radicals substituted with a halogen radical. Examples of such halosulfonyl radicals include chlorosulfonyl and fluorosulfonyl.

The term "arylthio" embraces aryl radicals of six to ten carbon atoms, attached to a divalent sulfur atom. An example of "arylthio" is phenylthio.

The term "aralkylthio" embraces aralkyl radicals as described above, attached to a divalent sulfur atom. In one aspect, they are phenyl-$C_1$-$C_3$-alkylthio radicals. An example of "aralkylthio" is benzylthio.

The term "aryloxy" embraces optionally substituted aryl radicals, as defined above, attached to an oxygen atom. Examples of such radicals include phenoxy.

The term "aralkoxy" embraces oxy-containing aralkyl radicals attached through an oxygen atom to other radicals. In one aspect, aralkoxy radicals are "lower aralkoxy" radicals having optionally substituted phenyl radicals attached to lower alkoxy radical as described above.

The term "heteroaryloxy" embraces optionally substituted heteroaryl radicals, as defined above, attached to an oxygen atom.

The term "heteroarylalkoxy" embraces oxy-containing heteroarylalkyl radicals attached through an oxygen atom to other radicals. In one aspect, heteroarylalkoxy radicals are "lower heteroarylalkoxy" radicals having optionally substituted heteroaryl radicals attached to lower alkoxy radical as described above.

The term "cycloalkyl" includes saturated carbocyclic groups. Some cycloalkyl groups include $C_3$-$C_6$ rings. Other compounds include, cyclopentyl, cyclopropyl, and cyclohexyl.

The term "cycloalkylalkyl" embraces cycloalkyl-substituted alkyl radicals. Some cycloalkylalkyl radicals are "lower cycloalkylalkyl" radicals having cycloalkyl radicals attached to alkyl radicals having one to six carbon atoms. Examples include "5-6-membered cycloalkylalkyl" attached to alkyl portions having one to three carbon atoms. Examples of such radicals include cyclohexylmethyl. The cycloalkyl in said radicals may be additionally substituted with halo, alkyl, alkoxy and hydroxy.

The term "cycloalkenyl" includes carbocyclic groups having one or more carbon-carbon double bonds including "cycloalkyldienyl" compounds. Some cycloalkenyl groups include $C_3$-$C_6$ rings. Other compounds include, for example, cyclopentenyl, cyclopentadienyl, cyclohexenyl and cycloheptadienyl.

The term "comprising" is meant to be open ended, including the indicated component but not excluding other elements.

The term(s) "Formulas I, II, III, IV, V, VI and VII" either alone or in combination includes any sub formulas.

The compounds of the invention are endowed with c-Met inhibitory activity.

The present invention also comprises the use of a compound of the invention, or pharmaceutically acceptable salt thereof, in the manufacture of a medicament for the treatment either acutely or chronically of an angiogenesis mediated disease state, including those described previously. The compounds of the present invention are useful in the manufacture of an anti-cancer medicament. The compounds of the present invention are also useful in the manufacture of a medicament to attenuate or prevent disorders through inhibition of c-Met.

The present invention comprises a pharmaceutical composition comprising a therapeutically effective amount of a compound of the current invention in association with a least one pharmaceutically acceptable carrier, adjuvant or diluent.

The present invention also comprises a method of treating angiogenesis related disorders in a subject having or susceptible to such disorder, the method comprising treating the subject with a therapeutically effective amount of a compound of the current invention.

Combinations

While the compounds of the invention can be administered as the sole active pharmaceutical agent, they can also be used in combination with one or more compounds of the invention or other agents. When administered as a combination, the therapeutic agents can be formulated as separate compositions that are administered at the same time or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of neoplasia, such as with radiation therapy or with cytostatic or cytotoxic agents.

If formulated as a fixed dose, such combination products employ the compounds of this invention within the accepted dosage ranges. Compounds of the current invention may also be administered sequentially with known anticancer or cytotoxic agents when a combination formulation is inappropriate. The invention is not limited in the sequence of administration; compounds of the invention may be administered either prior to, simultaneous with or after administration of the known anticancer or cytotoxic agent.

Currently, standard treatment of primary tumors consists of surgical excision followed by either radiation or IV administered chemotherapy. The typical chemotherapy regime consists of either DNA alkylating agents, DNA intercalating agents, CDK inhibitors, or microtubule poisons. The chemotherapy doses used are just below the maximal tolerated dose and therefore dose limiting toxicities typically include, nausea, vomiting, diarrhea, hair loss, neutropenia and the like.

There are large numbers of antineoplastic agents available in commercial use, in clinical evaluation and in pre-clinical development, which would be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

A first family of antineoplastic agents, which may be used in combination with compounds of the present invention, consists of antimetabolite-type/thymidilate synthase inhibitor antineoplastic agents. Suitable antimetabolite antineoplastic agents may be selected from but not limited to the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, Taiho UFT and uricytin.

A second family of antineoplastic agents, which may be used in combination with compounds of the present invention, consists of alkylating-type antineoplastic agents. Suitable alkylating-type antineoplastic agents may be selected from but not limited to the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with compounds of the present invention consists of antibiotic-type antineoplastic agents. Suitable antibiotic-type antineoplastic agents may be selected from but not limited to the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-AL esperamicin-Alb, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with compounds of the present invention consists of a miscellaneous family of antineoplastic agents, including tubulin interacting agents, topoisomerase II inhibitors, topoisomerase I inhibitors and hormonal agents, selected from but not limited to the group consisting of α-carotene, α-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluoron, benzotript, Ipsen-Beaufour BIM-23015, bisantrene, Bristol-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphirin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanlne derivatives, methylanilinoacridine, Molecular Genetics MGI-136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534.

Alternatively, the present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofuran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

Alternatively, the present compounds may also be used in co-therapies with VEGFR inhibitors including:

N-(4-chlorophenyl)-4-(4-pyridinylmethyl)-1-phthalazinamine;

4-[4-[[[[4-chloro-3-(trifluoromethyl)phenyl]amino]carbonyl]amino]phenoxy]-N-methyl-2-pyridinecarboxamide;

N-[2-(diethylamino)ethyl]-5-[(5-fluoro-1,2-dihydro-2-oxo-3H-indol-3-ylidene)methyl]-2,4-dimethyl-1H-pyrrole-3-carboxamide;

3-[(4-bromo-2,6-difluorophenyl)methoxy]-5-[[[[4-(1-pyrrolidinyl)butyl]amino]carbonyl]amino]-4-isothiazolecarboxamide;

N-(4-bromo-2-fluorophenyl)-6-methoxy-7-[(1-methyl-4-piperidinyl)methoxy]-4-quinazolinamine;

3-[5,6,7,13-tetrahydro-9-[(1-methylethoxy)methyl]-5-oxo-12H-indeno[2,1-a]pyrrolo[3,4-c]carbazol-12-yl]propyl ester N,N-dimethyl-glycine;

N-[5-[[[5-(1,1-dimethylethyl)-2-oxazolyl]methyl]thio]-2-thiazolyl]-4-piperidinecarboxamide;

N-[3-chloro-4-[(3-fluorophenyl)methoxy]phenyl]-6-[5-[[[2-(methylsulfonyl)ethyl]amino]methyl]-2-furanyl]-4-quinazolinamine;

4-[(4-Methyl-1-piperazinyl)methyl]-N-[4-methyl-3-[[4-(3-pyridinyl)-2-pyrimidinyl]amino]-phenyl]benzamide;

N-(3-chloro-4-fluorophenyl)-7-methoxy-6-[3-(4-morpholinyl)propoxy]-4-quinazolinamine;

N-(3-ethynylphenyl)-6,7-bis(2-methoxyethoxy)-4-quinazolinamine;

N-(3-((((2R)-1-methyl-2-pyrrolidinyl)methyl)oxy)-5-(trifluoromethyl)phenyl)-2-((3-(1,3-oxazol-5-yl)phenyl)amino)-3-pyridinecarboxamide;
2-(((4-fluorophenyl)methyl)amino)-N-(3-((((2R)-1-methyl-2-pyrrolidinyl)methyl)oxy)-5-(trifluoromethyl)phenyl)-3-pyridinecarboxamide;
N-[3-(Azetidin-3-ylmethoxy)-5-trifluoromethyl-phenyl]-2-(4-fluoro-benzylamino)-nicotinamide;
6-fluoro-N-(4-(1-methylethyl)phenyl)-2-((4-pyridinylmethyl)amino)-3-pyridinecarboxamide;
2-((4-pyridinylmethyl)amino)-N-(3-(((2S)-2-pyrrolidinylmethyl)oxy)-5-(trifluoromethyl)phenyl)-3-pyridinecarboxamide;
N-(3-(1,1-dimethylethyl)-1H-pyrazol-5-yl)-2-((4-pyridinylmethyl)amino)-3-pyridinecarboxamide;
N-(3,3-dimethyl-2,3-dihydro-1-benzofuran-6-yl)-2-((4-pyridinylmethyl)amino)-3-pyridinecarboxamide;
N-(3-((((2S)-1-methyl-2-pyrrolidinyl)methyl)oxy)-5-(trifluoromethyl)phenyl)-2-((4-pyridinylmethyl)amino)-3-pyridinecarboxamide;
2-((4-pyridinylmethyl)amino)-N-(3-((2-(1-pyrrolidinyl)ethyl)oxy)-4-(trifluoromethyl)phenyl)-3-pyridinecarboxamide;
N-(3,3-dimethyl-2,3-dihydro-1H-indol-6-yl)-2-((4-pyridinylmethyl)amino)-3-pyridinecarboxamide;
N-(4-(pentafluoroethyl)-3-(((2S)-2-pyrrolidinylmethyl)oxy)phenyl)-2-((4-pyridinylmethyl)amino)-3-pyridinecarboxamide;
N-(3-((3-azetidinylmethyl)oxy)-5-(trifluoromethyl)phenyl)-2-((4-pyridinylmethyl)amino)-3-pyridinecarboxamide;
N-(3-(4-piperidinyloxy)-5-(trifluoromethyl)phenyl)-2-((2-(3-pyridinyl)ethyl)amino)-3-pyridinecarboxamide;
N-(4,4-dimethyl-1,2,3,4-tetrahydro-isoquinolin-7-yl)-2-(1H-indazol-6-ylamino)-nicotinamide;
2-(1H-indazol-6-ylamino)-N-[3-(1-methylpyrrolidin-2-ylmethoxy)-5-trifluoromethyl-phenyl]-nicotinamide;
N-[1-(2-dimethylamino-acetyl)-3,3-dimethyl-2,3-dihydro-1H-indol-6-yl]-2-(1H-indazol-6-ylamino)-nicotinamide;
2-(1H-indazol-6-ylamino)-N-[3-(pyrrolidin-2-ylmethoxy)-5-trifluoromethyl-phenyl]-nicotinamide;
N-(1-acetyl-3,3-dimethyl-2,3-dihydro-1H-indol-6-yl)-2-(1H-indazol-6-ylamino)-nicotinamide;
N-(4,4-dimethyl-1-oxo-1,2,3,4-tetrahydro-isoquinolin-7-yl)-2-(1H-indazol-6-ylamino)-nicotinamide;
N-[4-(tert-butyl)-3-(3-piperidylpropyl)phenyl][2-(1H-indazol-6-ylamino)(3-pyridyl)]carboxamide;
N-[5-(tert-butyl)isoxazol-3-yl][2-(1H-indazol-6-ylamino)(3-pyridyl)]carboxamide; and
N-[4-(tert-butyl)phenyl][2-(1H-indazol-6-ylamino)(3-pyridyl)]carboxamide.

Other compounds described in the following patents and patent applications can be used in combination therapy: U.S. Pat. No. 6,258,812, US 2003/0105091, WO 01/37820, U.S. Pat. No. 6,235,764, WO 01/32651, U.S. Pat. Nos. 6,630,500, 6,515,004, 6,713,485, 5,521,184, 5,770,599, 5,747,498, WO 02/68406, WO 02/66470, WO 02/55501, WO 04/05279, WO 04/07481, WO 04/07458, WO 04/09784, WO 02/59110, WO 99/45009, WO 00/59509, WO 99/61422, U.S. Pat. No. 5,990,141, WO 00/12089 and WO 00/02871.

In some embodiments, the combination comprises a composition of the present invention in combination with at least one anti-angiogenic agent. Agents are inclusive of, but not limited to, in vitro synthetically prepared chemical compositions, antibodies, antigen binding regions, radionuclides, and combinations and conjugates thereof. An agent can be an agonist, antagonist, allosteric modulator, toxin or, more generally, may act to inhibit or stimulate its target (e.g., receptor or enzyme activation or inhibition), and thereby promote cell death or arrest cell growth.

Exemplary anti-tumor agents include HERCEPTIN™ (trastuzumab), which may be used to treat breast cancer and other forms of cancer, and RITUXAN™ (rituximab), ZEVALIN™ (ibritumomab tiuxetan), and LYMPHOCIDE™ (epratuzumab), which may be used to treat non-Hodgkin's lymphoma and other forms of cancer, GLEEVAC™ which may be used to treat chronic myeloid leukemia and gastrointestinal stromal tumors, and BEXXAR™ (iodine 131 tositumomab) which may be used for treatment of non-Hodgkins's lymphoma.

Exemplary anti-angiogenic agents include ERBITUX™ (IMC-C225), KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF, or soluble VEGF receptors or a ligand binding region thereof) such as AVASTIN™ or VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as ABX-EGF (panitumumab), IRESSA™ (gefitinib), TARCEVA™ (erlotinib), anti-Ang1 and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto). The pharmaceutical compositions of the present invention can also include one or more agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor "c-met".

Other anti-angiogenic agents include Campath, IL-8, B-FGF, Tek antagonists (Ceretti et al., US Publication No. 2003/0162712; U.S. Pat. No. 6,413,932), anti-TWEAK agents (e.g., specifically binding antibodies or antigen binding regions, or soluble TWEAK receptor antagonists; see, Wiley, U.S. Pat. No. 6,727,225), ADAM distintegrin domain to antagonize the binding of integrin to its ligands (Fanslow et al., US Publication No. 2002/0042368), specifically binding anti-eph receptor and/or anti-ephrin antibodies or antigen binding regions (U.S. Pat. Nos. 5,981,245; 5,728,813; 5,969,110; 6,596,852; 6,232,447; 6,057,124 and patent family members thereof), and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto).

Additional anti-angiogenic/anti-tumor agents include: SD-7784 (Pfizer, USA); cilengitide. (Merck KGaA, Germany, EPO 770622); pegaptanib octasodium, (Gilead Sciences, USA); Alphastatin, (BioActa, UK); M-PGA, (Celgene, USA, U.S. Pat. No. 5,712,291); ilomastat, (Arriva, USA, U.S. Pat. No. 5,892,112); emaxanib, (Pfizer, USA, U.S. Pat. No. 5,792,783); vatalanib, (Novartis, Switzerland); 2-methoxyestradiol, (EntreMed, USA); TLC ELL-12, (Elan, Ireland); anecortave acetate, (Alcon, USA); alpha-D148 Mab, (Amgen, USA); CEP-7055, (Cephalon, USA); anti-Vn Mab, (Crucell, Netherlands) DAC:antiangiogenic, (ConjuChem, Canada); Angiocidin, (InKine Pharmaceutical, USA); KM-2550, (Kyowa Hakko, Japan); SU-0879, (Pfizer, USA); CGP-79787, (Novartis, Switzerland, EP 970070);

ARGENT technology, (Ariad, USA); YIGSR-Stealth, (Johnson & Johnson, USA); fibrinogen-E fragment, (BioActa, UK); angiogenesis inhibitor, (Trigen, UK); TBC-1635, (Encysive Pharmaceuticals, USA); SC-236, (Pfizer, USA); ABT-567, (Abbott, USA); Metastatin, (EntreMed, USA); angiogenesis inhibitor, (Tripep, Sweden); maspin, (Sosei, Japan); 2-methoxyestradiol, (Oncology Sciences Corporation, USA); ER-68203-00, (IVAX, USA); Benefin, (Lane Labs, USA); Tz-93, (Tsumura, Japan); TAN-1120, (Takeda, Japan); FR-111142, (Fujisawa, Japan, JP 02233610); platelet factor 4, (RepliGen, USA, EP 407122); vascular endothelial growth factor antagonist, (Borean, Denmark); cancer therapy, (University of South Carolina, USA); bevacizumab (pINN), (Genentech, USA); angiogenesis inhibitors, (SUGEN, USA); XL 784, (Exelixis, USA); XL 647, (Exelixis, USA); MAb, alpha5beta3 integrin, second generation, (Applied Molecular Evolution, USA and MedImmune, USA); gene therapy, retinopathy, (Oxford BioMedica, UK); enzastaurin hydrochloride (USAN), (Lilly, USA); CEP 7055, (Cephalon, USA and Sanofi-Synthelabo, France); BC 1, (Genoa Institute of Cancer Research, Italy); angiogenesis inhibitor, (Alchemia, Australia); VEGF antagonist, (Regeneron, USA); rBPI 21 and BPI-derived antiangiogenic, (XOMA, USA); PI 88, (Progen, Australia); cilengitide (pINN), (Merck KGaA, German; Munich Technical University, Germany, Scripps Clinic and Research Foundation, USA); cetuximab (INN), (Aventis, France); AVE 8062, (Ajinomoto, Japan); AS 1404, (Cancer Research Laboratory, New Zealand); SG 292, (Telios, USA); Endostatin, (Boston Childrens Hospital, USA); ATN 161, (Attenuon, USA); ANGIOSTATIN, (Boston Childrens Hospital, USA); 2-methoxyestradiol, (Boston Childrens Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProlX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aeterna, Canada); vaccine, angiogenesis, (EntreMed, USA); urokinase plasminogen activator inhibitor, (Dendreon, USA); oglufanide (pINN), (Melmotte, USA); HIF-1alfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol, (EntreMed, USA); anginex, (Maastricht University, Netherlands, and Minnesota University, USA); ABT 510, (Abbott, USA); AAL 993, (Novartis, Switzerland); VEGI, (ProteomTech, USA); tumor necrosis factor-alpha inhibitors, (National Institute on Aging, USA); SU 11248, (Pfizer, USA and SUGEN USA); ABT 518, (Abbott, USA); YH16, (Yantai Rongchang, China); S-3APG, (Boston Childrens Hospital, USA and EntreMed, USA); MAb, KDR, (ImClone Systems, USA); MAb, alpha5 beta1, (Protein Design, USA); KDR kinase inhibitor, (Celltech Group, UK, and Johnson & Johnson, USA); GFB 116, (South Florida University, USA and Yale University, USA); CS 706, (Sankyo, Japan); combretastatin A4 prodrug, (Arizona State University, USA); chondroitinase AC, (IBEX, Canada); BAY RES 2690, (Bayer, Germany); AGM 1470, (Harvard University, USA, Takeda, Japan, and TAP, USA); AG 13925, (Agouron, USA); Tetrathiomolybdate, (University of Michigan, USA); GCS 100, (Wayne State University, USA) CV 247, (Ivy Medical, UK); CKD 732, (Chong Kun Dang, South Korea); MAb, vascular endothelium growth factor, (Xenova, UK); irsogladine (INN), (Nippon Shinyaku, Japan); RG 13577, (Aventis, France); WX 360, (Wilex, Germany); squalamine (pINN), (Genaera, USA); RPI 4610, (Sirna, USA); cancer therapy, (Marinova, Australia); heparanase inhibitors, (InSight, Israel); KL 3106, (Kolon, South Korea); Honokiol, (Emory University, USA); ZK CDK, (Schering AG, Germany); ZK Angio, (Schering AG, Germany); ZK 229561, (Novartis, Switzerland, and Schering AG, Germany); XMP 300, (XOMA, USA); VGA 1102, (Taisho, Japan); VEGF receptor modulators, (Pharmacopeia, USA); VE-cadherin-2 antagonists, (ImClone Systems, USA); Vasostatin, (National Institutes of Health, USA); vaccine, Flk-1, (ImClone Systems, USA); TZ 93, (Tsumura, Japan); TumStatin, (Beth Israel Hospital, USA); truncated soluble FLT 1 (vascular endothelial growth factor receptor 1), (Merck & Co, USA); Tie-2 ligands, (Regeneron, USA); and, thrombospondin 1 inhibitor, (Allegheny Health, Education and Research Foundation, USA).

Alternatively, the present compounds may also be used in co-therapies with other anti-neoplastic agents, such as VEGF antagonists, other kinase inhibitors including p38 inhibitors, KDR inhibitors, EGF inhibitors and CDK inhibitors, TNF inhibitors, metallomatrix proteases inhibitors (MMP), COX-2 inhibitors including celecoxib, NSAID's, or $\alpha_v\beta_3$ inhibitors.

The present invention comprises processes for the preparation of a compound of Formula I, II, III, IV, V, VI and VII. Also included in the family of compounds of the current are the pharmaceutically acceptable salts and solvates thereof. The term "pharmaceutically-acceptable salts" embraces salts commonly used to form alkali metal salts and to form addition salts of free acids or free bases. The nature of the salt is not critical, provided that it is pharmaceutically acceptable. Suitable pharmaceutically acceptable acid addition salts of compounds of the current invention may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, example of which are formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, tartaric, thiocyanic, mesylic, undecanoic, stearic, algenic, β-hydroxybutyric, salicylic, galactaric and galacturonic acid. Suitable pharmaceutically-acceptable base addition salts of compounds of the current invention include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, aistidine, glucamine, isopropylamine, lysine, morpholine, N-ethyl morpholine, piperazine, piperidine, triethylamine, trimethylamine. All of these salts may be prepared by conventional means from the corresponding compound of the invention by reacting, for example, the appropriate acid or base with the compound of the current invention. When a basic group and an acid group are present in the same molecule, a compound of the current invention may also form internal salts.

General Synthetic Procedures

The following is a key of abbreviations which may appear in the specification:
HOAc—acetic acid
MeCN, CH$_3$CN—acetonitrile
NH$_3$—ammonia
NH$_4$Cl—ammonium chloride
Ar—argon
HBTA—O-benzotriazol-1-yl-N,N,N',N'-tetramethyluronium hexafluorophosphate
HATU—O-(7-azabenzotriazol-1-yl)-N,N,N',N'-tetramethyluronium hexafluorophosphate
PyBop—benzotriazol-1-yl-oxy-tripyrrolidino-phosphonium hexafluorophosphate
Pd$_2$(dba)$_3$—bis(dibenzylideneacetone) palladium
BINAP—2,2'-bis(diphenylphosphino)-1,1'-binaphthyl
TEAC—bis(tetra-ethylammonium)carbonate
BBr$_3$—boron tribromide
BSA—bovine serum albumin
Br$_2$—bromine
BOC—butyloxycarbonyl
Cs$_2$CO$_3$—cesium carbonate
CHCl$_3$—chloroform
CDCl$_3$—chloroform deuterated
Cu—copper
CuI—copper(I) iodide
Et$_2$O—diethyl ether
DBU—1,8-diazabicyclo[5.4.0]undec-7-ene
DIBAL—diisobutylaluminum hydride
DIAD—diisopropyl azodicarboxylate
DIEA—diisopropylethylamine
DMF—dimethylformamide
DMAP—4-dimethylaminopyridine
DMSO—dimethylsulfoxide
EDC, EDCI—1-(3-dimethylaminopropyl)-3-ethylcarbodiimide hydrochloride
dppa—diphenylphosphoryl azide
EtOAc—ethyl acetate
FBS—fetal bovine serum
g—gram
h—hour
HBr—hydrobromic acid
HCl—hydrochloric acid
HOBt—1-hydroxybenzotriazole hydrate
H$_2$—hydrogen
H$_2$O$_2$—hydrogen peroxide
Fe—iron
LiHMDS—lithium bis(trimethylsilyl)-amide
LDA—Lithium diisopropylamide
MCPBA—meta-chloroperbenzoic acid MgSO$_4$—magnesium sulfate
MeOH, CH$_3$OH—methanol
MeI—methyl iodide
CH$_2$Cl$_2$, DCM—methylene chloride
NMP—N-methylpyrrolidinone
ML, ml—milliliter
N$_2$—nitrogen
Pd/C—palladium on carbon
Pd(OAc)$_2$—palladium acetate
Pd(OH)$_2$—palladium hydroxide
Pd(PPh$_3$)$_4$—palladium tetrakis triphenylphosphine
Pd(dppf)Cl$_2$—1,1-bis(diphenylphosphino)ferrocene palladium chloride
PBS—phosphate buffered saline
POCl$_3$—phosphorous oxychloride
K$_2$CO$_3$—potassium carbonate
KOH—potassium hydroxide
RT—room temperature
NaHCO$_3$—sodium bicarbonate
NaBH$_4$—sodium borohydride
NaBH$_3$CN—sodium cyanoborohydride
NaOtBu—sodium tert-butoxide
NaOH—sodium hydroxide
NaClO$_2$—sodium chlorite
NaCl—sodium chloride
NaHPO$_4$—sodium biphospate
NaH—sodium hydride
NaI—sodium iodide
Na$_2$SO$_4$—sodium sulfate
TBTU—O-benzotriazol-1-yl-N,N,N',N'-tetramethyluronium tetrafluoroborate
THF—tetrahydrofuran
Et$_3$N, TEA—triethylamine
TFA—trifluoroacetic acid
P(t-bu)$_3$—tri(tert-butyl)phosphine
H$_2$O—water Compounds of the current invention may be synthesized according to the schemes illustrated in the following working examples, as well as through the schemes illustrated in General Methods A through E set forth below, and other methods known to those of skill in the art.

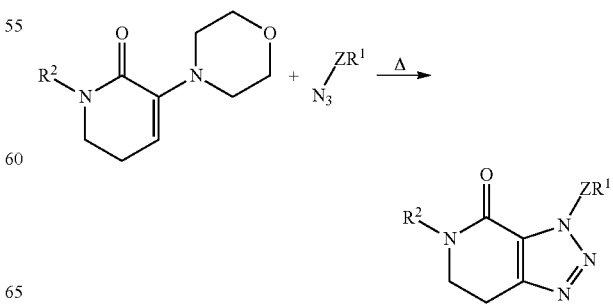

EXAMPLE 1

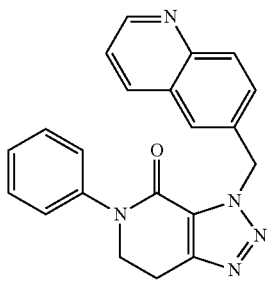 [SMILES: O=C1c2c(nnn2Cc2ccc3ncccc3c2)CCN1c1ccccc1]

5-phenyl-3-(quinolin-6-ylmethyl)-6,7-dihydro-3H-[1,2,3]triazolo[4,5-c]pyridin-4(5H)-one

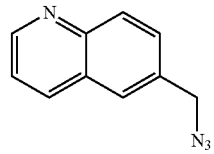 [SMILES: [N-]=[N+]=NCc1ccc2ncccc2c1]

1.A 6-(azidomethyl)quinoline

In a 25 mL round bottom flask under $N_2$ were dissolved quinolin-6-ylmethanol (500 mg, 3141 μmol) and 1,8-diazabicyclo(5.4.0)undec-7-ene (564 μl, 3769 μmol) in 7 mL of PhMe and treated with diphenyl phosphorazidate (815 μl, 3769 μmol) then stirred at rt for 10 h. The crude mixture was directly purified by MPLC (ISCO) with Hexanes:AcOEt 100:0 to 0:100. MS m/z=185.2 [M+1]$^+$. Calc'd for $C_{10}H_8N_4$: 184.2.

3-morpholino-1-phenyl-5,6-dihydropyridin-2(1H)-one (0.17 g, 0.64 mmol) (Prepared according to D. J. P. Pinto et al./*Bioorg. Med. Chem. Lett.* 16 (2006) 4141-4147) and compound 1.A (0.074 g, 0.40 mmol) were microwaved at 130° C. for 1 h in PhMe (5 mL). The reaction mixture was cooled and concentrated under reduced pressure. The crude mixture was evaporated onto silica gel and purified by MPLC (ISCO) with DCM:MeOH 100:0 to 90:10. MS m/z=356.2 [M+1]$^+$. Calc'd for $C_{21}H_{17}N_5O$: 355.4. 1H NMR (400 MHz, Aceton) δ ppm 8.89 (dd, J=4.21, 1.76 Hz, 1 H), 8.31 (dd, J=8.31, 1.37 Hz, 1 H), 8.02 (d, J=8.70 Hz, 1 H), 7.96 (d, J=1.56 Hz, 1 H), 7.81 (dd, J=8.75, 2.01 Hz, 1 H), 7.50 (dd, J=8.31, 4.21 Hz, 1 H), 7.39-7.44 (m, 4 H), 7.25-7.32 (m, 1 H), 6.10 (s, 2 H), 4.18 (t, J=6.85 Hz, 2 H), 3.22 (t, J=6.85 Hz, 2 H)

General Method B

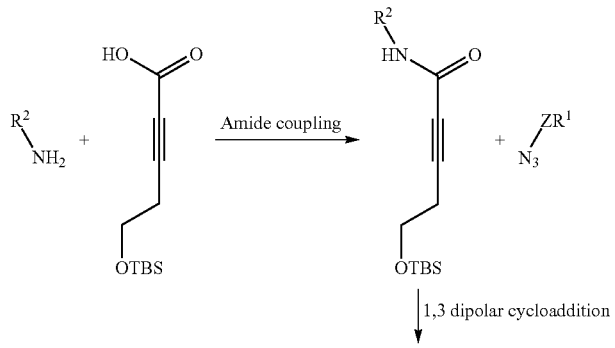

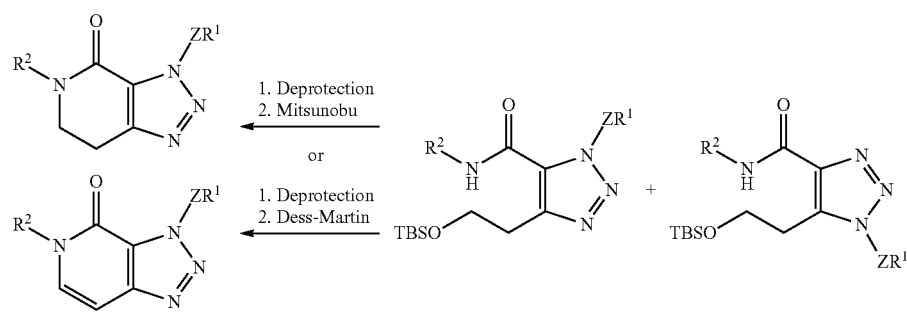

EXAMPLE 2

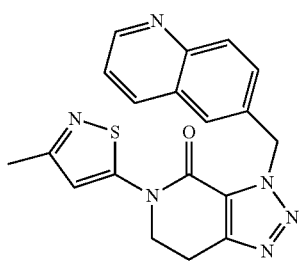 [SMILES: Cc1cc(N2CCc3nnn(Cc4ccc5ncccc5c4)c3C2=O)sn1]

5-(3-methylisothiazol-5-yl)-3-(quinolin-6-ylmethyl)-6,7-dihydro-3H-[1,2,3]triazolo[4,5-c]pyridin-4(5H)-one

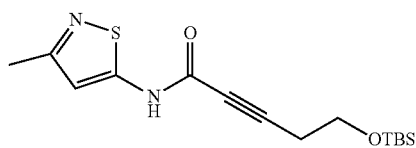 [SMILES: Cc1cc(NC(=O)C#CCCO[Si](C)(C)C(C)(C)C)sn1]

2.A 5-(tert-butyldimethylsilyloxy)-N-(3-methylisothiazol-5-yl)pent-2-ynamide

In a 50 mL round bottom flask under $N_2$ were dissolved HATU (1623 mg, 4270 µmol), 3-methylisothiazol-5-amine hydrochloride (495 mg, 3284 µmol), 5-(tert utyldimethylsilyloxy)pent-2-ynoic acid (750 mg, 3284 µmol) (Prepared according to John S. Carey/*J. Org. Chem.* 66 (2001) 2526-2529) and Hünig's Base (1721 µl, 9853 µmol) in 13 mL of DMF then stirred at rt for 2 h. The reaction mixture was concentrated under reduced pressure and then directly purified by MPLC (ISCO) with DCM:MeOH 100:0 to 90:10. MS m/z=325.2 [M+1]$^+$. Calc'd for $C_{15}H_{24}N_2O_2SSi$: 324.1.

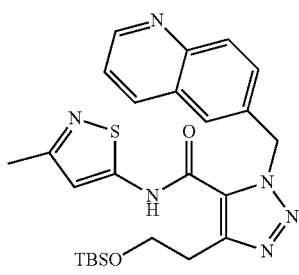 [SMILES: Cc1cc(NC(=O)c2c(CCO[Si](C)(C)C(C)(C)C)nnn2Cc2ccc3ncccc3c2)sn1]

2.B 5-(2-(tert-butyldimethylsilyloxy)ethyl)-N-(3-methylisothiazol-5-yl)-3-(quinolin-6-ylmethyl)-3H-1,2,3-triazole-4-carboxamide In a 10 mL microwave sealed tube under $N_2$ was dissolved compound 2.A (512 mg, 1578 µmol) and 1.A (291 mg, 1578 µmol) in 5 mL of PhMe and was heated at 150° C. with stirring in the microwave for 3 h. The crude mixture (2:3 mixtures of isomers) was directly purified by MPLC (ISCO) with Hexanes:AcOEt 30:70 (second fraction and major isomer determined by NMR analysis). MS m/z=509.2 [M+1]$^+$. Calc'd for $C_{25}H_{32}N_6O_2SSi$: 508.2.

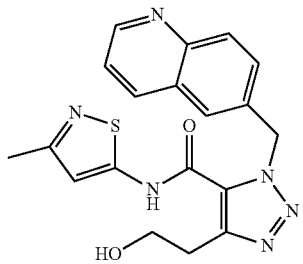 [SMILES: Cc1cc(NC(=O)c2c(CCO)nnn2Cc2ccc3ncccc3c2)sn1]

2.C 5-(2-hydroxyethyl)-N-(3-methylisothiazol-5-yl)-3-(quinolin-6-ylmethyl)-3H-1,2,3-triazole-4-carboxamide In a 25 mL round bottom flask was dissolved 2.B (369 mg, 725 µmol) and aqueous HCl (6N) (363 µl, 2176 µmol) in 5 mL of MeOH then stirred at rt for 2 h. The reaction mixture was concentrated under reduced pressure and the crude compound was judge to be used without further purification in the next step. MS m/z=395.2 [M+1]$^+$. Calc'd for $C_{19}H_{18}N_6O_2S$: 394.1.

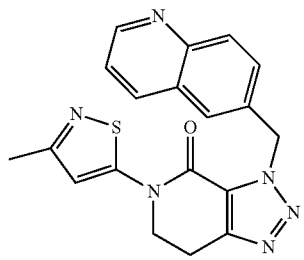 [SMILES: Cc1cc(N2CCc3nnn(Cc4ccc5ncccc5c4)c3C2=O)sn1]

5-(3-methylisothiazol-5-yl)-3-(quinolin-6-ylmethyl)-6,7-dihydro-3H-[1,2,3]triazolo[4,5-c]pyridin-4(5H)-one In a 10 mL round bottom flask under $N_2$ was dissolved triphenylphosphine (140 mg, 570 µmol), 2.C (150 mg, 380 µmol) followed by DEAD (90 µl, 570 µmol) in 2 mL of THF and was stirred at rt for 2 h. The crude reaction mixture was pass through a conditioned Isolute® SPE column (SCX-2) and then washed 3× with MeOH. After, the final compound was released using a 2 M Ammonia in MeOH and the solution was concentrated under reduced pressure and directly purified by MPLC (ISCO) with DCM:MeOH+NH$_4$OH 100:0 to 90:10. MS m/z=376.1 [M+1]$^+$. Calc'd for $C_{19}H_{16}N_6OS$: 377.2. 1H NMR (400 MHz, DMSO-d$_6$) δ ppm 8.90 (dd, J=4.21, 1.76 Hz, 1 H), 8.37 (ddd, J=8.39, 1.59, 0.59 Hz, 1 H), 8.02 (d, J=8.71 Hz, 1 H), 7.89 (d, J=1.66 Hz, 1 H), 7.73 (dd, J=8.75, 2.01 Hz, 1 H), 7.54 (dd, J=8.31, 4.21 Hz, 1 H), 7.11 (s, 1 H), 6.11 (s, 2 H), 4.42 (t, J=7.04 Hz, 2 H), 3.30 (t, J=7.04 Hz, 2 H), 2.36 (s, 3 H)

EXAMPLE 3

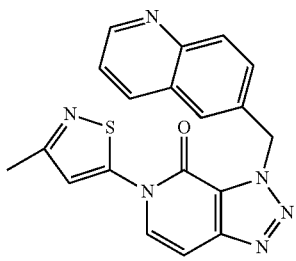 [SMILES: Cc1cc(-n2ccc3nnn(Cc4ccc5ncccc5c4)c3c2=O)sn1]

5-(3-methylisothiazol-5-yl)-3-(quinolin-6-ylmethyl)-3H-[1,2,3]triazolo[4,5-c]pyridin-4(5H)-one In a 10 mL sealed tube under N$_2$ was dissolved compound 2.C (150 mg, 380 μmol) and Dess-MartinPeriodinane (323 mg, 761 μmol) in 3 mL of DCM and stirred at rt for 1 h. The reaction mixture was then heated at 60° C. for 1 h. The reaction mixture was passed through a conditioned Isolute® SPE column (SCX-2) and then washed 3× with MeOH. After that, the final compound was released using a 2 M Ammonia in MeOH and then the solution was concentrated under reduced pressure. The crude mixture was purified by MPLC (ISCO) with DCM:MeOH+NH$_4$OH 100:0 to 90:10. MS m/z=374.1 [M+1]$^+$. Calc'd for C$_{19}$H$_{14}$N$_6$OS: 375.1. 1H NMR (400 MHz, DMSO-d$_6$) δ ppm 8.90 (dd, J=4.16, 1.71 Hz, 1H), 8.33-8.38 (m, 2 H), 8.02 (d, J=8.70 Hz, 1 H), 7.92 (d, J=1.86 Hz, 1 H), 7.76-7.80 (m, 2 H ), 7.53 (dd, J=8.27, 4.25 Hz, 1 H), 7.31 (d, J=7.73 Hz, 1 H), 6.31 (s, 2 H), 2.43 (s, 3 H).

EXAMPLE 4

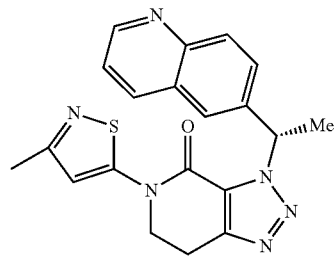 [SMILES: Cc1cc(N2CCc3nnn([C@@H](C)c4ccc5ncccc5c4)c3C2=O)sn1]

(S)-5-(3-methylisothiazol-5-yl)-3-(1-(quinolin-6-yl)ethyl)-6,7-dihydro-3H-[1,2,3]triazolo[4,5-c]pyridin-4(5H)-one

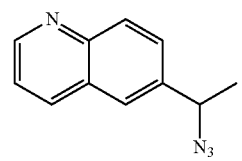

4.A (R/S)-6-(1-azidoethyl)quinoline

In a 50 mL round bottom flask under N$_2$ was dissolved diphenyl phosphorazidate (2.44 ml, 11.3 mmol), DBU (1.69 ml, 11.3 mmol) and 1-(quinolin-6-yl)ethanol (1.65 g, 9.53 mmol) (Prepared according to B. P. Lugovkin,/*Zhurnal Obshchei Khimii* 25 (1955) 392-397) in 20 mL of PhMe stirred at rt for 10 h. The crude mixture was directly purified

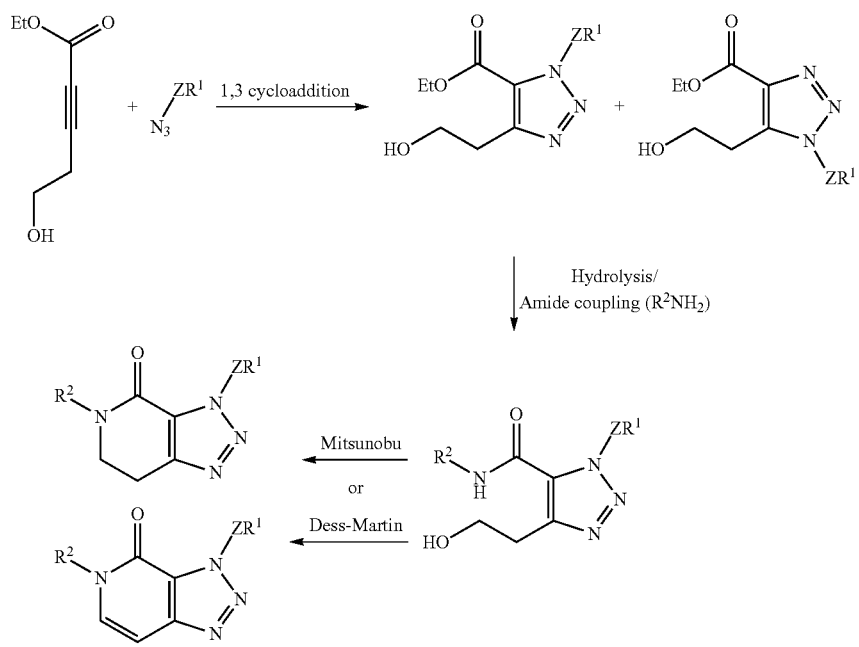

General Method C by MPLC (ISCO) with Hexanes:AcOEt 100:0 to 0:100. MS m/z=199.2 [M+1]⁺. Calc'd for $C_{11}H_{10}N_4$: 198.1.

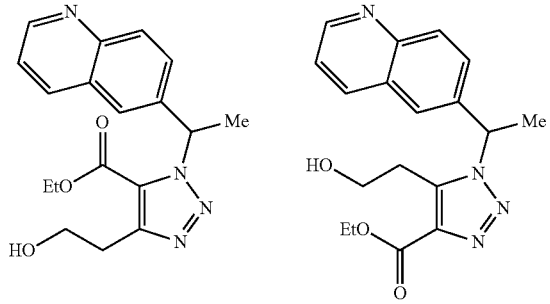 [SMILES: CCOC(=O)c1c(CCO)nnn1C(C)c1ccc2ncccc2c1 ; CCOC(=O)c1nnn(C(C)c2ccc3ncccc3c2)c1CCO]

4.B (R/S)-ethyl 5-(2-hydroxyethyl)-3-(1-(quinolin-6-yl)ethyl)-3H-1,2,3-triazole-4-carboxylate 4.C (R/S)-ethyl 5-(2-hydroxyethyl)-1-(1-(quinolin-6-yl)ethyl)-1H-1,2,3-triazole-4-carboxylate In a 20 mL microwaves sealed tube under $N_2$ was dissolved ethyl 5-hydroxypent-2-ynoate (1947 mg, 13697 µmol) (Prepared according to Ryan R. Burton and William Tam/*Org. Lett.* 9 (2007) 3287-3290) and 4.A (1.81 g, 9131 µmol) in 10 mL of dichlorobenzene and heated with stirring at 180° C. in a microwave for 20 minutes. The crude mixture was purified by MPLC (ISCO) with 100% MeCN to afford in the first fraction 4.B and in the second fraction 4.C (regioisomer determined by NMR analysis). MS m/z=341.2 [M+1]⁺. Calc'd for $C_{18}H_{20}N_4O_3$: 340.2.

4.D (R/S)-5-(2-hydroxyethyl)-N-(3-methylisothiazol-5-yl)-3-(1-(quinolin-6-yl)ethyl)-3H-1,2,3-triazole-4-carboxamide In a 25 mL sealed tube under $N_2$ was dissolved potassium tert-butoxide (402 mg, 3584 µmol) in 4 mL of MeOH and stirred at rt. After 5 minutes, 3-methylisothiazol-5-amine hydrochloride (284 mg, 1886 µmol) was added followed after 5 minutes by 4.B (321 mg, 943 µmol) and then heated at 60° C. for 1 h. The crude mixture was evaporated onto silica gel and purified by MPLC (ISCO) with DCM:MeOH 100:0 to 90:10. MS m/z=409.2 [M+1]⁺. Calc'd for $C_{20}H_{20}N_6O_2S$: 408.1.

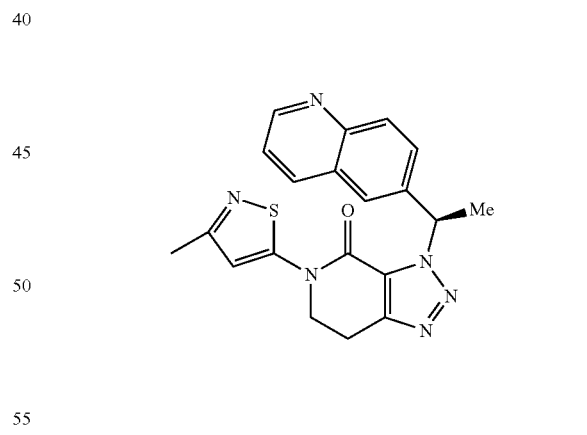

(S)-5-(3-methylisothiazol-5-yl)-3-(1-(quinolin-6-yl)ethyl)-6,7-dihydro-3H-[1,2,3]triazolo[4,5-c]pyridin-4(5H)-one Prepared according to preparation of example compound 2. Chiral separation by preparative SFC (Chiralpak® AD (4.6×100 mm 5µ), 30% IPA 0.2% DEA, 5 mL/min; $t_r$ 2.43 min). MS m/z=390.1 [M+1]⁺. Calc'd for $C_{20}H_{18}N_6OS$: 391.2. 1H NMR (400 MHz, DMSO-$d_6$) δ ppm 8.89 (dd, J=4.11, 1.76 Hz, 1 H), 8.39 (ddd, J=8.51, 1.66, 0.59 Hz, 1 H), 8.02 (d, J=8.80 Hz, 1 H), 7.93 (d, J=1.96 Hz, 1 H), 7.78 (dd, J=8.85, 2.10 Hz, 1 H), 7.54 (dd, J=8.36, 4.25 Hz, 1 H), 7.09 (s, 1 H), 6.70 (q, J=7.08 Hz, 1 H), 4.38 (t, J=7.09 Hz, 2 H), 3.28 (t, J=7.14 Hz, 2 H), 2.35 (s, 3 H), 2.07 (d, J=7.04 Hz, 3 H). On the basis of previous crystallographic data and potency recorded for related compound in the same program, the absolute stereochemistry has been assigned to be the S enantiomer.

EXAMPLE 5

(R)-5-(3-methylisothiazol-5-yl)-3-(1-(quinolin-6-yl)ethyl)-6,7-dihydro-3H-[1,2,3]triazolo[4,5-c]pyridin-4(5H)-one Prepared according to preparation of example compound 2. Chiral separation by preparative SFC (Chiralpak® AD (4.6×100 mm 5µ), 30% IPA 0.2% DEA, 5 mL/min; $t_r$ 1.58 min). On the basis of previous crystallographic data and

EXAMPLE 6

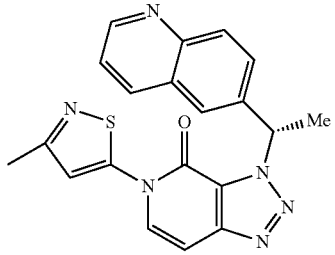 [SMILES: Cc1cc(-n2ccc3nnn([C@@H](C)c4ccc5ncccc5c4)c3c2=O)sn1]

(S)-5-(3-methylisothiazol-5-yl)-3-(1-(quinolin-6-yl)ethyl)-3H-[1,2,3]triazolo[4,5-c]pyridin-4(5H)-one Prepared according to preparation of example compound 3. Chiral separation by preparative SFC (Chiralpak® AD (4.6×100 mm 5μ), 45% MeOH 0.2% DEA, 5 mL/min; $t_r$ 2.02 min). MS m/z=388.1 [M+1]$^+$. Calc'd for $C_{20}H_{16}N_6OS$: 389.1. 1H NMR (400 MHz, CHLOROFORM-d) δ ppm 8.92 (dd, J=4.35, 1.71 Hz, 1 H), 8.27 (d, J=8.02 Hz, 1 H), 8.21 (d, J=9.19 Hz, 1 H), 8.03 (d, J=1.86 Hz, 1 H), 7.95 (dd, J=8.80, 1.96 Hz, 1 H), 7.72 (d, J=7.73 Hz, 1 H), 7.48 (dd, J=8.27, 4.45 Hz, 1 H), 7.11 (d, J=7.73 Hz, 1 H), 7.10 (s, 1 H), 6.99 (q, J=7.17 Hz, 1 H), 2.53 (s, 3 H), 2.29 (d, J=7.14 Hz, 3 H). On the basis of previous crystallographic data and potency recorded for related compound in the same program, the absolute stereochemistry has been assigned to be the S enantiomer.

EXAMPLE 7

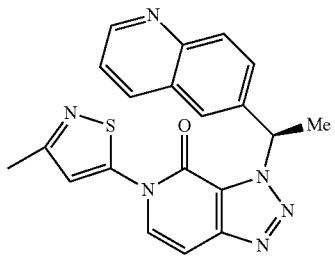 [SMILES: Cc1cc(-n2ccc3nnn([C@H](C)c4ccc5ncccc5c4)c3c2=O)sn1]

(R)-5-(3-methylisothiazol-5-yl)-3-(1-(quinolin-6-yl)ethyl)-3H-[1,2,3]triazolo[4,5-c]pyridin-4(5H)-one Prepared according to preparation of example compound 3. Chiral separation by preparative SFC (Chiralpak® AD (4.6×100 mm 5μ) 45% MeOH 0.2% DEA, 5 mL/min; $t_r$ 1.60 min). On the basis of previous crystallographic data and potency recorded for related compound in the same program, the absolute stereochemistry has been assigned to be the R enantiomer.

EXAMPLE 8

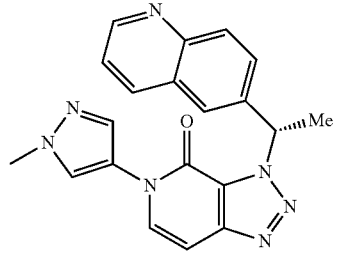 [SMILES: C[C@@H](c1ccc2ncccc2c1)n1nnc2ccn(-c3cnn(C)c3)c(=O)c21]

(S)-5-(1-methyl-1H-pyrazol-4-yl)-3-(1-(quinolin-6-yl)ethyl)-3H-[1,2,3]triazolo[4,5-c]pyridin-4(5H)-one

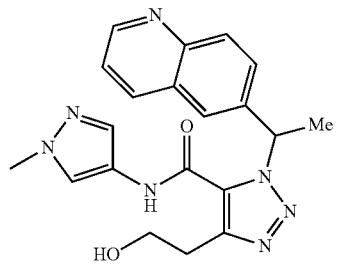 [SMILES: CC(c1ccc2ncccc2c1)n1nnc(CCO)c1C(=O)Nc1cnn(C)c1]

8.A (R/S)-5-(2-hydroxyethyl)-N-(1-methyl-1H-pyrazol-4-yl)-3-(1-(quinolin-6-yl)ethyl)-3H-1,2,3-triazole-4-carboxamide In a 25 mL round bottom flask was dissolved NaOH (1N H$_2$O) (1945 μl, 1945 μmol) and 4.B (331 mg, 972 μmol) in 10 mL of p-dioxane and stirred at rt for 1 h. The reaction mixture was then neutralized with HCl (6N H$_2$O) (118 μl, 3890 μmol) and concentrated under reduced pressure and used directly in the next step. In a 10 mL round bottom flask under N$_2$ was dissolved 1-methyl-1H-pyrazol-4-amine hydrochloride (260 mg, 1945 μmol), DIPEA (849 μl, 4862 μmol) and the crude acid in 2 mL of DMF and stirred at 0° C. and treated with HATU (1109 mg, 2917 μmol) and warmed to rt for 2 h. The reaction mixture was diluted with AcOEt then washed 5× with small portion of water and the organic layer was dried over Na$_2$SO$_4$, filtered and concentrated under reduced pressure. The crude mixture was purified by MPLC (ISCO) with DCM:MeOH+NH$_4$OH 100:0 to 90:10.

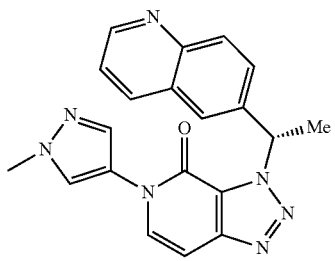 [SMILES: C[C@@H](c1ccc2ncccc2c1)n1nnc2ccn(-c3cnn(C)c3)c(=O)c21]

(S)-5-(1-methyl-1H-pyrazol-4-yl)-3-(1-(quinolin-6-yl)ethyl)-3H-[1,2,3]triazolo[4,5-c]pyridin-4(5H)-one Prepared according to preparation of example compound 3. Chiral separation by preparative SFC (Chiracel® OJ (4.6× 100 mm 5µ), 20% MeOH 0.2% DEA, 5 mL/min; t$_r$ 1.40 min). MS m/z=371.2 [M+1]$^+$. Calc'd for C$_{20}$H$_{17}$N$_7$O: 372.0. 1H NMR (400 MHz, DMSO-d$_6$) δ ppm 8.89 (dd, J=4.16, 1.71 Hz, 1 H), 8.38 (ddd, J=8.39, 1.44, 0.64 Hz, 1 H), 8.20 (d, J=0.39 Hz, 1 H), 8.00 (d, J=8.80 Hz, 1 H), 7.92 (d, J=1.96 Hz, 1 H), 7.74-7.78 (m, 2 H), 7.64 (d, J=7.43 Hz, 1 H), 7.52 (dd, J=8.31, 4.21 Hz, 1 H), 7.01 (d, J=7.53 Hz, 1 H), 6.87-6.94 (m, 1 H), 3.87 (s, 3 H), 2.15 (d, J=7.14 Hz, 3 H). On the basis of previous crystallographic data and potency recorded for related compound in the same program, the absolute stereochemistry has been assigned to be the S enantiomer.

EXAMPLE 9

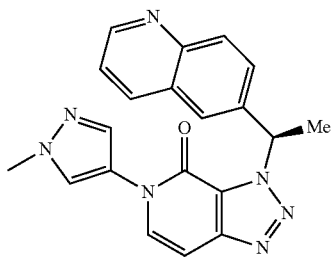 [SMILES: C[C@H](c1ccc2ncccc2c1)n1nnc2ccn(-c3cnn(C)c3)c(=O)c21]

(R)-5-(1-methyl-1H-pyrazol-4-yl)-3-(1-(quinolin-6-yl)ethyl)-3H-[1,2,3]triazolo[4,5-c]pyridin-4(5H)-one Prepared according to preparation of example compound 3. Chiral separation by preparative SFC (Chiracel® OJ (4.6× 100 mm 5µ), 20% MeOH 0.2% DEA, 5 mL/min; t$_r$ 1.12 min). On the basis of previous crystallographic data and potency recorded for related compound in the same program, the absolute stereochemistry has been assigned to be the R enantiomer.

General Method D

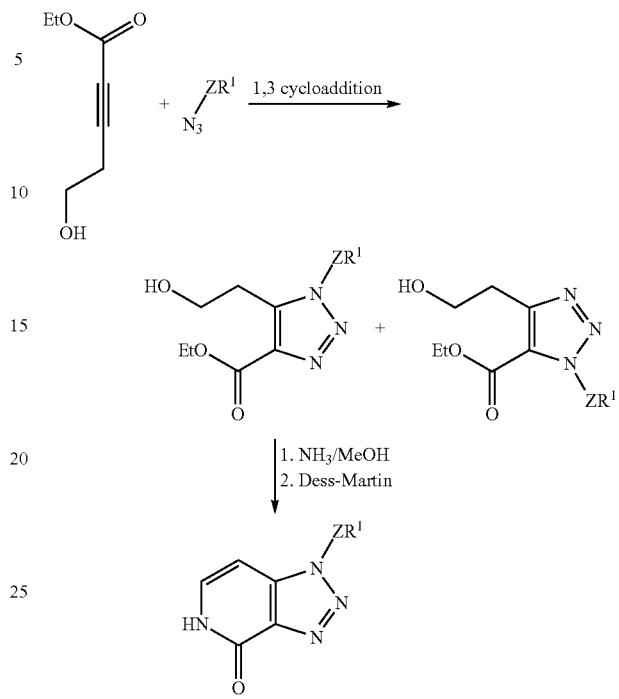

EXAMPLE 10

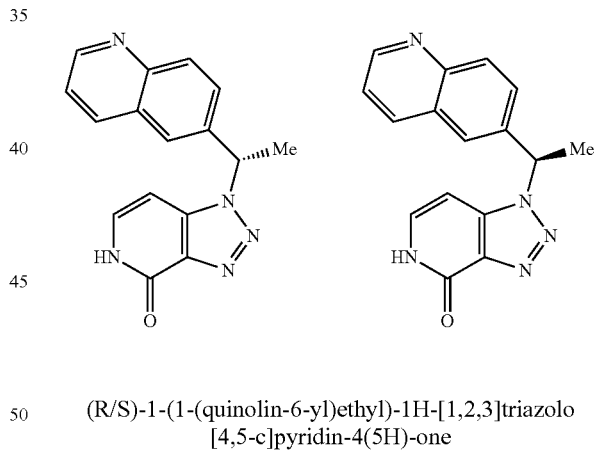

(R/S)-1-(1-(quinolin-6-yl)ethyl)-1H-[1,2,3]triazolo[4,5-c]pyridin-4(5H)-one

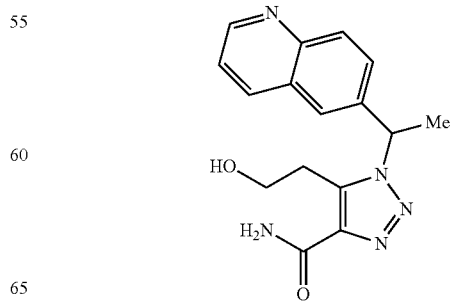

10.A (R/S)-5-(2-hydroxyethyl)-1-(1-(quinolin-6-yl) ethyl)-1H-1,2,3-triazole-4-carboxamide In a 10 mL microwaves sealed tube under N₂ was dissolved ethyl 4.C (630 mg, 1851 µmol) in NH₃ (6N in MeOH) (4.00 ml, 18.0 mmol) then stirred and heated at 150° C. with a microwave for 5 h. The reaction mixture was concentrated under reduced pressure and the crude was judge to be used without further purification in the next step.

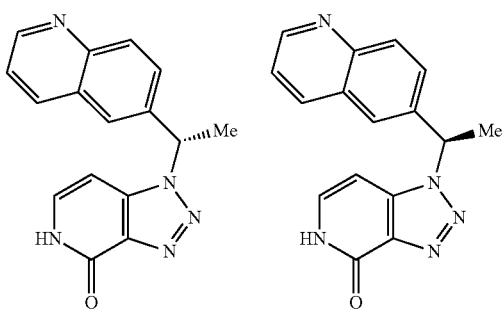 [SMILES: C[C@@H](c1ccc2ncccc2c1)n1nnc2c(=O)[nH]ccc21 ; C[C@H](c1ccc2ncccc2c1)n1nnc2c(=O)[nH]ccc21]

(R/S)-1-(1-(quinolin-6-yl)ethyl)-1H-[1,2,3]triazolo[4,5-c]pyridin-4(5H)-one

Prepared according to preparation of example compound 3. MS m/z=291.1 [M+1]⁺. Calc'd for $C_{16}H_{13}N_5O$: 292.1. 1H NMR (400 MHz, DMSO-d₆) δ ppm 11.49 (br. s., 1 H), 8.90 (dd, J=4.21, 1.76 Hz, 1 H), 8.36-8.40 (m, 1 H), 8.01 (d, J=8.80 Hz, 1 H), 7.97 (d, J=1.96 Hz, 1 H), 7.70 (dd, J=8.80, 2.15 Hz, 1 H), 7.55 (dd, J=8.31, 4.21 Hz, 1 H), 7.30 (dd, J=7.14, 6.06 Hz, 1 H), 6.60 (dd, J=7.14, 0.98 Hz, 1 H), 6.40 (q, J=6.85 Hz, 1 H), 2.12 (d, J=6.94 Hz, 3 H).

EXAMPLE 11

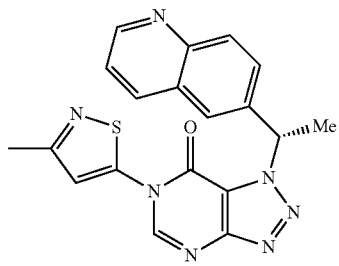 [SMILES: Cc1cc(-n2cnc3nnn([C@@H](C)c4ccc5ncccc5c4)c3c2=O)sn1]

(S)-6-(3-methylisothiazol-5-yl)-1-(1-(quinolin-6-yl)ethyl)-1H-[1,2,3]triazolo[4,5-d]pyrimidin-7(6H)-one

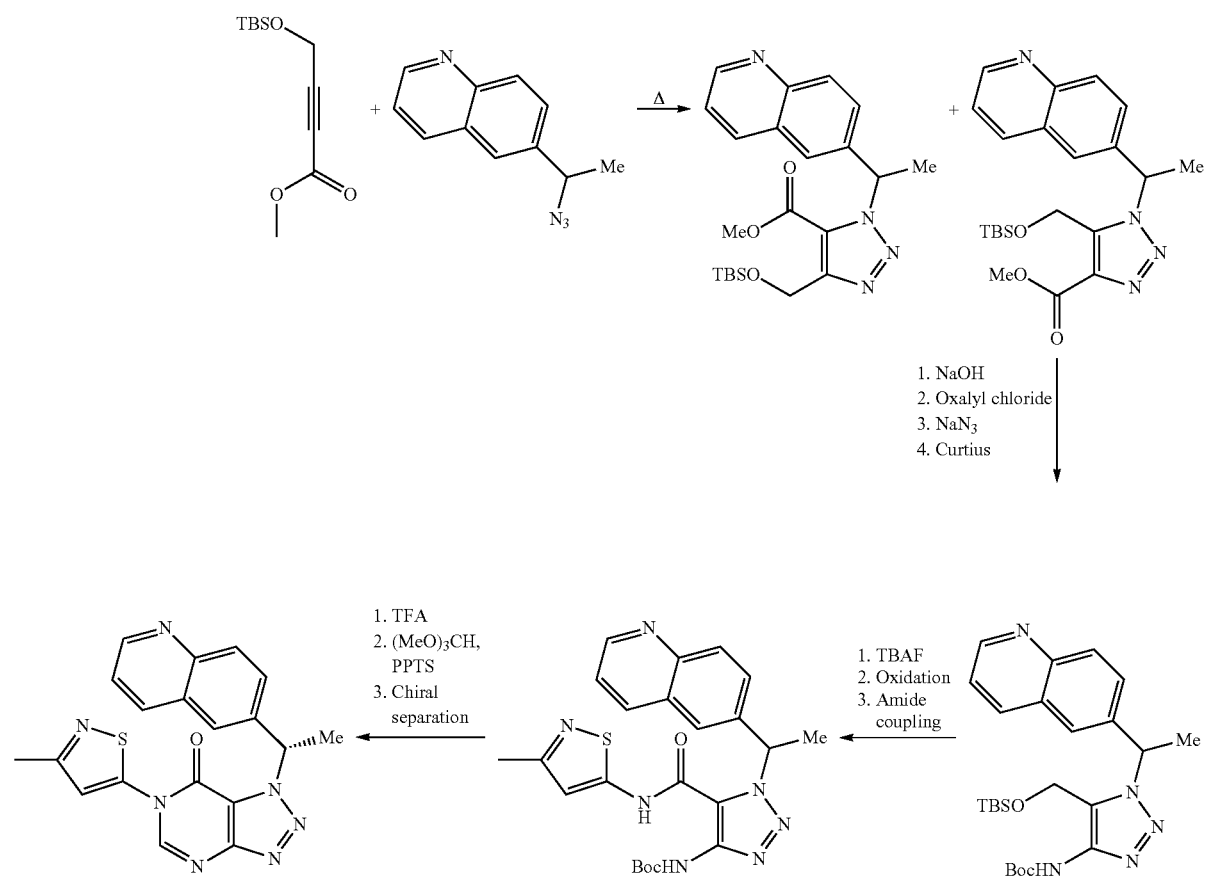

EXAMPLE 12
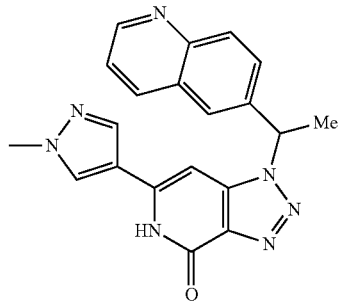 [SMILES: CC(c1ccc2ncccc2c1)n1nnc2c(=O)[nH]c(-c3cnn(C)c3)cc21]
6-(1-methyl-1H-pyrazol-4-yl)-1-(1-(quinolin-6-yl)ethyl)-1H-[1,2,3]triazolo[4,5-c]pyridin-4(5H)-one
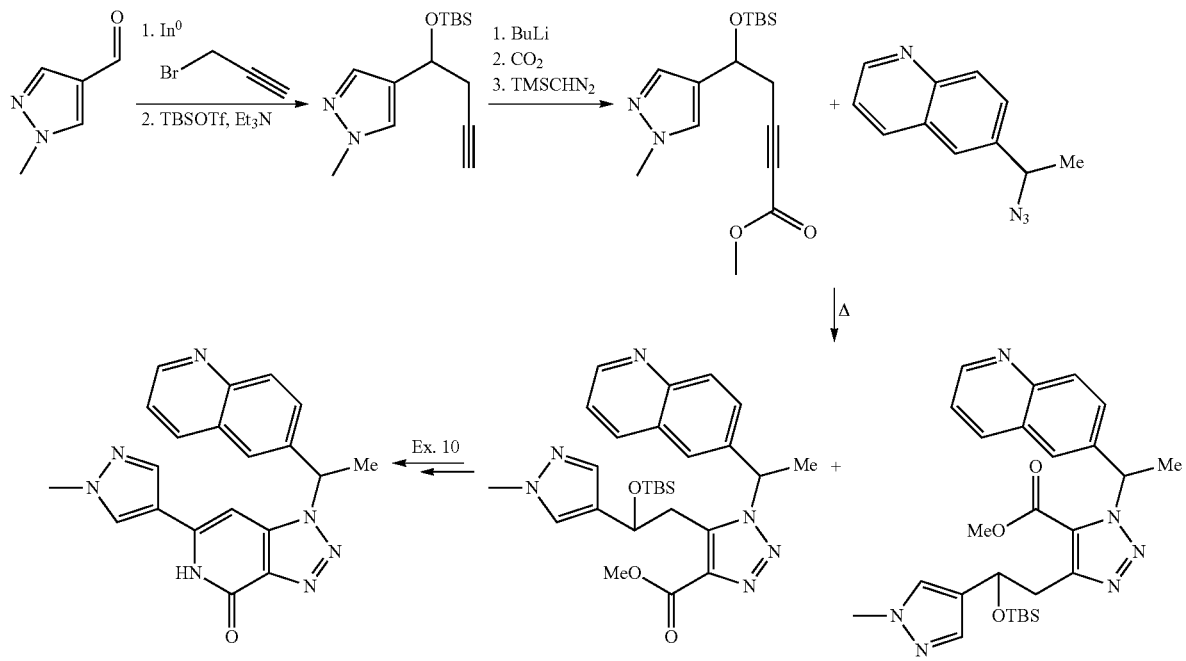
EXAMPLE 13
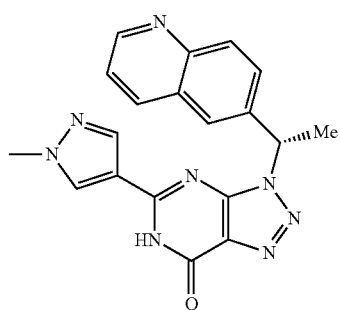 [SMILES: C[C@@H](c1ccc2ncccc2c1)n1nnc2c(=O)[nH]c(-c3cnn(C)c3)nc21]
(S)-5-(1-methyl-1H-pyrazol-4-yl)-3-(1-(quinolin-6-yl)ethyl)-3H-[1,2,3]triazolo[4,5-d]pyrimidin-7(6H)-one
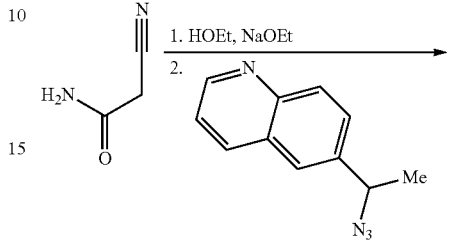
-continued
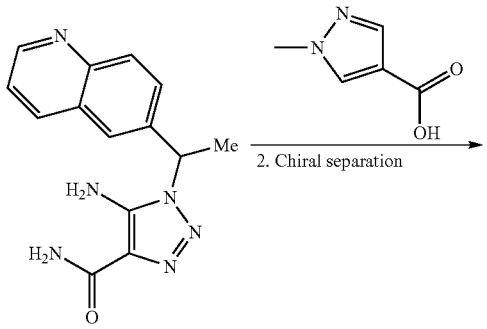

-continued

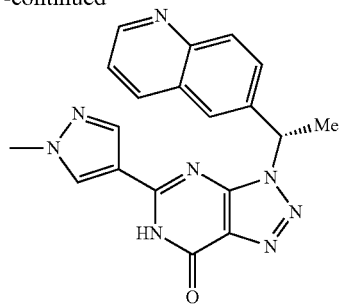

General Method E

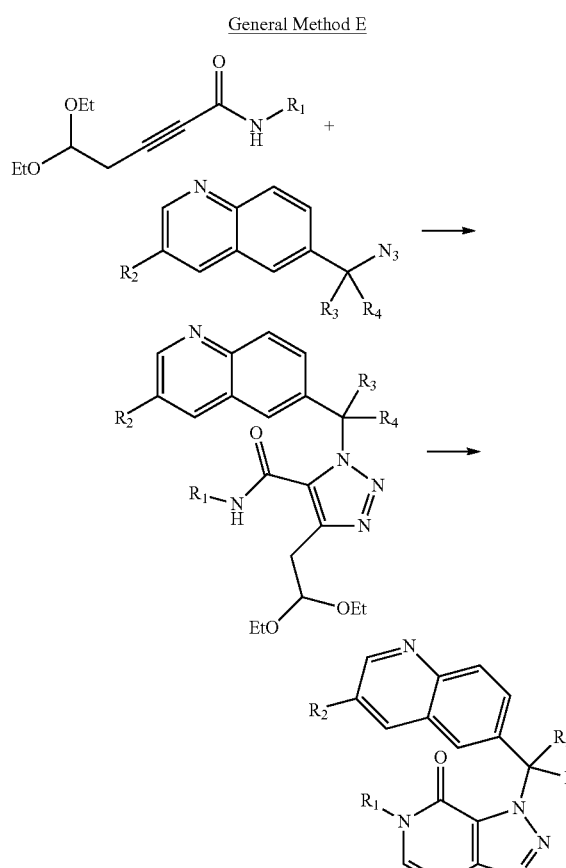

EXAMPLE 14

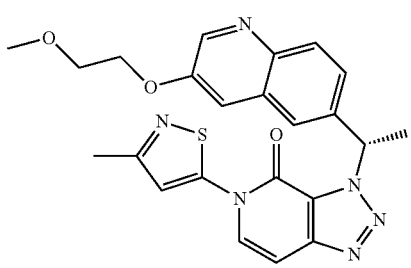 [SMILES: COCCOc1cnc2ccc([C@H](C)n3nnc4ccn(-c5cc(C)ns5)c(=O)c43)cc2c1]

(S)-3-(1-(3-(2-methoxyethoxy)quinolin-6-yl)ethyl)-
5-(3-methylisothiazol-5-yl)-3H-[1,2,3]triazolo[4,5-c]
pyridin-4(5H)-one

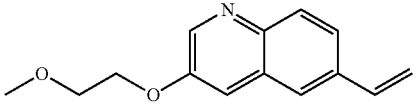 [SMILES: C=Cc1ccc2ncc(OCCOC)cc2c1]

1) 3-(2-methoxyethoxy)-6-vinylquinoline. In a 1-L round bottom flask under $N_2$ were dissolved $PdCl_2$(dppf)-$CH_2Cl_2$ adduct (5.47 g, 6.70 mmol), 6-bromo-3-(2-methoxyethoxy)quinoline (63.0 g, 223 mmol), 4,4,5,5-tetramethyl-2-vinyl-1,3,2-dioxaborolane (47.3 mL, 279 mmol) and cesium carbonate (146 g, 447 mmol) in 450 mL of p-dioxane/water (5:1). The reaction was stirred and heated at 80° C. for 8 h. The reaction mixture was diluted with EtOAc, and the solid precipitate was filtered and discarded. The filtrate was diluted with water and extracted (×3) with EtOAc, and the combined organics were then dried over $Na_2SO_4$, filtered and concentrated under reduced pressure. After concentrating ⅔ of the solvent, a solid crashed out of the solution, which was filtered and discarded. After complete concentration, the crude 3-(2-methoxyethoxy)-6-vinylquinoline was used without further purification.

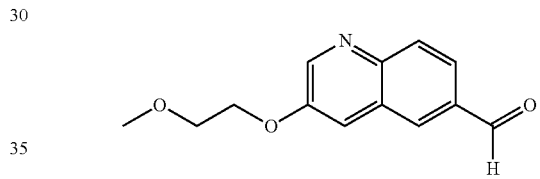

2) 3-(2-methoxyethoxy)quinoline-6-carbaldehyde. In a 50-mL flask, osmium tetroxide (2.3 ml, 0.37 mmol) and 3-(2-methoxyethoxy)-6-vinylquinoline (1.70 g, 7.4 mmol) were dissolved in THF (15 mL) and water (15 mL), and then sodium periodate (3.2 g, 15 mmol) was added, and the reaction was stirred for 1 h. The reaction mixture was extracted with DCM (×3), and the combined organic layers were dried over sodium sulfate, filtered and concentrated in vacuo to yield crude 3-(2-methoxyethoxy)quinoline-6-carbaldehyde.

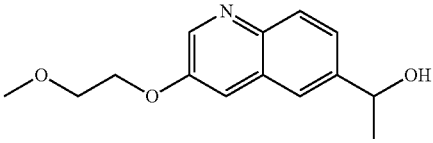 [SMILES: COCCOc1cnc2ccc(C(C)O)cc2c1]

3) 1-(3-(2-methoxyethoxy quinolin-6-yl)ethanol. 3-(2-methoxyethoxy)quinoline-6-carbaldehyde (1.7 g, 7.4 mmol) was dissolved in THF (29 mL, 7.4 mmol) and cooled to −78° C. To the solution was added methylmagnesium bromide (7.4 mL, 22 mmol), and the reaction was allowed to warm to RT. After 1 h, the reaction was quenched with sat. aq ammonium chloride. The material was extracted with DCM (×3) and the combined organics were dried over sodium sulfate, filtered and concentrated in vacuo. The crude material was then purified via MPLC (eluting with 0-100% 90:10:1 DCM:MeOH:$NH_4OH$ in DCM). 1-(3-(2-methoxyethoxy)quinolin-6-yl)ethanol was obtained.

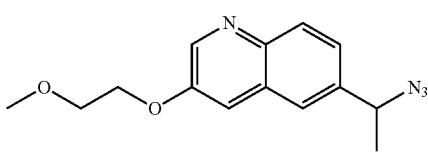 [SMILES: COCCOc1cnc2ccc(C(C)N=[N+]=[N-])cc2c1]

4) 6-(1-azidoethyl)-3-(2-methoxyethoxy)quinoline. To 1-(3-(2-methoxyethoxy)quinolin-6-yl)ethanol (22.9 g, 93 mmol) in dry toluene (185 mL, 93 mmol) was added DBU (17 mL, 111 mmol) and powdered 4 Å molecular sieves (23 g). The mixture was stirred at RT for 15 minutes, at which time DPPA (24 mL, 111 mmol) was added dropwise (over 10 minutes) with stirring in an ice-water bath, and then the mixture was stirred at RT for 6 h. The heterogeneous mixture was diluted with 50:50 hexanes:EtOAc (100 mL), and water (100 mL), and was stirred vigorously for 5 minutes. The organic phase was separated and the aqueous layer was extracted with EtOAc. The organic layer was dried, filtered, and concentrated in vacuo. The crude material was taken up in EtOAc and washed with 2.0 N HCl. The organic layer was discarded, and the aqueous layer was then made basic with 2.0 N NaOH, and back extracted with EtOAc (×3). The organic layer was dried, filtered and concentrated in vacuo to yield 6-(1-azidoethyl)-3-(2methoxyethoxy)quinoline.

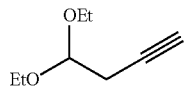

4,4-diethoxybut-1-yne. To a suspension of aluminum (20.87 g, 773 mmol) and mercury(II) chloride (1.187 g, 4.37 mmol) in ether (40 mL) was added triethoxymethane (49.8 g, 336 mmol) in ether (160 mL) over 60 minutes (internal temperature monitored and addition slowed to keep below 41° C.). The mixture was stirred at reflux for one hour, then brought to −78° C. in a dry ice/acetone bath. 3-bromoprop-1-yne (75 g, 504 mmol) in ether (17 mL) was added dropwise and the suspension was stirred at −78° C. for three additional hours. The reaction was quenched with water (300 mL) followed by 1N NaOH (120 mL). The layers were separated and the aqueous layer washed with additional diethyl ether. The organic extracts were dried over magnesium sulfate and concentrated to yield 4,4-diethoxybut-1-yne.

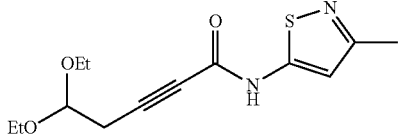 [SMILES: CCOC(CC#CC(=O)Nc1cc(C)ns1)OCC]

5,5-diethoxy-N-(3-methylisothiazol-5-yl)pent-2-ynamide. In a 50-mL round bottom flask under nitrogen was dissolved 4,4-diethoxybut-1-yne (10.14 g, 71.3 mmol) in THF (102 mL), and stirred at −78° C. Butyllithium (30.0 mL, 74.9 mmol) was added dropwise, and after 15 minutes, carbon dioxide (157 g, 3566 mmol) was bubbled through the reaction mixture, as it was warmed to RT for 1 h. The reaction was degassed with argon for 20 minutes to eliminate excess $CO_2$, and was then cooled to 0° C., and neutralized with 3-methylisothiazol-5-amine hydrochloride (12.21 g, 107 mmol). To the reaction mixture was added HATU (35.2 g, 93 mmol) followed by Hunig's Base (37.4 mL, 214 mmol). The reaction was slowly allowed to warm to RT and stirred for 2 h. The reaction mixture was diluted with 1N NaOH (500 mL), and then extracted with small amounts of EtOAc (3×150 mL). The combined organics were extracted with 1N NaOH (500 mL) and the organics were discarded. The basic aqueous layers were combined, neutralized with 2N HCl, and extracted with ether. The organics were dried with sodium sulfate, filtered and concentrated in vacuo to yield crude material contaminated with tetramethylurea, and acetic acid. The acetic acid was removed via dilution with ethyl acetate and subsequent washing with sat. aq. sodium bicarbonate. After washing with sodium bicarbonate, the resulting product was dried with magnesium sulfate, filtered and concentrated in vacuo to yield 5,5-diethoxy-N-(3-methylisothiazol-5-yl)pent-2-ynamide as a dark-red oil.

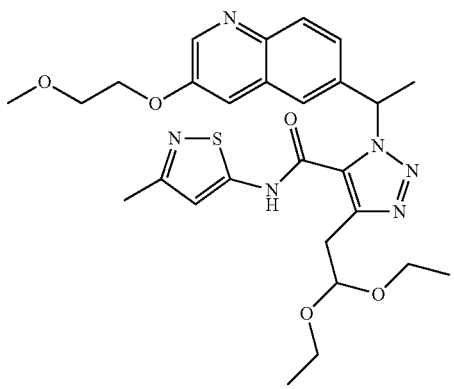 [SMILES: CCOC(Cc1nnn(C(C)c2ccc3ncc(OCCOC)cc3c2)c1C(=O)Nc1cc(C)ns1)OCC]

5-(2,2-diethoxyethyl)-3-(1-(3-(2-methoxyethoxy)quinolin-6-yl)ethyl)-N-(3-methylisothiazol-5-yl)-3H-1,2,3-triazole-4-carboxamide. 5,5-diethoxy-N-(3-methylisothiazol-5-yl)pent-2-ynamide (0.700 g, 2.5 mmol) was dissolved in chlorobenzene (2.5 mL, 2.5 mmol), and to the solution was added 6-(1-azidoethyl)-3-(2-methoxyethoxy)quinoline (0.68 g, 2.5 mmol). The mixture was heated to 100° C. overnight and then increased to 110° C. for 5.5 h. The reaction was concentrated in vacuo. The compound was purified via MPLC (eluting with 0-40% EtOAc in hexanes) to yield 5-(2,2-diethoxyethyl)-3-(1-(3-(2-methoxyethoxy)quinolin-6-yl)ethyl)-N-(3-methylisothiazol-5-yl)-3H-1,2,3-triazole-4-carboxamide.

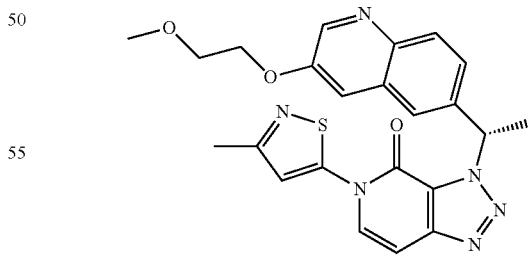

(S)-3-(1-(3-(2-methoxyethoxy)quinolin-6-yl)ethyl)-5-(3-methylisothiazol-5-yl)-3H-[1,2,3]triazolo[4,5-c]pyridin-4(5H)-one. 5-(2,2-diethoxyethyl)-3-(1-(3-(2-methoxyethoxy)quinolin-6-yl)ethyl)-N-(3-methylisothiazol-5-yl)-3H-1,2,3-triazole-4-carboxamide (0.296 g, 0.53 mmol) was dissolved in dichloroethane (5 mL) and to the solution was added p-toluenesulfonic acid monohydrate (0.11 g, 0.59 mmol).

The reaction mixture was heated at 100° C. overnight. The reaction mixture was diluted with dichloromethane then washed with sat. aq. sodium bicarbonate and brine. The organic layer was dried over sodium sulfate and concentrated in vacuo. The enantiomers were separated via preparative SFC (ChiralPak® AD-H, 20×250 mm, 40:60:0.2 IPA:CO2:DEA, 80 mL/min; $t_r$ 1.38 min) to yield (S)-3-(1-(3-(2-methoxyethoxy)quinolin-6-yl)ethyl)-5-(3-methylisothiazol-5-yl)-3H-[1,2,3]triazolo[4,5-c]pyridin-4(5H)-one as a pale yellow solid. On the basis of previous crystallographic data and potency recorded for related compounds in the same program, the absolute stereochemistry was assigned as the S enantiomer. MS m/z=463.2 [M+1]$^+$. Calc'd 462.5 for $C_{23}H_{22}N_6O_3S$. 1H NMR (400 MHz, DMSO-d$_6$) δ ppm 2.15 (d, 3 H) 2.39-2.44 (m, 3 H) 3.30-3.32 (m, 3 H) 3.71 (dd, 2 H) 4.23 (dd, 2 H) 6.89 (q, 1 H) 7.33 (d, 1 H) 7.64 (dd, 1 H) 7.74-7.82 (m, 3 H) 7.94 (d, 1 H) 8.34 (d, 1 H) 8.61 (d, 1 H).

EXAMPLE 15

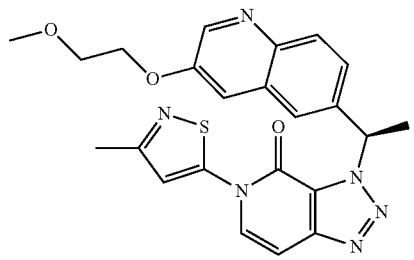 [SMILES: COCCOc1cnc2ccc([C@@H](C)n3nnc4ccn(-c5cc(C)ns5)c(=O)c43)cc2c1]

(R)-3-(1-(3-(2-methoxyethoxy)quinolin-6-yl)ethyl)-5-(3-methylisothiazol-5-yl)-3H-[1,2,3]triazolo[4,5-c]pyridin-4(5H)-one The title compound was synthesized as was (S)-3-(1-(3-(2-methoxyethoxy)quinolin-6-yl)ethyl)-5-(3-methylisothiazol-5-yl)-3H-[1,2,3]triazolo[4,5-c]pyridin-4(5H)-one. Chiral separation via SFC (ChiralPak® AD-H, 20×250 mm, 40:60:0.2 IPA:CO2:DEA, 80 mL/min; $t_r$ 2.26 min) to yield (R)-3-(1-(3-(2-methoxyethoxy)quinolin-6-yl)ethyl)-5-(3-methylisothiazol-5-yl)-3H-[1,2,3]triazolo[4,5-c]pyridin-4(5H)-one. On the basis of previous crystallographic data and potency recorded for related compounds in the same program, the absolute stereochemistry was assigned as the R enantiomer. MS m/z=463.2 [M+1]$^+$. Calc'd 462.5 for $C_{23}H_{22}N_6O_3S$. 1H NMR (400 MHz, CHLOROFORM-d) δ ppm 2.27 (d, J=7.14 Hz, 3 H) 2.53 (s, 3 H) 3.48 (s, 3 H) 3.80-3.88 (m, 2 H) 4.23-4.31 (m, 2 H) 6.95 (q, J=7.17 Hz, 1 H) 7.07-7.13 (m, 2 H) 7.47 (br. s., 1 H) 7.69-7.79 (m, 2 H) 7.90 (d, J=1.37 Hz, 1 H) 8.09 (d, J=8.51 Hz, 1 H) 8.71 (d, J=2.74 Hz, 1 H).

EXAMPLE 16

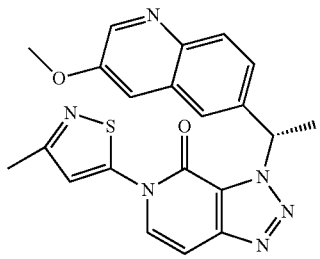 [SMILES: COc1cnc2ccc([C@H](C)n3nnc4ccn(-c5cc(C)ns5)c(=O)c43)cc2c1]

(S)-3-(1-(3-methoxyquinolin-6-yl)ethyl)-5-(3-methylisothiazol-5-yl)-3H-[1,2,3]triazolo[4,5-c]pyridin-4(5H)-one The title compound was synthesized according to General Method E. The azide was synthesized in similar fashion to 6-(1-azidoethyl)-3-(2-methoxyethoxy)quinoline. The enantiomers were separated via preparative SFC (ChiralPak® AS-H, 20×250 mm, 30:70 MeOH:CO2, 80 mL/min; $t_r$ 0.84 min) to yield (S)-3-(1-(3-methoxyquinolin-6-yl)ethyl)-5-(3-methylisothiazol-5-yl)-3H-[1,2,3]triazolo[4,5-c]pyridin-4(5H)-one. On the basis of previous crystallographic data and potency recorded for related compounds in the same program, the absolute stereochemistry was assigned as the S enantiomer. MS m/z=419.2 [M+1]$^+$. Calc'd 418.5 for $C_{21}H_{18}N_6O_2S$. 1H NMR (400 MHz, DMSO-d$_6$) δ ppm 2.16 (d, J=7.14 Hz, 3 H) 2.42 (s, 3 H) 3.90 (s, 3 H) 6.89 (q, J=7.04 Hz, 1 H) 7.31 (d, J=7.73 Hz, 1 H) 7.63 (dd, J=8.75, 2.10 Hz, 1 H) 7.77 (s, 1 H) 7.80 (d, J=1.96 Hz, 2 H) 7.95 (d, J=8.71 Hz, 1 H) 8.32 (d, J=7.92 Hz, 1 H) 8.61 (d, J=2.93 Hz, 1 H).

EXAMPLE 17

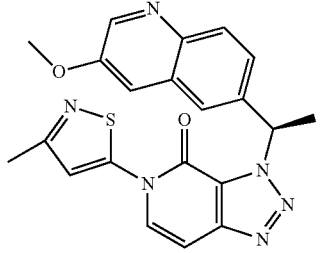 [SMILES: COc1cnc2ccc([C@@H](C)n3nnc4ccn(-c5cc(C)ns5)c(=O)c43)cc2c1]

(R)-3-(1-(3-methoxyquinolin-6-yl)ethyl)-5-(3-methylisothiazol-5-yl)-3H-[1,2,3]triazolo[4,5-c]pyridin-4(5H)-one The title compound was synthesized as was (S)-3-(1-(3-methoxyquinolin-6-yl)ethyl)-5-(3-methylisothiazol-5-yl)-3H-[1,2,3]triazolo[4,5-c]pyridin-4(5H)-one. Chiral separation via preparative SFC (ChiralPak® AS-H, 20×250 mm, 30:70 MeOH:CO2, 80 mL/min; $t_r$ 1.11 min) to yield (R)-3-(1-(3-methoxyquinolin-6-yl)ethyl)-5-(3-methylisothiazol-5- yl)-3H-[1,2,3]triazolo[4,5-c]pyridin-4(5H)-one. On the basis of previous crystallographic data and potency recorded for related compounds in the same program, the absolute stereochemistry was assigned as the R enantiomer. MS m/z=419.1 [M+1]$^+$. Calc'd 418.5 for $C_{21}H_{18}N_6O_2S$. 1H NMR (400 MHz, DMSO-d$_6$) δ ppm 2.16 (d, 3 H) 2.43 (d, J=1.47 Hz, 3 H) 3.90 (d, J=1.47 Hz, 3 H) 6.90 (q, 1 H) 7.31 (dd, J=7.73, 1.57 Hz, 1 H) 7.60-7.66 (m, 1 H) 7.75-7.81 (m, 3 H) 7.94 (d, 1 H) 8.32 (dd, J=7.63, 1.37 Hz, 1 H) 8.60-8.63 (m, 1 H).

EXAMPLE 18

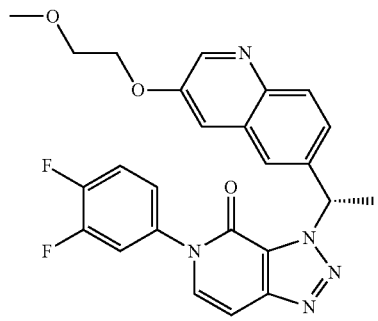 [SMILES: COCCOc1cnc2ccc([C@H](C)n3nnc4ccn(-c5ccc(F)c(F)c5)c(=O)c43)cc2c1]

(S)-5-(3,4-difluorophenyl)-3-(1-(3-(2-methoxyethoxy)quinolin-6-yl)ethyl)-3H-[1,2,3]triazolo[4,5-c]pyridin-4(5H)-one

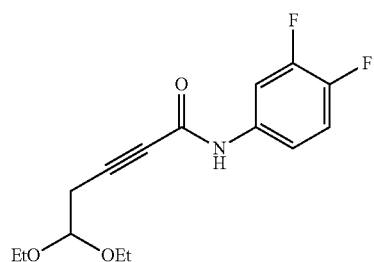 [SMILES: CCOC(CC#CC(=O)Nc1ccc(F)c(F)c1)OCC]

1) N-(3,4-difluorophenyl)-5,5-diethoxypent-2-ynamide. 4,4-diethoxybut-1-yne (0.300 g, 2.1 mmol) was dissolved in THF (3.0 mL, 2.1 mmol), and cooled to −78° C. To the solution was added BuLi (2.5 M in hexanes) (1.1 mL, 2.6 mmol) dropwise, and then the reaction was allowed to stir at −78° C. for 30 minutes. A solution of 1,2-difluoro-4-isocyanatobenzene (0.54 mL, 4.6 mmol) in THF (0.48 mL, 2.1 mmol) was then added dropwise to the anion and the reaction was complete in 20 minutes. The reaction was quenched to near neutral pH with sat. aq. NH$_4$Cl, and warmed to RT. The mixture was diluted with DCM and washed with water and brine. The organic layers were dried over sodium sulfate and concentrated in vacuo. The crude material was purified via MPLC (0-100% EtOAc in hexanes) to yield N-(3,4-difluorophenyl)-5,5-diethoxypent-2-ynamide as a dark-red oil.

2)

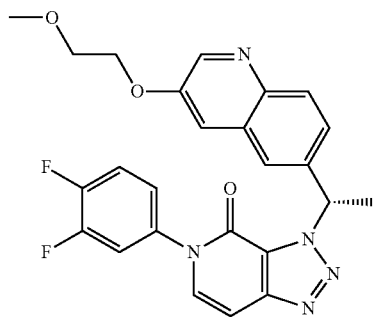 [SMILES: COCCOc1cnc2ccc([C@H](C)n3nnc4ccn(-c5ccc(F)c(F)c5)c(=O)c43)cc2c1]

3) (S)-5-(3,4-difluorophenyl)-3-(1-(3-(2-methoxyethoxy)quinolin-6-yl)ethyl)-3H-[1,2,3]triazolo[4,5-c]pyridin-4(5H)-one. The title compound was prepared according to General Method E. The enantiomers were separated via preparative SFC (ChiralPak® AD-H, 3×15 cm, 25% methanol w/ 0.2% DEA, 70 mL/min; t$_r$ 5.32 min) to yield (S)-5-(3,4-difluorophenyl)-3-(1-(3-(2-methoxyethoxy)quinolin-6-yl)ethyl)-3H-[1,2,3]triazolo[4,5-c]pyridin-4(5H)-one. On the basis of previous crystallographic data and potency recorded for related compounds in the same program, the absolute stereochemistry was assigned as the S enantiomer. MS m/z=478.2 [M+1]$^+$. Calc'd 477.5 for $C_{25}H_{21}F_2N_5O_3$. 1H NMR (400 MHz, DMSO-d$_6$) ppm 2.13 (d, J=7.04 Hz, 3 H) 3.32 (s, 3 H) 3.70-3.74 (m, 2 H) 4.24 (dd, 2 H) 6.84 (q, 1 H) 7.00 (d, J=7.43 Hz, 1 H) 7.32-7.38 (m, 1 H) 7.52 (d, J=7.43 Hz, 1 H) 7.58-7.63 (m, 2 H) 7.68-7.75 (m, 1 H) 7.79-7.82 (m, 2 H) 7.92 (d, J=8.71 Hz, 1 H) 8.62 (d, J=2.93 Hz, 1 H).

EXAMPLE 19

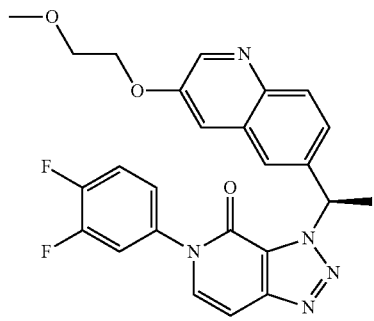 [SMILES: COCCOc1cnc2ccc([C@@H](C)n3nnc4ccn(-c5ccc(F)c(F)c5)c(=O)c43)cc2c1]

(R)-5-(3,4-difluorophenyl)-3-(1-(3-(2-methoxyethoxy)quinolin-6-yl)ethyl)-3H-[1,2,3]triazolo[4,5-c]pyridin-4(5H)-one The title compound was synthesized as was (S)-5-(3,4-difluorophenyl)-3-(1-(3-(2-methoxyethoxy)quinolin-6-yl)ethyl)-3H-[1,2,3]triazolo[4,5-c]pyridin-4(5H)-one. Chiral separation via SFC (ChiralPak® AD-H, 3×15 cm, 25% methanol w/ 0.2% DEA, 70 ml/min; t$_r$ 6.40 min) to yield (R)-5-(3,4-difluorophenyl)-3-(1-(3-(2-methoxyethoxy)quinolin-6-yl)ethyl)-3H-[1,2,3]triazolo[4,5-c]pyridin-4(5H)-one. On the basis of previous crystallographic data and potency recorded for related compounds in the same program, the absolute stereochemistry was assigned as the R enantiomer. MS m/z=478.2 [M+1]⁺. Calc'd 477.5 for $C_{25}H_{21}F_2N_5O_3$. 1H NMR (400 MHz, DMSO-$d_6$) δ ppm 2.14 (d, 3 H) 3.32 (s, 3 H) 3.69-3.75 (m, 2 H) 4.21-4.27 (m, 2 H) 6.79-6.89 (m, 1 H) 7.00 (d, J=7.43 Hz, 1 H) 7.32-7.40 (m, 1 H) 7.52 (d, J=7.53 Hz, 1 H) 7.56-7.64 (m, 2 H) 7.67-7.75 (m, 1 H) 7.78-7.82 (m, 2 H) 7.91 (d, 1 H) 8.62 (d, J=2.74 Hz, 1 H).

EXAMPLE 20

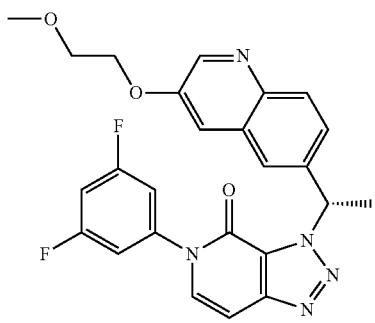 [SMILES: COCCOc1cnc2ccc([C@H](C)n3nnc4ccn(-c5cc(F)cc(F)c5)c(=O)c43)cc2c1]

(S)-5-(3,5-difluorophenyl)-3-(1-(3-(2-methoxyethoxy)quinolin-6-yl)ethyl)-3H-[1,2,3]triazolo[4,5-c]pyridin-4(5H)-one The title compound was prepared according to General Method E. The amide starting material was synthesized in a similar fashion as N-(3,4-difluorophenyl)-5,5-diethoxypent-2-ynamide. The enantiomers were separated via preparative SFC (ChiralPak® AD-H, 3×15 cm, 35% ethanol w/ 0.2% DEA, 70 mL/min; $t_r$ 2.62 min) to yield (S)-5-(3,5-difluorophenyl)-3-(1-(3-(2-methoxyethoxy)quinolin-6-yl)ethyl)-3H-[1,2,3]triazolo[4,5-c]pyridin-4(5H)-one. On the basis of previous crystallographic data and potency recorded for related compounds in the same program, the absolute stereochemistry was assigned as the S enantiomer. MS m/z=478.5 [M+1]⁺. Calc'd 477.5 for $C_{25}H_{21}F_2N_5O_3$. 1H NMR (400 MHz, DMSO-$d_6$) δ ppm 2.13 (d, J=7.04 Hz, 3 H) 3.32 (s, 3 H) 3.69-3.74 (m, 2 H) 4.22-4.26 (m, 2 H) 6.83 (q, 1 H) 7.02 (d, J=7.43 Hz, 1 H) 7.36 (dd, J=7.87, 2.30 Hz, 2 H) 7.40-7.47 (m, 1 H) 7.55 (d, J=7.43 Hz, 1 H) 7.60 (dd, J=8.66, 2.01 Hz, 1 H) 7.79-7.82 (m, 2 H) 7.93 (d, J=8.71 Hz, 1 H) 8.62 (d, J=2.93 Hz, 1 H).

EXAMPLE 21

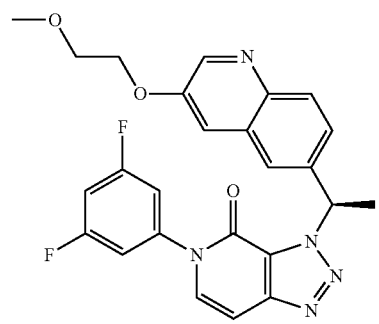 [SMILES: COCCOc1cnc2ccc([C@@H](C)n3nnc4ccn(-c5cc(F)cc(F)c5)c(=O)c43)cc2c1]

(R)-5-(3,5-difluorophenyl)-3-(1-(3-(2-methoxyethoxy)quinolin-6-yl)ethyl)-3H-[1,2,3]triazolo[4,5-c]pyridin-4(5H)-one The title compound was synthesized as was (S)-5-(3,5-difluorophenyl)-3-(1-(3-(2-methoxyethoxy)quinolin-6-yl)ethyl)-3H-[1,2,3]triazolo[4,5-c]pyridin-4(5H)-one. Chiral separation via SFC (ChiralPak® AD-H, 3×15 cm, 35% ethanol w/ 0.2% DEA, 70 mL/min; $t_r$ 3.57 min) to yield (R)-5-(3,5-difluorophenyl)-3-(1-(3-(2-methoxyethoxy)quinolin-6-yl)ethyl)-3H-[1,2,3]triazolo[4,5-c]pyridin-4(5H)-one. On the basis of previous crystallographic data and potency recorded for related compounds in the same program, the absolute stereochemistry was assigned as the R enantiomer. MS m/z=478.2 [M+1]⁺. Calc'd 477.5 for $C_{25}H_{21}F_2N_5O_3$. 1H NMR (400 MHz, DMSO-$d_6$) δ ppm 2.13 (d, J=7.14 Hz, 3H) 3.32 (s, 3H) 3.65-3.76 (m, 2 H) 4.24 (dd, J=6.16, 3.03 Hz, 2 H) 6.84 (q, J=6.75 Hz, 1 H) 7.02 (d, J=7.43 Hz, 1 H) 7.36 (dd, J=7.87, 2.20 Hz, 2 H) 7.40-7.47 (m, 1 H) 7.55 (d, J=7.43 Hz, 1 H) 7.60 (dd, J=8.61, 2.05 Hz, 1 H) 7.77-7.83 (m, 2 H) 7.92 (d, 1 H) 8.62 (d, J=2.93 Hz, 1 H).

EXAMPLE 22

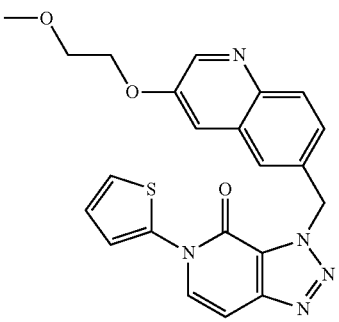 [SMILES: COCCOc1cnc2ccc(Cn3nnc4ccn(-c5cccs5)c(=O)c43)cc2c1]

3-((3-(2-methoxyethoxy)quinolin-6-yl)methyl)-5-(thiophen-2-yl)-3H-[1,2,3]triazolo[4,5-c]pyridin-4(5H)-one

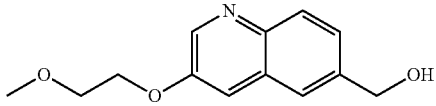 [SMILES: COCCOc1cnc2ccc(CO)cc2c1]

1) (3-(2-methoxyethoxy)quinolin-6-yl)methanol. In a 1 L round bottom flask under N$_2$ was dissolved 3-(2-methoxyethoxy)quinoline-6-carbaldehyde (17.3 g, 74.8 mmol) and in portions, sodium borohydride (2.83 g, 74.8 mmol) in EtOH (500 mL) was added at 0° C. After 3 h the reaction was complete. The reaction mixture was diluted with DCM then neutralized with H$_2$O. The aqueous phase was extracted (×3) with DCM then the organic layer was dried over Na$_2$SO$_4$, filtered and concentrated under reduced pressure. The crude mixture was purified by silica plug with 100% EtOAc to afford (3-(2-methoxyethoxy)quinolin-6-yl)methanol as an off-white solid.

2)

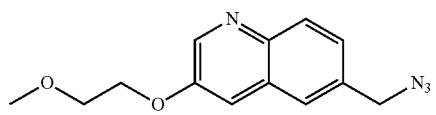 [SMILES: COCCOc1cnc2ccc(CN=[N+]=[N-])cc2c1]

3) 6-(azidomethyl)-3-(2-methoxyethoxy)quinoline. In a 250-mL round bottom flask under N$_2$ was dissolved (3-(2-methoxyethoxy)quinolin-6-yl)methanol (11.66 g, 50.0 mmol) in toluene (100 mL) then DBU (9.04 mL, 60.0 mmol) and 4 Å molecular sieves (12 g) were added, followed by a slow addition of DPPA (12.9 mL, 60.0 mmol) at 0° C. After the addition, the reaction was warmed to RT and stirred for 10 h. The reaction mixture was diluted with DCM then neutralized with H$_2$O. The aqueous phase was extracted with DCM (×3) then the organic layer was dried over Na$_2$SO$_4$, filtered and concentrated under reduced pressure. The crude mixture was purified by MPLC with Hexanes:EtOAc 100:0 to 0:100 to afford 6-(azidomethyl)-3-(2-methoxyethoxy)quinoline.

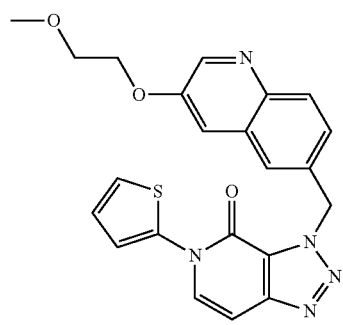 [SMILES: COCCOc1cnc2ccc(Cn3nnc4ccn(-c5cccs5)c(=O)c43)cc2c1]

4) 3-((3-(2-methoxyethoxy)quinolin-6-yl)methyl)-5-(thiophen-2-yl)-3H-[1,2,3]triazolo[4,5-c]pyridin-4(5H)-one. The title compound was synthesized according to General Method E. The amide starting material was synthesized in a similar fashion as N-(3,4-difluorophenyl)-5,5-diethoxypent-2-ynamide. MS m/z=434.2 [M+1]$^+$. Calc'd 433.5 for C$_{22}$H$_{19}$N$_5$O$_3$S. 1H NMR (400 MHz, DMSO-d$_6$) δ ppm 3.32 (s, 3 H) 3.70-3.74 (m, 2 H) 4.20-4.26 (m, 2 H) 6.24 (s, 2 H) 7.06-7.11 (m, 2 H) 7.35 (dd, J=3.81, 1.47 Hz, 1 H) 7.55 (dd, J=5.48, 1.47 Hz, 1 H) 7.58 (dd, J=8.66, 2.01 Hz, 1 H) 7.75 (dd, J=18.44, 2.10 Hz, 2 H) 7.83 (d, J=7.63 Hz, 1 H) 7.94 (d, J=8.61 Hz, 1 H) 8.63 (d, J=2.93 Hz, 1 H).

EXAMPLE 23

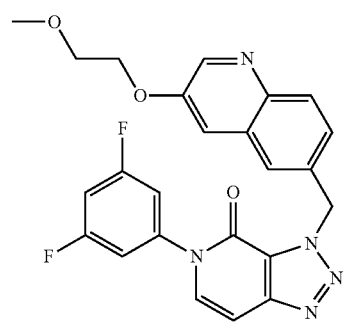 [SMILES: COCCOc1cnc2ccc(Cn3nnc4ccn(-c5cc(F)cc(F)c5)c(=O)c43)cc2c1]

5-(3,5-difluorophenyl)-3-((3-(2-methoxyethoxy)quinolin-6-yl)methyl)-3H-[1,2,3]triazolo[4,5-c]pyridin-4(5H)-one The title compound was synthesized according to General Method E. MS m/z=464.1 [M+1]$^+$. Calc'd 463.4 for C$_{24}$H$_{19}$F$_2$N$_5$O$_3$. 1H NMR (400 MHz, DMSO-d$_6$) δ ppm 3.32 (s, 3 H) 3.70-3.75 (m, 2 H) 4.22-4.27 (m, 2 H) 6.21 (s, 2 H) 7.03 (d, J=7.43 Hz, 1 H) 7.34-7.49 (m, 3 H) 7.55-7.61 (m, 2 H) 7.77-7.81 (m, 2 H) 7.92 (d, 1 H) 8.63 (d, J=2.84 Hz, 1 H).

EXAMPLE 24

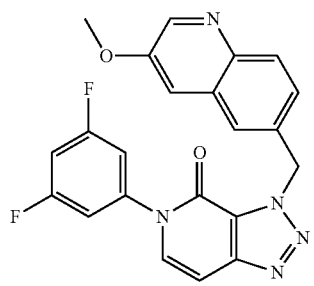 [SMILES: COc1cnc2ccc(Cn3nnc4ccn(-c5cc(F)cc(F)c5)c(=O)c43)cc2c1]

5-(3,5-difluorophenyl)-3-((3-methoxyquinolin-6-yl)methyl)-3H-[1,2,3]triazolo[4,5-c]pyridin-4(5H)-one The title compound was synthesized according to General Method E. MS m/z=420.2 [M+1]$^+$. Calc'd 419.4 for C$_{22}$H$_{15}$F$_2$N$_5$O$_2$. 1H NMR (400 MHz, DMSO-d$_6$) δ ppm 3.90 (s, 3 H) 6.22 (s, 2 H) 7.03 (d, J=7.43 Hz, 1 H) 7.35-7.48 (m, 3 H) 7.55-7.61 (m, 2 H) 7.79 (dd, J=17.75, 2.20 Hz, 2 H) 7.94 (d, J=8.61 Hz, 1 H) 8.62 (d, J=2.93 Hz, 1 H).

EXAMPLE 25

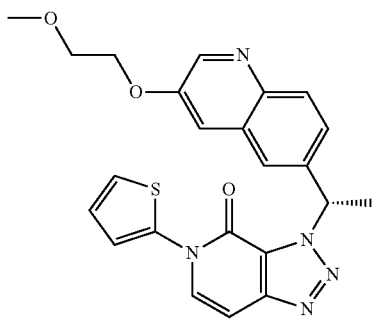 [SMILES: COCCOc1cnc2ccc([C@H](C)n3nnc4ccn(-c5cccs5)c(=O)c43)cc2c1]

(S)-3-(1-(3-(2-methoxyethoxy)quinolin-6-yl)ethyl)-5-(thiophen-2-yl)-3H-[1,2,3]triazolo[4,5-c]pyridin-4(5H)-one The title compound was synthesized according to General Method E. The enantiomers were separated via preparative SFC (ChiralPak® AD-H, 2×15 cm, 45% methanol w/ 0.1% DEA, 65 mL/min; $t_r$ 4.59 min) to yield (S)-3-(1-(3-(2-methoxyethoxy)quinolin-6-yl)ethyl)-5-(thiophen-2-yl)-3H-[1,2,3]triazolo[4,5-c]pyridin-4(5H)-one. On the basis of previous crystallographic data and potency recorded for related compounds in the same program, the absolute stereochemistry was assigned as the S enantiomer. MS m/z=448.2 [M+1]$^+$. Calc'd 447.5 for $C_{23}H_{21}N_5O_3S$. 1H NMR (400 MHz, DMSO-$d_6$) δ ppm 2.13 (d, J=7.14 Hz, 3H) 3.32 (s, 3 H) 3.67-3.75 (m, 2 H) 4.21-4.26 (m, 2 H) 6.85 (q, 1 H) 7.04-7.10 (m, 2 H) 7.31 (dd, J=3.86, 1.42 Hz, 1 H) 7.55 (dd, J=5.53, 1.42 Hz, 1 H) 7.60 (dd, J=8.80, 2.05 Hz, 1 H) 7.76 (d, J=1.96 Hz, 1 H) 7.78-7.82 (m, 2 H) 7.93 (d, J=8.71 Hz, 1 H) 8.62 (d, J=2.93 Hz, 1 H).

EXAMPLE 26

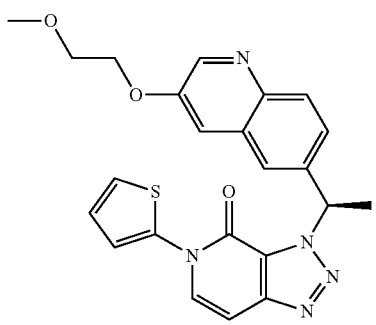 [SMILES: COCCOc1cnc2ccc([C@@H](C)n3nnc4ccn(-c5cccs5)c(=O)c43)cc2c1]

(R)-3-(1-(3-(2-methoxyethoxy)quinolin-6-yl)ethyl)-5-(thiophen-2-yl)-3H-[1,2,3]triazolo[4,5-c]pyridin-4(5H)-one The title compound was synthesized as was (S)-3-(1-(3-(2-methoxyethoxy)quinolin-6-yl)ethyl)-5-(thiophen-2-yl)-3H-[1,2,3]triazolo[4,5-c]pyridin-4(5H)-one. Chiral separation via preparative SFC (ChiralPak® AD-H, 2×15 cm, 45% methanol w/ 0.1% DEA, 65 mL/min; $t_r$ 6.74 min) to yield (R)-3-(1-(3-(2-methoxyethoxy)quinolin-6-yl)ethyl)-5-(thiophen-2-yl)-3H-[1,2,3]triazolo[4,5-c]pyridin-4(5H)-one. On the basis of previous crystallographic data and potency recorded for related compounds in the same program, the absolute stereochemistry was assigned as the R enantiomer. MS m/z=448.2 [M+1]$^+$. Calc'd 447.5 for $C_{23}H_{21}N_5O_3S$. 1H NMR (400 MHz, DMSO-$d_6$) δ ppm 2.13 (d, J=7.14 Hz, 3 H) 3.32 (s, 3 H) 3.68-3.74 (m, 2 H) 4.23 (dd, J=3.67, 2.40 Hz, 2 H) 6.85 (q, 1 H) 7.05-7.09 (m, 2 H) 7.31 (dd, J=3.86, 1.42 Hz, 1 H) 7.55 (dd, J=5.58, 1.47 Hz, 1 H) 7.60 (dd, J=8.75, 2.10 Hz, 1 H) 7.76 (d, J=1.96 Hz, 1 H) 7.78-7.82 (m, 2 H) 7.93 (d, J=8.71 Hz, 1 H) 8.62 (d, J=2.93 Hz, 1 H).

EXAMPLE 27

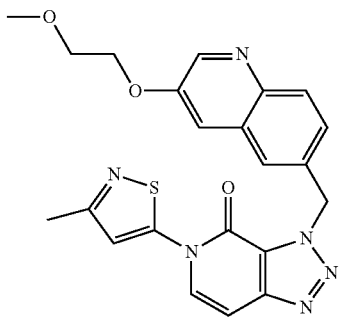 [SMILES: COCCOc1cnc2ccc(Cn3nnc4ccn(-c5cc(C)ns5)c(=O)c43)cc2c1]

3-((3-(2-methoxyethoxy)quinolin-6-yl)methyl)-5-(3-methylisothiazol-5-yl)-3H-[1,2,3]triazolo[4,5-c]pyridin-4(5H)-one The title compound was synthesized according to General Method B, using 6-(azidomethyl)-3-(2-methoxyethoxy)quinoline. MS m/z=449.1 [M+1]$^+$. Calc'd 448.5 for $C_{22}H_{20}N_6O_3S$.

EXAMPLE 28

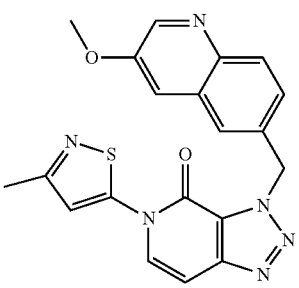 [SMILES: COc1cnc2ccc(Cn3nnc4ccn(-c5cc(C)ns5)c(=O)c43)cc2c1]

3-((3-methoxyquinolin-6-yl)methyl)-5-(3-methyl-isothiazol-5-yl)-3H-[1,2,3]triazolo[4,5-c]pyridin-4(5H)-one The title compound was synthesized according to General Method E, using 6-(azidomethyl)-3-(2-methoxy)quinoline. MS m/z=405.2 [M+1]$^+$. Calc'd 404.4 for $C_{20}H_{16}N_6O_2S$.

EXAMPLE 29

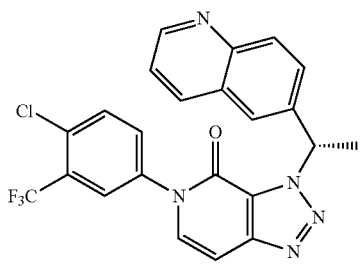 [SMILES: C[C@@H](c1ccc2ncccc2c1)n1nnc2ccn(-c3ccc(Cl)c(C(F)(F)F)c3)c(=O)c21]

(S)-5-(4-chloro-3-(trifluoro methyl)phenyl)-3-(1-(quinolin-6-yl)ethyl)-3H-[1,2,3]triazolo[4,5-c]pyridin-4(5H)-one The title compound was synthesized according to General Method E, using 6-(1-azidoethyl)quinoline. The enantiomers were separated via preparative SFC (ChiralPak®, 30% isopropanol w/ 0.2% diethylamine, $t_r$ 1.22 min) to yield (S)-5-(4-chloro-3-(trifluoromethyl)phenyl)-3-(1-(quinolin-6-yl)ethyl)-3H-[1,2,3]triazolo[4,5-c]pyridin-4(5H)-one. On the basis of previous crystallographic data and potency recorded for related compounds in the same program, the absolute stereochemistry was assigned as the S enantiomer. MS m/z=470.0 [M+1]$^+$. Calc'd 469.1 for $C_{23}H_{15}ClF_3N_5O$. 1H NMR (400 MHz, CHLOROFORM-d) ppm 2.26 (d, J=7.14 Hz, 3 H) 6.91 (q, J=7.21 Hz, 1 H) 6.97 (d, J=7.43 Hz, 1 H) 7.13 (d, J=7.43 Hz, 1 H) 7.42 (dd, J=8.31, 4.21 Hz, 1 H) 7.50-7.55 (m, 1 H) 7.67 (d, J=8.51 Hz, 1 H) 7.72 (d, J=2.54 Hz, 1 H) 7.89 (dd, J=8.80, 2.05 Hz, 1 H) 7.95 (d, J=1.86 Hz, 1 H) 8.12 (d, J=8.61 Hz, 1 H) 8.18 (d, J=7.82 Hz, 1 H) 8.91 (dd, J=4.30, 1.76 Hz, 1 H).

EXAMPLE 30

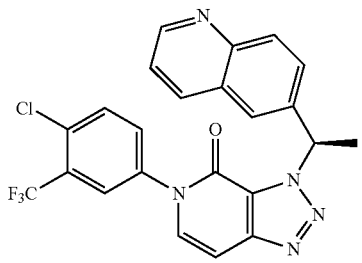 [SMILES: C[C@H](c1ccc2ncccc2c1)n1nnc2ccn(-c3ccc(Cl)c(C(F)(F)F)c3)c(=O)c21]

(R)-5-(4-chloro-3-(trifluoromethyl)phenyl)-3-(1-(quinolin-6-yl)ethyl)-3H-[1,2,3]triazolo[4,5-c]pyridin-4(5H)-one The title compound was synthesized as described for (S)-5-(4-chloro-3-(trifluoromethyl)phenyl)-3-(1-(quinolin-6-yl)ethyl)-3H-[1,2,3]triazolo[4,5-c]pyridin-4(5H)-one. The enantiomers were separated via preparative SFC (ChiralPak®, 30% isopropanol w/ 0.2% diethylamine, $t_r$ 0.98 min) to yield (R)-5-(4-chloro-3-(trifluoromethyl)phenyl)-3-(1-(quinolin-6-yl)ethyl)-3H-[1,2,3]triazolo[4,5-c]pyridin-4(5H)-one. On the basis of previous crystallographic data and potency recorded for related compounds in the same program, the absolute stereochemistry was assigned as the R enantiomer. MS m/z=470.2 [M+1]$^+$. Calc'd 469.1 for $C_{23}H_{15}ClF_3N_5O$. 1H NMR (400 MHz, CHLOROFORM-d) d ppm 2.26 (d, J=7.24 Hz, 3 H) 6.91 (q, J=7.14 Hz, 1 H) 6.97 (d, J=7.43 Hz, 1 H) 7.13 (d, J=7.43 Hz, 1 H) 7.41 (dd, J=8.31, 4.30 Hz, 1 H) 7.52 (dd, J=8.51, 2.54 Hz, 1 H) 7.67 (d, J=8.51 Hz, 1 H) 7.72 (d, J=2.54 Hz, 1 H) 7.88 (dd, J=8.75, 2.10 Hz, 1 H) 7.94 (d, J=1.96 Hz, 1 H) 8.10 (d, J=8.80 Hz, 1 H) 8.16 (dd, J=8.41, 0.98 Hz, 1 H) 8.91 (dd, J=4.21, 1.76 Hz, 1 H).

EXAMPLE 31

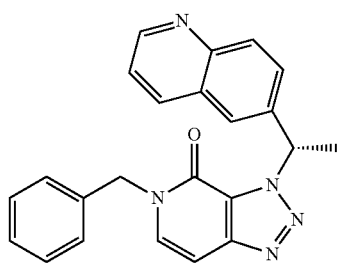 [SMILES: C[C@@H](c1ccc2ncccc2c1)n1nnc2ccn(Cc3ccccc3)c(=O)c21]

(S)-5-benzyl-3-(1-(quinolin-6-yl)ethyl)-3H-[1,2,3]triazolo[4,5-c]pyridin-4(5H)-one The title compound was synthesized according to General Method E, using 6-(1-azidoethyl)quinoline. The enantiomers were separated via preparative SFC (ChiralPak®, 25% methanol w/ 0.2% diethylamine, $t_r$ 1.07 min) to yield (S)-5-benzyl-3-(1-(quinolin-6-yl)ethyl)-3H-[1,2,3]triazolo[4,5-c]pyridin-4(5H)-one. On the basis of previous crystallographic data and potency recorded for related compounds in the same program, the absolute stereochemistry was assigned as the S enantiomer. MS m/z=382.2 [M+1]$^+$. Calc'd 381.4 for $C_{23}H_{19}N_5O$.

EXAMPLE 32

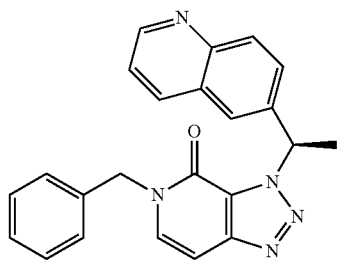 [SMILES: C[C@H](c1ccc2ncccc2c1)n1nnc2ccn(Cc3ccccc3)c(=O)c21]

(R)-5-benzyl-3-(1-(quinolin-6-yl)ethyl)-3H-[1,2,3]triazolo[4,5-c]pyridin-4(5H)-one The title compound was synthesized as described for (S)-5-benzyl-3-(1-(quinolin-6-yl)ethyl)-3H-[1,2,3]triazolo[4,5- c]pyridin-4(5H)-one. The enantiomers were separated via preparative SFC (ChiralPak®, 25% methanol w/ 0.2% diethylamine, $t_r$ 0.88 min) to yield (R)-5-benzyl-3-(1-(quinolin-6-yl)ethyl)-3H-[1,2,3]triazolo[4,5-c]pyridin-4(5H)-one. On the basis of previous crystallographic data and potency recorded for related compounds in the same program, the absolute stereochemistry was assigned as the R enantiomer. MS m/z=382.2 [M+1]$^+$. Calc'd 381.4 for $C_{23}H_{19}N_5O$.

EXAMPLE 33

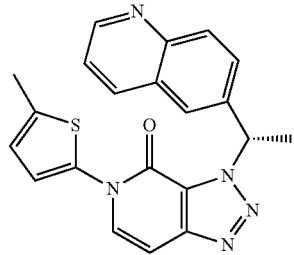 [SMILES: Cc1ccc(-n2ccc3nnn([C@@H](C)c4ccc5ncccc5c4)c3c2=O)s1]

(S)-5-(5-methylthiophen-2-yl)-3-(1-(quinolin-6-yl)ethyl)-3H-[1,2,3]triazolo[4,5-c]pyridin-4(5H)-one The title compound was synthesized according to General Method E, using 6-(1-azidoethyl)quinoline. The enantiomers were separated via preparative SFC (ChiralPak®, 40% methanol w/ 0.2% diethylamine, $t_r$ 1.43 min) to yield (S)-5-(5-methylthiophen-2-yl)-3-(1-(quinolin-6-yl)ethyl)-3H-[1,2,3]triazolo[4,5-c]pyridin-4(5H)-one. On the basis of previous crystallographic data and potency recorded for related compounds in the same program, the absolute stereochemistry was assigned as the S enantiomer. MS m/z=388.2 [M+1]$^+$. Calc'd 387.4 for $C_{21}H_{17}N_5OS$. 1H NMR (400 MHz, CHLOROFORM-d) d ppm 2.25 (d, J=7.14 Hz, 3 H) 2.51 (d, J=1.08 Hz, 3 H) 6.68 (dq, J=3.67, 1.12 Hz, 1 H) 6.84 (d, J=3.72 Hz, 1 H) 6.89 (d, J=7.53 Hz, 1 H) 6.96 (q, J=7.17 Hz, 1 H) 7.29 (s, 1 H) 7.40 (dd, J=8.31, 4.30 Hz, 1 H) 7.92 (dd, J=8.80, 2.15 Hz, 1 H) 7.98 (d, J=1.96 Hz, 1 H) 8.10 (d, J=8.90 Hz, 1 H) 8.16 (dd, J=8.17, 1.12 Hz, 1 H) 8.90 (dd, J=4.25, 1.71 Hz, 1 H).

EXAMPLE 34

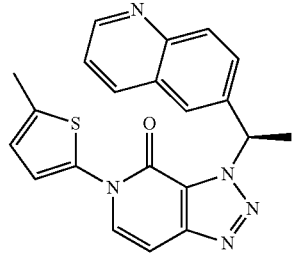 [SMILES: Cc1ccc(-n2ccc3nnn([C@H](C)c4ccc5ncccc5c4)c3c2=O)s1]

(R)-5-(5-methylthiophen-2-yl)-3-(1-(quinolin-6-yl)ethyl)-3H-[1,2,3]triazolo[4,5-c]pyridin-4(5H)-one The title compound was synthesized as described for (S)-5-(5-methylthiophen-2-yl)-3-(1-(quinolin-6-yl)ethyl)-3H-[1,2,3]triazolo[4,5-c]pyridin-4(5H)-one. The enantiomers were separated via preparative SFC (ChiralPak®, 40% methanol w/ 0.2% diethylamine, $t_r$ 0.78 min) to yield (R)-5-(5-methylthiophen-2-yl)-3-(1-(quinolin-6-yl)ethyl)-3H-[1,2,3]triazolo[4,5-c]pyridin-4(5H)-one. On the basis of previous crystallographic data and potency recorded for related compounds in the same program, the absolute stereochemistry was assigned as the R enantiomer. MS m/z=388.2 [M+1]$^+$. Calc'd 387.4 for $C_{21}H_{17}N_5OS$. 1H NMR (400 MHz, CHLOROFORM-d) d ppm 2.25 (d, J=7.24 Hz, 3 H) 2.51 (d, J=1.08 Hz, 3 H) 6.68 (dq, J=3.67, 1.12 Hz, 1 H) 6.84 (d, J=3.72 Hz, 1 H) 6.89 (d, J=7.43 Hz, 1 H) 6.96 (q, J=7.24 Hz, 1 H) 7.28 (d, J=7.53 Hz, 1 H) 7.42 (dd, J=8.31, 4.30 Hz, 1 H) 7.93 (dd, J=8.75, 2.01 Hz, 1 H) 7.98 (d, J=1.86 Hz, 1 H) 8.09-8.15 (m, 1 H) 8.18 (d, J=7.92 Hz, 1 H) 8.91 (dd, J=4.30, 1.66 Hz, 1 H).

EXAMPLE 35

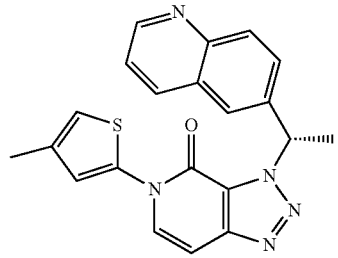 [SMILES: Cc1csc(-n2ccc3nnn([C@@H](C)c4ccc5ncccc5c4)c3c2=O)c1]

(S)-5-(4-methylthiophen-2-yl)-3-(1-(quinolin-6-yl)ethyl)-3H-[1,2,3]triazolo[4,5-c]pyridin-4(5H)-one The title compound was synthesized according to General Method E, using 6-(1-azidoethyl)quinoline. The enantiomers were separated via preparative SFC (ChiralPak®, 40% methanol w/ 0.2% diethylamine, $t_r$ 1.70 min) to yield (S)-5-(4-methylthiophen-2-yl)-3-(1-(quinolin-6-yl)ethyl)-3H-[1,2,3]triazolo[4,5-c]pyridin-4(5H)-one. On the basis of previous crystallographic data and potency recorded for related compounds in the same program, the absolute stereochemistry was assigned as the S enantiomer. MS m/z=388.2 [M+1]$^+$. Calc'd 387.4 for $C_{21}H_{17}N_5OS$. 1H NMR (400 MHz, CHLOROFORM-d) d ppm 2.25 (d, J=7.24 Hz, 3 H) 2.29 (d, J=0.68 Hz, 3 H) 6.87-6.93 (m, 3 H) 6.96 (q, J=7.24 Hz, 1 H) 7.30 (d, J=7.43 Hz, 1 H) 7.40 (dd, J=8.17, 4.16 Hz, 1 H) 7.92 (dd, J=8.80, 2.05 Hz, 1 H) 7.97 (s, 1 H) 8.09 (d, J=8.80 Hz, 1 H) 8.16 (d, J=8.02 Hz, 1 H) 8.91 (br. s., 1 H).

EXAMPLE 36

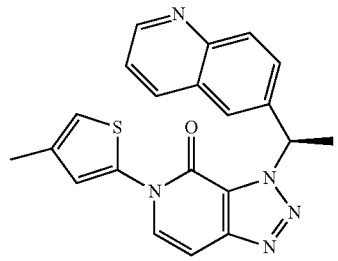 [SMILES: Cc1csc(-n2ccc3nnn([C@H](C)c4ccc5ncccc5c4)c3c2=O)c1]

(R)-5-(4-methylthiophen-2-yl)-3-(1-(quinolin-6-yl)ethyl)-3H-[1,2,3]triazolo[4,5-c]pyridin-4(5H)-one The title compound was synthesized as described for (S)-5-(4-methylthiophen-2-yl)-3-(1-(quinolin-6-yl)ethyl)-3H-[1,2,3]triazolo[4,5-c]pyridin-4(5H)-one. The enantiomers were separated via preparative SFC (ChiralPak®, 40% methanol w/ 0.2% diethylamine, $t_r$ 0.83 min) to yield (R)-5-(4-methylthiophen-2-yl)-3-(1-(quinolin-6-yl)ethyl)-3H-[1,2,3]triazolo[4,5-c]pyridin-4(5H)-one. On the basis of previous crystallographic data and potency recorded for related compounds in the same program, the absolute stereochemistry was assigned as the R enantiomer. MS m/z=388.2 [M+1]$^+$. Calc'd 387.4 for $C_{21}H_{17}N_5OS$. 1H NMR (400 MHz, CHLOROFORM-d) d ppm 2.25 (d, J=7.14 Hz, 3 H) 2.29 (d, J=0.59 Hz, 3 H) 6.88-6.93 (m, 3 H) 6.96 (q, J=7.14 Hz, 1 H) 7.30 (d, J=7.53 Hz, 1 H) 7.41 (dd, J=8.31, 4.21 Hz, 1 H) 7.92 (dd, J=8.80, 2.05 Hz, 1 H) 7.97 (d, J=1.76 Hz, 1 H) 8.08-8.13 (m, 1 H) 8.17 (d, J=8.71 Hz, 1 H) 8.91 (br. s., 1 H).

The efficacy of the compounds of the invention as inhibitors of HGF related activity is demonstrated as follows.

c-Met Receptor Assay

Cloning, Expression and Purification of c-Met Kinase Domain

A PCR product covering residues 1058-1365 of c-Met (c-Met kinase domain) is generated as described in WO06/116,713.

Alternative Purification of Human GST-cMET from Baculovirus Cells

Baculovirus cells were broken in 5× (volume/weight) of Lysis Buffer (50 mM HEPES, pH 8.0, 0.25 M NaCl, 5 mM mercaptoethanol, 10% glycerol plus Complete Protease Inhibitors (Roche (#10019600), 1 tablet per 50 mL buffer). The lysed cell suspension was centrifuged at 100,000×g (29,300 rpm) in a Beckman ultracentrifuge Ti45 rotor for 1 h. The supernatant wa incubated with 10 ml of Glutathione Sepharose 4B from Amersham Biosciences (#27-4574-01). Incubation was carried out overnight in a cold room (approximately 8° C.). The resin and supernatant were poured into an appropriately sized disposable column and the flow through supernatant was collected. The resin was washed with 10 column volumes (100 mL) of Lysis Buffer. The GST-cMET was eluted with 45 mL of 10 mM Glutathione (Sigma #G-4251) in Lysis Buffer. The elution was collected as 15 mL fractions. Aliquots of the elution fractions were run on SDS PAGE (12% Tris Glycine gel, Invitrogen, #EC6005BOX). The gel was stained with 0.25% Coomassie Blue stain. Fractions with GST-cMET were concentrated with a Vivaspin 20 mL Concentrator (#VS2002; 10,00 MW cutoff) to a final volume less than 2.C ml. The concentrated GST-cMET solution was applied to a Superdex 75 16/60 column (Amersham Biosciences #17-1068-01) equilibrated with 25 mM Tris, pH 7.5, 100 mM NaCl, 10 mM mercaptoethanol, 10% glycerol. The GST-cMET was eluted with an isocratic run of the above buffer, with the eluent collected in 1.0 mL fractions. Fractions with significant $OD_{280}$ readings were run on another 12% Tris Glycine gel. The peak tubes with GST-cMET were pooled and the $OD_{280}$ is read with the column buffer listed above as the blank buffer.

Phosphorylation of the purified GST-cMET was performed by incubating the protein for 3 h at RT with the following: 100 mM ATP (Sigma #A7699), 25 mM; 1.0 M $MgCl_2$ (Sigma #M-0250), 100 mM; 200 mM Sodium Orthovanadate (Sigma #S-6508), 15 mM; 1.0 M Tris-HCl, pH 7.00, 50 mM; GST-cMET, 0.2-0.5 mg/mL.

After incubation, the solution was concentrated in a Vivaspin 20 ml Concentrator to a volume less than 2.00 mL. The solution was applied to the same Superdex 75 16/60 column used above after re-equilibration. The GST-cMET was eluted as described above. The elution fractions corresponding to the first eluted peak on the chromatogram were run on a 12% Tris Glycine gel, as above, to identify the fractions with GST-cMET. Fractions were pooled and the $OD_{280}$ is read with the column buffer used as the blank.

A Kinase reaction Buffer was prepared as follows: 60 mM HEPES pH 7.4; 50 mM NaCl; 20 mM $MgCl_2$; 5 mM $MnCl_2$. When the assay was carried out, the following ingredients were freshly added: 2 mM DTT; 0.05% BSA; 0.1 mM $Na_3OV_4$. The HTRF buffer contained: 50 mM Tris-HCl (pH 7.5), 100 mM NaCl, 0.1% BSA, 0.05% Tween 20.5 mM EDTA. Added fresh SA-APC (PJ25S Phycolink Streptavidin-Allophycocyanin Conjugate, Prozyme Inc.) and Eu-PT66 (Eu-W1024 labeled anti-phosphorotyrosine antibody PT66, AD0069, Lot 168465, Perkin-Elmer Inc.) to reach the final concentration: 0.1 nM Eu-PT66; 11 nM SA-APC.

GST-cMet (P) enzyme was diluted in kinase buffer as follows: 8 nM GST-cMet (P) working solution was prepared (7.32 μM to 8 nM, 915 X, 10 μL to 9.15 mL). In a 96 well clear plate [Costar # 3365] added 100 μL in eleven columns, in one column added 100 μL kinase reaction buffer alone.

Assay plate were prepared as follows: Biomek FX was used to transfer 10 μL 8 nM GST-cMet (P) enzyme, 48.4 μL kinase reaction buffer, 1.6 μL compound (in DMSO) (start concentration at 10 mM, 1 mM and 0.1 mM, sequential dilution 1:3 to reach 10 test points) in a 96 well costar clear plate [Costar # 3365], mixed several times. Then incubated the plate at RT for 30 min.

Gastrin and ATP working solution in kinase reaction buffer were prepared as follows: 4 μM Gastrin and 16 μM ATP working solution: Use Biomek FX to add 20 μA ATP and Gastrin working solution to the assay plate to start reaction, incubate the plate at RT for 1 h. 5 μL reaction product was transferred at the end of 1 h into 80 μL HTRF buffer in black plate [Costar # 3356], read on Discover after 30 min incubation.

Assay condition summary: $K_M$ ATP*, 6 μM; [ATP], 4 μM; $K_M$ Gastrin/p(EY), 3.8 μM; gastrin, 1 μM; enzyme, 1 nM. $K_M$ ATP and $K_M$ gastrin for various enzymes were determined by HTRF/$^{33}$P labeling and HTRF methods.

Although the pharmacological properties of the compounds of the current invention vary with structural change, in general, activity possessed by these compounds may be demonstrated in vivo. The pharmacological properties of the compounds of this invention may be confirmed by a number of pharmacological in vitro assays. The exemplified pharmacological assays, which follow, have been carried out with the compounds according to the invention. The exemplified compounds of the present invention demonstrated a $K_i$ shown below in the following table.

| Ex. | cMet $K_i$ (μM) |
| --- | --- |
| 1 | 0.366 |
| 2 | 0.012 |
| 3 | 0.001 |
| 4 | 0.008 |
| 5 | 0.132 |
| 6 | 0.0007 |
| 7 | 0.021 |
| 8 | 0.0015 |
| 9 | 0.242 |

-continued

| Ex. | cMet $K_i$ (µM) |
|---|---|
| 10 | 0.461 |
| 14 | 0.0003 |
| 15 | 0.015 |
| 16 | 0.0006 |
| 17 | 0.030 |
| 18 | 0.0014 |
| 19 | 0.144 |
| 20 | 0.00047 |
| 21 | 0.317 |
| 22 | 0.0057 |
| 23 | 0.0048 |
| 24 | 0.0068 |
| 25 | 0.0015 |
| 26 | 0.218 |
| 27 | 0.0008 |
| 28 | 0.0016 |
| 29 | 0.0034 |
| 30 | 0.473 |
| 31 | 1.088 |
| 32 | 1.309 |
| 33 | 0.004 |
| 34 | 0.872 |
| 35 | 0.004 |
| 36 | 0.269 | c-Met Cell-based Autophosphorylation Assay

Human PC3 and mouse CT26 cells were obtained from ATCC. The cells were cultured in a growth medium containing RPMI 1640, penicillin/streptomycin/glutamine (1×) and 5% FBS. $2\times10^4$ cells in medium were plated per well in a 96 well plate and incubated at 37° C. overnight. The cells were serum-starved by replacing the growth media with basic medium (DMEM low glucose+0.1 BSA, 120 µL per well) at 37° C. for 16 h. Compounds (either 1 mM or 0.2 mM) in 100% DMSO were serially diluted (1:3) 3333 fold on a 96 well plate, diluting 1:3 with DMSO from column 1 to 11 (columns 6 and 12 receive no compound). Compound samples (2.4 µL per well) were diluted with basic medium (240 µL) in a 96 well plate. The cells were washed once with basic medium (GIBCO, DMEM 11885-076) then compound solution was added (100 µL). The cells were incubated at 37° C. for 1 h. A (2 mg/mL) solution of CHO-HGF (7.5 µL) was diluted with 30 mL basic medium to provide a final concentration of 500 ng/mL. This HGF-containing media (120 µL) was transferred to a 96 well plate. Compounds (1.2 µL) was added to the HGF-containing media and mixed well. The mixture of media/HGF/compound (100 µL) was added to the cells (final HGF concentration—250 ng/mL) then incubated at 37° C. for 10 min. A cell lysate buffer (20 mL) was prepared containing 1% Triton X-100, 50 mM Tris pH 8.0, 100 mM NaCl, Protease inhibitor (Sigma, #P-8340) 200 µL, Roche Protease inhibitor (Complete, # 1-697-498) 2 tablets, Phosphatase Inhibitor II (Sigma, #P-5726) 200 µL, and a sodium vanadate solution (containing 900 µL PBS, 100 µL 300 mM $NaVO_3$, 6 µL $H_2O_2$ (30% stock) and stirred at RT for 15 min) (90 µL). The cells were washed once with ice cold 1×PBS (GIBCO, #14190-136), then lysis buffer (60 µL) was added and the cells were incubated on ice for 20 min.

The IGEN assay was performed as follows: Dynabeads M-280 streptavidin beads were pre-incubated with biotinylated anti-human HGFR (240 µL anti-human-HGFR(R&D system, BAF527 or BAF328) at 100 µg/mL+360 µL Beads (IGEN #10029+5.4 µL buffer—PBS/1% BSA/0.1% Tween20) by rotating for 30 min at RT. Antibody beads (25 µL) were transferred to a 96 well plate. Cell lysate solution (25 µL) was transferred added and the plate was shaken at RT for 1 h. Anti-phosphotyrosine 4G10 (Upstate 05-321) (19.7 µL antibody+6 mL 1×PBS) (12.5 µL) was added to each well, then incubated for 1 h at RT. Anti-mouse IgG ORI-Tag (ORIGEN #110087) (24 µL Antibody+6 mL buffer) (12.5 µL) was added to each well, then incubated at RT for 30 min. 1×PBS (175 µL) was added to each well and the electrochemiluminescence was read by an IGEN M8. Raw data was analyzed using a 4-parameter fit equation in XLFit.

rHu-bFGF: Stock concentration of 180 ng/µL: R&D rHu-bFGF: Added 139 µL of the appropriate vehicle above to the 25 µg vial lyophilized vial. 13.3 µL of the [180 ng/µL] stock vial and 26.6 µL of vehicle were added to yield a final concentration of 3.75 µM concentration.

Nitro-cellulose disk preparation: The tip of a 20-gauge needle was cut off square and beveled with emery paper to create a punch. This tip was then used to cut out ≅0.5 mm diameter disks from a nitrocellulose filter paper sheet (Gelman Sciences). Prepared disks were then placed into Eppendorf microfuge tubes containing solutions of either 0.1% BSA in PBS vehicle, 10 µM rHu-VEGF (R&D Systems, Minneapolis, Minn.), or 3.75 µM rHu-bFGF (R&D Systems, Minneapolis, Minn.) and allowed to soak for 45-60 min before use. Each nitrocellulose filter disk absorbs approximately 0.1 µL of solution.

Tumor Models

A431 cells (ATCC) were expanded in culture, harvested and injected subcutaneously into 5-8 week old female nude mice (CD1 nu/nu, Charles River Labs) (n=5-15). Subsequent administration of compound by oral gavage (10-200 mpk/dose) began anywhere from day 0 to day 29 post tumor cell challenge and generally continues either once or twice a day for the duration of the experiment. Progression of tumor growth was followed by three dimensional caliper measurements and recorded as a function of time. Initial statistical analysis was done by repeated measures analysis of variance (RMANOVA), followed by Scheffe post hoc testing for multiple comparisons. Vehicle alone (Ora-Plus, pH 2.0) was the negative control.

Human glioma tumor cells (U87MG cells, ATCC) were expanded in culture, harvested and injected subcutaneously into 5-8 week old female nude mice (CD1 nu/nu, Charles River Labs) (n=10). Subsequent administration of compound by oral gavage or by IP (10-100 mpk/dose) began anywhere from day 0 to day 29 post tumor cell challenge and generally continued either once or twice a day for the duration of the experiment. Progression of tumor growth was followed by three dimensional caliper measurements and recorded as a function of time. Initial statistical analysis was done by repeated measures analysis of variance (RMANOVA), followed by Scheffe post hoc testing for multiple comparisons. Vehicle alone (captisol, or the like) was the negative control.

Human gastric adenocarcinoma tumor cells (MKN45 cells, ATCC) were expanded in culture, harvested and injected subcutaneously into 5-8 week old female nude mice (CD1 nu/nu, Charles River Labs) (n=10). Subsequent administration of compound by oral gavage or by IP (10-100 mpk/dose) began anywhere from day 0 to day 29 post tumor cell challenge and generally continued either once or twice a day for the duration of the experiment. Progression of tumor growth was followed by three dimensional caliper measurements and recorded as a function of time. Initial statistical analysis was done by repeated measures analysis of variance (RMANOVA), followed by Scheffe post hoc testing for multiple comparisons. Vehicle alone (captisol, or the like) wa the negative control Formulations Also embraced within this invention is a class of pharmaceutical compositions comprising the active compounds of the current invention in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, preferably from about 1 to 500 mg. A suitable daily dose for a human or other mammal may vary widely depending on the condition of the patient and other factors, but, once again, can be determined using routine methods.

The amount of compounds which are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, preferably between about 0.01 and about 50 mg/kg, and more preferably about 0.01 and about 30 mg/kg body weight may be appropriate. The daily dose can be administered in one to four doses per day.

For therapeutic purposes, the active compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

In the case of psoriasis and other skin conditions, it may be preferable to apply a topical preparation of compounds of this invention to the affected area two to four times a day.

Formulations suitable for topical administration include liquid or semi-liquid preparations suitable for penetration through the skin (e.g., liniments, lotions, ointments, creams, or pastes) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound, which enhances absorption or penetration of the active ingredient through the skin or other affected areas. Examples of such dermal penetration enhancers include DMSO and related analogs.

The compounds of this invention can also be administered by a transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier, which acts as a stabilizer. In one aspect, it is possible to include both an oil and a fat. Together, the emulsifier(s) with or without stabilizer(s) make-up the so-called emulsifying wax, and the wax together with the oil and fat make up the so-called emulsifying ointment base, which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The active ingredients are preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The foregoing is merely illustrative of the invention and is not intended to limit the invention to the disclosed compounds. Variations and changes, which are obvious to one skilled in the art are intended to be within the scope and nature of the invention, which are defined, in the appended claims.

From the foregoing description, one skilled in the art can easily ascertain the essential characteristics of this invention, and without departing from the spirit and scope thereof, can make various changes and modifications of the invention to adapt it to various usages and conditions.

No unacceptable toxicological effects are expected when compounds of the present invention are administered in accordance with the present invention.

All mentioned references, patents, applications and publications, are hereby incorporated by reference in their entirety.

What is claimed is:

1. A compound of formula I

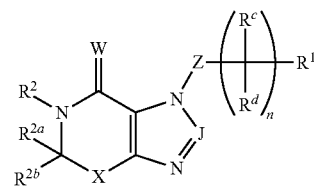

enantiomers, diastereomers, and salts thereof wherein
J is N;
W is O;
X is $CR^{2b*}R^{2c}$,
Z is $CR^aR^b$;
$R^a$ and $R^b$ are independently H or alkyl,
$R^c$ and $R^d$ at each occurrence are independently H,
$R^1$ is aryl or heteroaryl, any of which may be optionally independently substituted with one or more $R_{10}$ groups as allowed by valence;
$R^2$ is selected from phenyl, pyrrolyl, imidazolyl, pyrazolyl, triazolyl, thienyl, oxazolyl, isoxazolyl, thiazolyl, or isothiazolyl, any of which may be optionally independently substituted with one or more $R^{10}$ as allowed by valence;
$R^{2a}$, $R^{2c}$, $R^{2b*}$ are independently selected at each occurence from H, halo and alkyl;
$R^{2b}$ is H or alkyl;
or $R^{2b}$ and $R^{2b*}$ may optionally combine to form a bond,
$R^{10}$ at each occurrence is independently, halo, alkyl, or haloalkyl, and
n is 0.

2. The compound of claim 1 or enantiomers, diastereomers, and salts thereof, wherein $R^1$ is quinolinyl, which may be optionally independently substituted with one or more $R^{10}$ groups as allowed by valence.

3. The compound of claim 1 or enantiomers, diastereomers, and salts thereof, wherein, $R^{2a}$, $R^{2c}$, $R^{2b*}$ are H.

4. The compound of claim 1 or enantiomers, diastereomers, and salts thereof, selected from the group consisting of:
5-phenyl-3-(quinolin-6-ylmethyl)-6,7-dihydro-3H-[1,2,3]triazolo[4,5-c]pyridin-4(5H)-one,
5-(3-methylisothiazol-5-yl)-3-(quinolin-6-ylmethyl)-6,7-dihydro-3H-[1,2,3]triazolo[4,5- c]pyridin-4(5H)-one,
5-(3-methylisothiazol-5-yl)-3-(quinolin-6-ylmethyl)-3H-[1,2,3]triazolo[4,5-c]pyridin-4(5H)-one,
(S)-5-(3-methylisothiazol-5-yl)-3(quinolin-6-yl)ethyl)-6,7-dihydro-3H-[1,2,3]triazolo[4,5- c]pyridin-4(5H)-one,
(R)-5-(3-methylisothiazol-5-yl)-3(1-(quinolin-6-yl)ethyl)-6,7-dihydro-3H-[1,2,3]triazolo[4,5- c]pyridin-4(5H)-one,
(S)-(5)-(3-methylisothiazol-5-yl)-3-(1-(quinolin-6-yl)ethyl)-3H-[1,2,3]triazolo[4,5-c]pyridin-4(5H)-one,
(R)-5-(3-methylisothiazol-5-yl)-3-(1-(quinolin-6-yl)ethyl)-3H-[1,2,3]triazolo[4,5-c]pyridin-4(5H)-one,
(S)-5-(1-methyl-1H-pyrazol-4-yl)-3-(1-(quinolin-6-yl)ethyl)-3H-[1,2,3]triazolo[4,5-c]pyridin-4(5H)-one,
(R)-5-(1-methyl-1H-pyrazol-4-yl)-3-(quinolin-6-yl)ethyl)-3H-[1,2,3]triazolo[4,5-c]pyridin-4(5H)-one,
1-(1-(quinolin-6-yl)ethyl)-1H-[1,2,3]triazolo[4,5-c]pyridin-4(5H)-one, 6-(1-methyl-1H-pyrazol-4-yl)-1-(1-(quinolin-6-yl)ethyl)-1H-[1,2,3]triazolo[4,5-c]pyridin-4(5H)-one, (S)-3-(1-(3(2-methxyethoxy)quinolin-6-yl)ethyl)-5-(3-methylisothiazol-5-yl)-3H-[1,2,3]triazolo[4,5-c]pyridin-4(5H)-one, (R)-3-(1-(3-(2-methoxyethoxy)quinolin-6-yl)ethy)-5-(3-methylisothiazol-5-yl)-3H-[1,2,3]triazolo[4,5-c]pyridin-4(5H)-one, (S)-3-(1-((3-methoxyquinolin-6-yl)ethyl)-5-(3-methyl-isothiazol-5-yl)-3H-[1,2,3]triazolo[4,5-c]pyridin-4(5H)-one, (R)-3-(1-(3-methoxyquinolin-6-yl)ethyl)-5-(3-methyl-isothiazol-5-yl)-3H-[1,2,3]triazolo[4,5-c]pyridin-4(5H)-one, (S)-5-(3,4-difluorophenyl)-3-(1-(3-(2-methoxyethoxy)quinolin-6-yl)ethyl)-3H-[1,2,3]triazolo[4,5-c]pyridin-4(5H)-one, (R)-5-(3,4-difluorophenyl)-3-(1-(3-(2-methoxyethoxy)quinoin-6-yl)ethyl)-3H-[1,2,3]triazolo[4,5-c]pyridin-4(5H)-one, (S)-5-(3,5-difluorophenyl)-3-(1-(3-(2-methoxyethoxy)quinolin-6-yl)ethyl)-3H-[1,2,3]triazolo[4,5-c]pyridin-4(5H)-one, (R)-5-(3,5-difluoropheny)-3-(1-(3-(2-methoxyethoxy)quinolin-6-yl)ethyl-3H-[1,2,3]triazolo[4,5-c]pyridin-4(5H)-one, 3-((3-(2-methoxyethoxy)quinolin-6-yl)methyl)-5-(thiophen-2-yl)-3H-[1,2,3]triazolo[4,5-c]pyridin-4(5H)-one, 5-(3,5-difluorophenyl)-3-((3-(2-methoxyethoxy)quinolin-6-yl)methyl)-3H-[1,2,3]triazolo[4,5-c]pyridin-4(5H)-one, 5-(3,5-difluorophenyl)-3-((3-methoxyquinolin-6-ly)methyl)-3H-[1,2,3]triazolo[4,5-c]pyridin-4(5H)-one, (S)-3-(1-(3-(2-methoxyethoxy)quinolin-6-yl)ethyl)-5-(thiophen-2-yl)-3H-[1,2,3]triazolo[4,5-c]pyridin-4(5H)-one, (R)-3-(1-(3-(2-methoxyethoxy)quinolin-6-yl)ethyl)-5-thiophen-2-yl)-3H-[1,2,3]triazolo[4,5-c]pyridin-4(5H)-one, 3-((3-(2-methoxyethoxy)quinolin-6-yl)methyl)-5-(3-methylisothiazol-5-yl)3H-[1,2,3]triazolo[4,5-c]pyridin-4(5H-one, 3-((3-methoxyquinolin-6-yl)methyl)-5-(3-methylisothiazol-5-yl)-3H-[1,2,3]triazolo[4,5-c]pyridin-4(5H)-one, (S)-5-(4-chloro-3-(trifluoromethyl)phenyl)-3-(1-(quinolin-6-yl)ethyl)-3H-[1,2,3]triazolo[4,5-c]pyridin-4(5H)-one, (R)-5-(4-chloro-3-(trifluoromethyl)phenyl)-3-(1-(quinolin-6-yl)ethyl)-3H-[1,2,3]triazolo[4,5-c]pyridin-4(5H)-one, (S)-5-benzyl-3-(1-(quinolin-6-yl)ethyl)-3H-[1,2,3]triazolo[4,5-c]pyridin-4(5H)-one, (R)-5-benzyl-3-(1-(quinolin-6-yl)ethyl)-3H-[1,2,3]triazolo[4,5-c]pyridin-4(5H)-one, (S)-5-(5-methylthiophen-2-yl)-3-(1-(quinolin-6-yl)ethyl)-3H-[1,2,3]triazolo[4,5-c]pyridin-4-(5H)-one, (R)-5-(5-methylthiophen-2-yl)-3-(1-(quinolin-6-yl)ethyl)-3H-[1,2,3]triazolo[4,5-c]pyridin-4-(5H)-one, (S)-5-(4-methylthiophen-2-yl)-3-(1-(quinolin-6-yl)ethyl)-3H-[1,2,3]triazolo[4,5-c]pyridin-4-(5H)-one, and (R)-5-(4-methylthiophen-2-yl)-3-(1-(quinolin-6-yl)ethyl)-3H-[1,2,3]triazolo[4,5-c]pyridin-4-(5H)-one.

5. A pharmaceutical composition comprising a compound of claim 1 or claim 4, together with a pharmaceutically acceptable vehicle, adjuvant or diluent.

* * * * *

UNITED STATES PATENT AND TRADEMARK OFFICE
CERTIFICATE OF CORRECTION

PATENT NO.         : 8,691,838 B2                                                        Page 1 of 1
APPLICATION NO.    : 12/994068
DATED              : April 8, 2014
INVENTOR(S)        : Albrecht et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 419 days.

Signed and Sealed this
Twenty-ninth Day of September, 2015

Michelle K. Lee
*Director of the United States Patent and Trademark Office*